United States Patent
Chiu et al.

(10) Patent No.: US 9,085,548 B2
(45) Date of Patent: Jul. 21, 2015

(54) PSEUDOROTAXANES, ROTAXANES AND CATENANES FORMED BY METAL IONS TEMPLATING

(71) Applicant: NATIONAL TAIWAN UNIVERSITY, Taipei (TW)

(72) Inventors: Sheng-Hsien Chiu, Taipei (TW); You-Han Lin, Taichung (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/526,507

(22) Filed: Oct. 28, 2014

(65) Prior Publication Data

US 2015/0051393 A1 Feb. 19, 2015

Related U.S. Application Data

(62) Division of application No. 13/901,597, filed on May 24, 2013, now Pat. No. 8,952,167.

(51) Int. Cl.
| | | |
|---|---|---|
| *C07D 323/00* | (2006.01) | |
| *C07D 498/06* | (2006.01) | |
| *C07D 405/12* | (2006.01) | |
| *C07D 267/00* | (2006.01) | |
| *C07D 327/00* | (2006.01) | |
| *C07D 498/08* | (2006.01) | |
| *C07D 498/18* | (2006.01) | |

(52) U.S. Cl.
CPC ............ *C07D 323/00* (2013.01); *C07D 267/00* (2013.01); *C07D 327/00* (2013.01); *C07D 405/12* (2013.01); *C07D 498/06* (2013.01); *C07D 498/08* (2013.01); *C07D 498/18* (2013.01)

(58) Field of Classification Search
CPC ... C07D 323/00; C07D 327/00; C07D 498/08
USPC ........................................ 540/469
See application file for complete search history.

*Primary Examiner* — Paul V Ward
(74) *Attorney, Agent, or Firm* — CKC & Partners Co., Ltd.

(57) ABSTRACT

A pseudorotaxane, a rotaxane and a catenane are provided. The pseudorotaxane includes at least a macrocyclic host molecule, a guest molecule, and a metal ion. The host molecule contains at least a binding unit and an aromatic linking spacer. The guest molecule has at least a recognition unit. The metal ion is used to template the threading of the guest molecule through the macrocycle host molecule by coordinating to a binding pocket formed from the binding unit of the macrocycle and the recognition moiety of the guest molecule. Rotaxanes or catenanes can be synthesized from the pseudorotaxane complexes, with or without the metal template ion in their molecular structures.

11 Claims, 24 Drawing Sheets

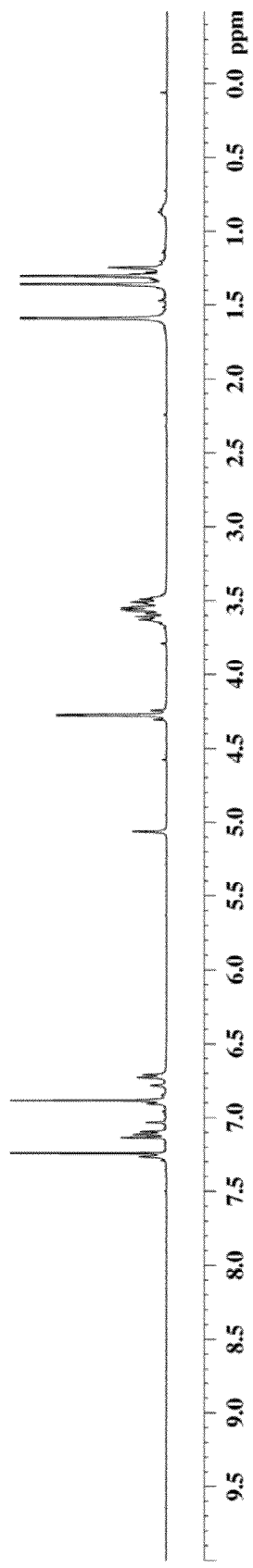
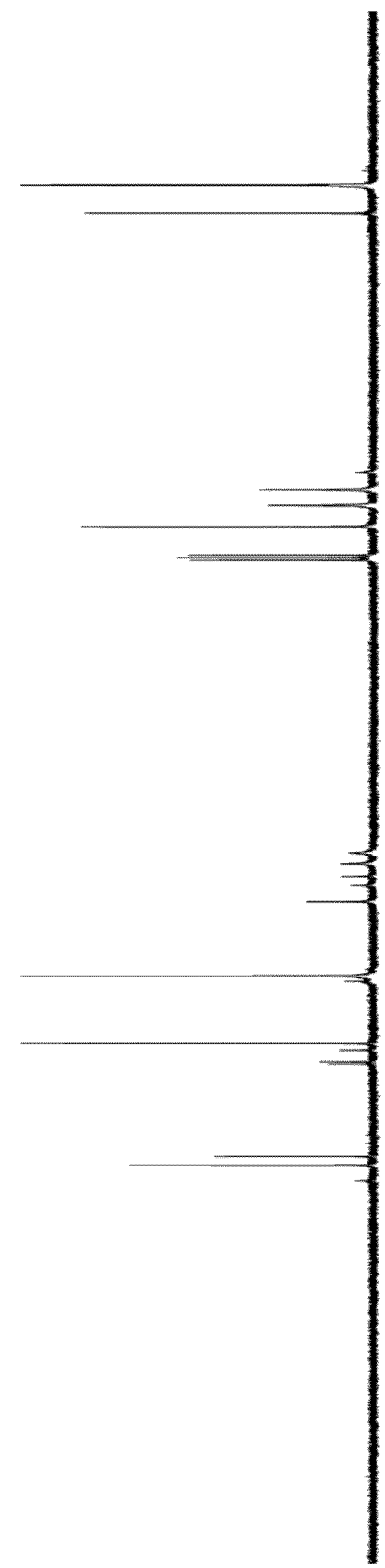
Fig. 3A
Fig. 3B

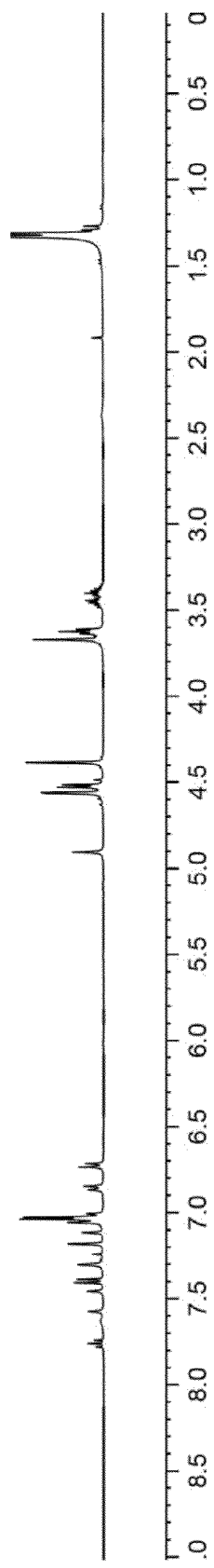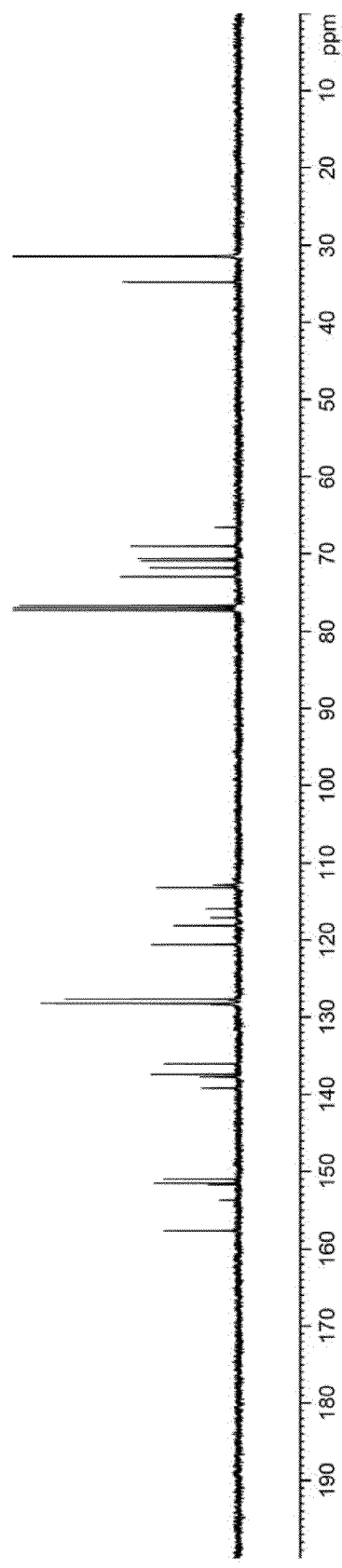
Fig. 4A
Fig. 4B

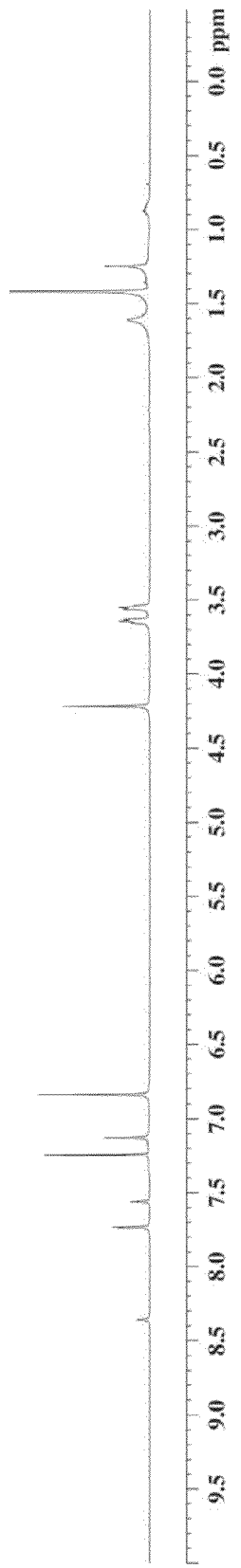
Fig. 9A
Fig. 9B

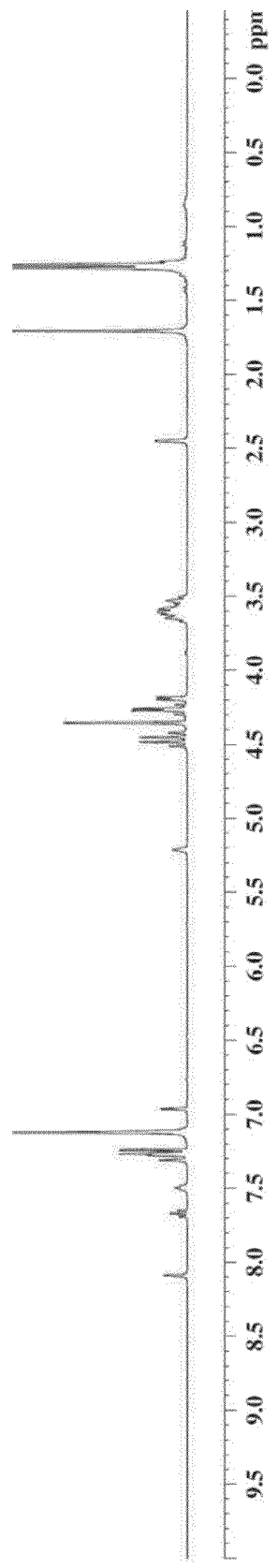
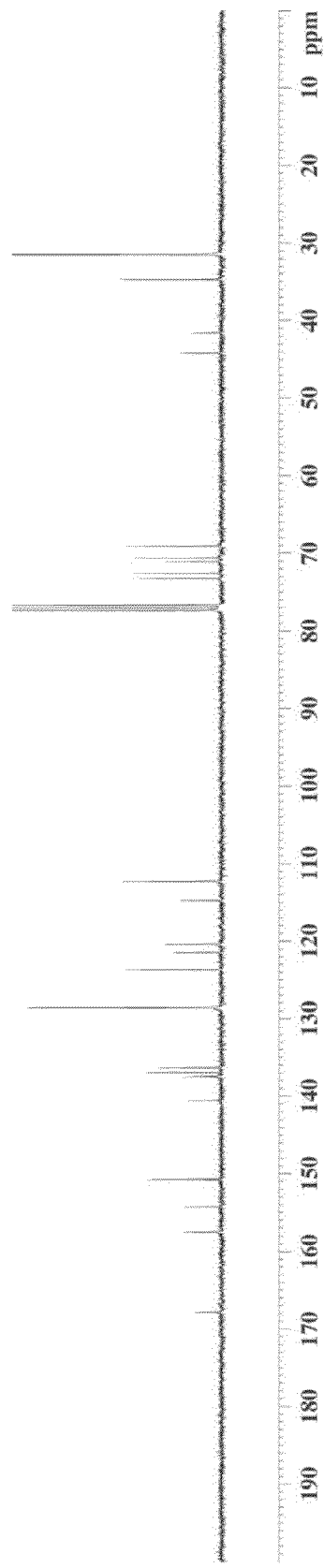
Fig. 11A
Fig. 11B

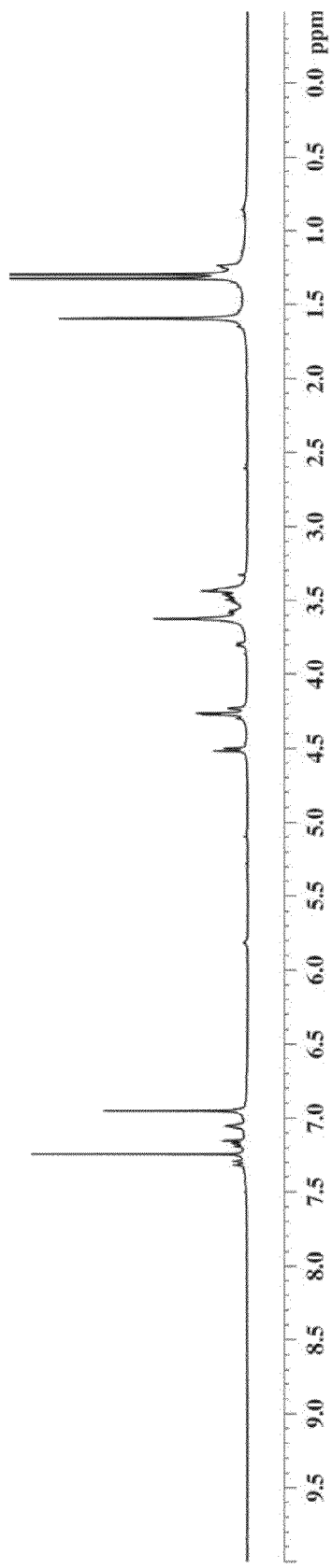
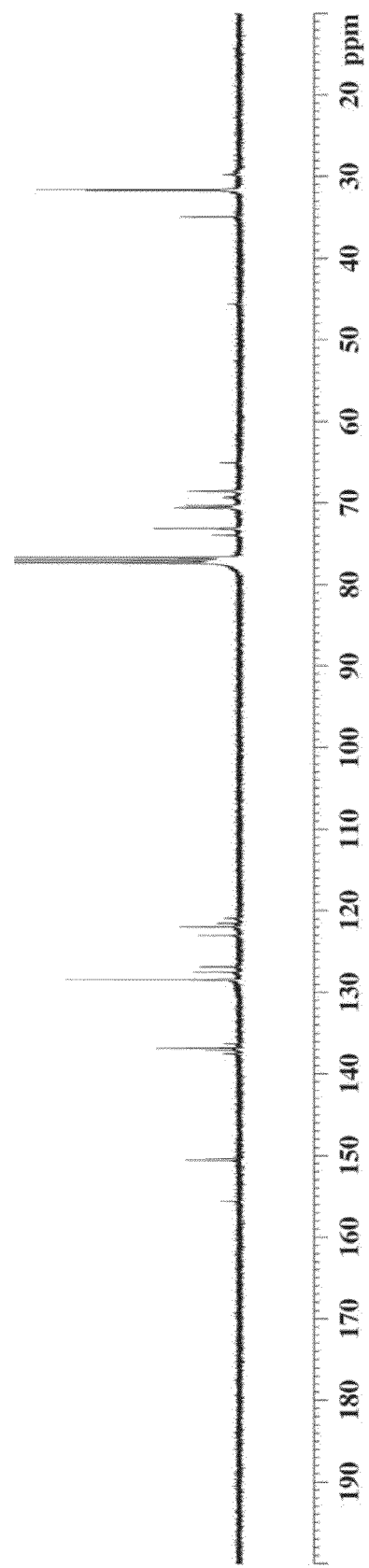
Fig. 18A
Fig. 18B

PSEUDOROTAXANES, ROTAXANES AND CATENANES FORMED BY METAL IONS TEMPLATING

RELATED APPLICATIONS

This application is a divisional application of co-pending U.S. patent application Ser. No. 13/901,597 for the same title filed on May 24, 2013, the content of which is hereby incorporated by reference in its entirety.

BACKGROUND

1. Technical Field

The disclosure relates to a host-guest complex or an interlocked molecule, especially a pseudorotaxane, a rotaxane or a catenane.

2. Description of Related Art

Pseudorotaxanes, rotaxanes and catenanes are becoming increasingly important materials for gelation, drug delivery, and molecular electronics; therefore, efforts continue toward developing new threading systems and new methods to synthesize these intertwined and interlocked molecules. Although many elegant interlocked molecular compounds and threaded supramolecular complexes have been prepared in the past two decades, the number of recognition motifs that can be exploited for the preparation of these systems remains limited. This difficulty arises mainly from the limited ability to incorporate suitable recognition units in an appropriate arrangement in the molecular structures of the host and guest components, so that weak noncovalent interactions can collaborate together to stabilize the resulting pseudorotaxane complexes. In addition, the lack of structural flexibility of the recognition units that can form pseudorotaxane complexes hinders the application of unique functions or structures into already practically used materials and/or biologically important (macro)molecules, many of which do not contain the necessary, suitably arranged recognition units in their native molecular structures.

SUMMARY

Accordingly, in one aspect, the present invention is directed to a pseudorotaxane complex, a rotaxane molecule, or a catenane molecule. In the complex or molecule, the recognition moiety of a guest molecule used for the host-guest assembly can contain only a simple functional group, such as a urea group, a carbamate group, an amide group, an oligo(ethylene glycol) group or a 2,6-bis(hydroxymethyl)pyridine group.

The pseudorotaxane complex comprises at least a host molecule, a guest molecule, and a metal ion. The host molecule has a macrocyclic structure comprising at least a binding unit and an aromatic linking spacers. The binding unit can be an oligo(ethylene glycol) group, or a 2,6-bis(hydroxymethyl)pyridine group. The guest molecule has at least a recognition moiety, such as an urea group, a carbamate group, an amide group, an oligo(ethylene glycol) group, or a 2,6-bis(hydroxymethyl)pyridine group. The metal ion coordinates to the binding unit of the host molecule and the recognition moiety of the guest molecule.

According to an embodiment of this invention, the host molecule further comprises a binding assistant unit, such as an oligo(ethylene glycol) group, a 2,6-bis(hydroxymethyl)pyridine, a 2,2'-oxy-di(ethanethiol) group, a 1,3-bis(iminomethyl)benzene group or a 2,6-bis(iminomethyl)pyridine group.

According to another embodiment, the aromatic linking spacer can be a p-xylenyl group or a 2,6-lutidinyl group.

According to yet another embodiment, the host molecule can be

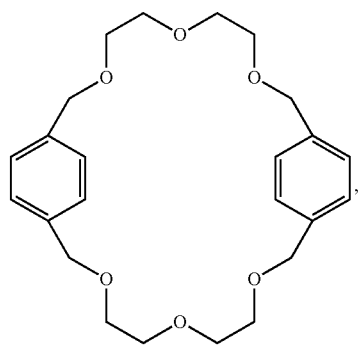

,

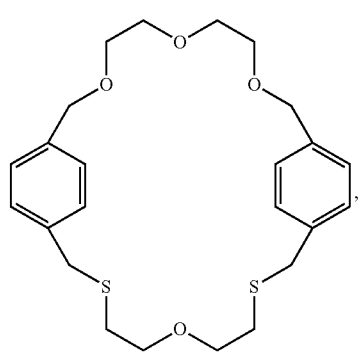

,

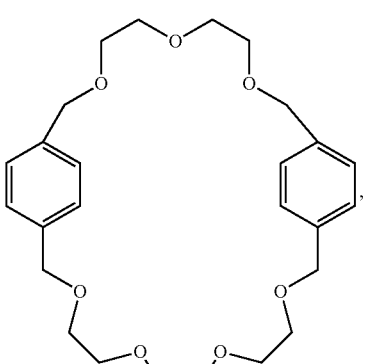

,

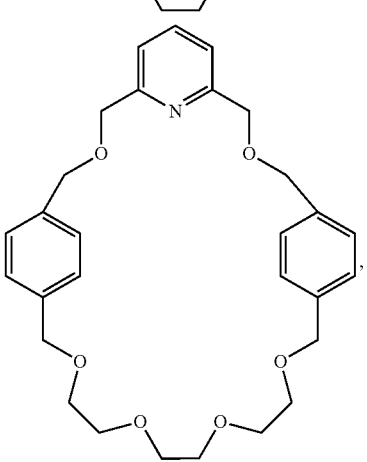

,

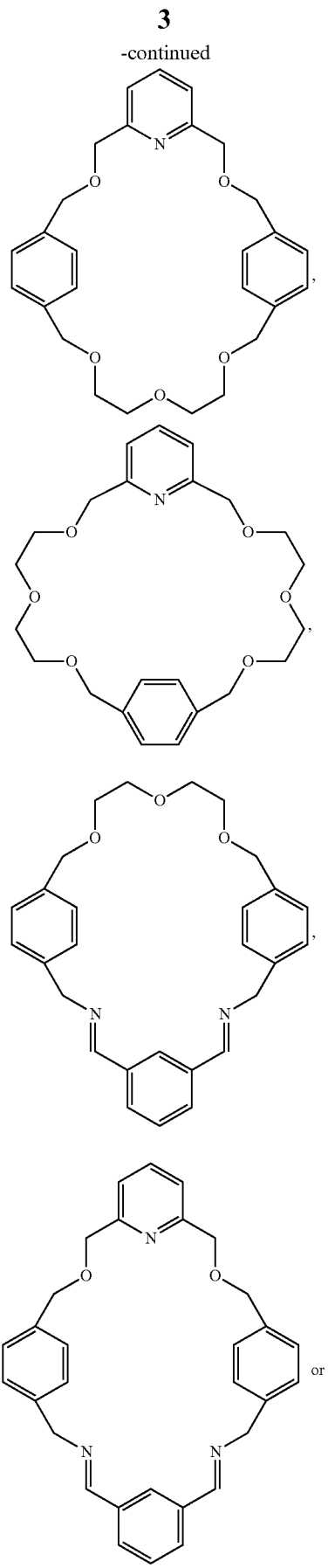

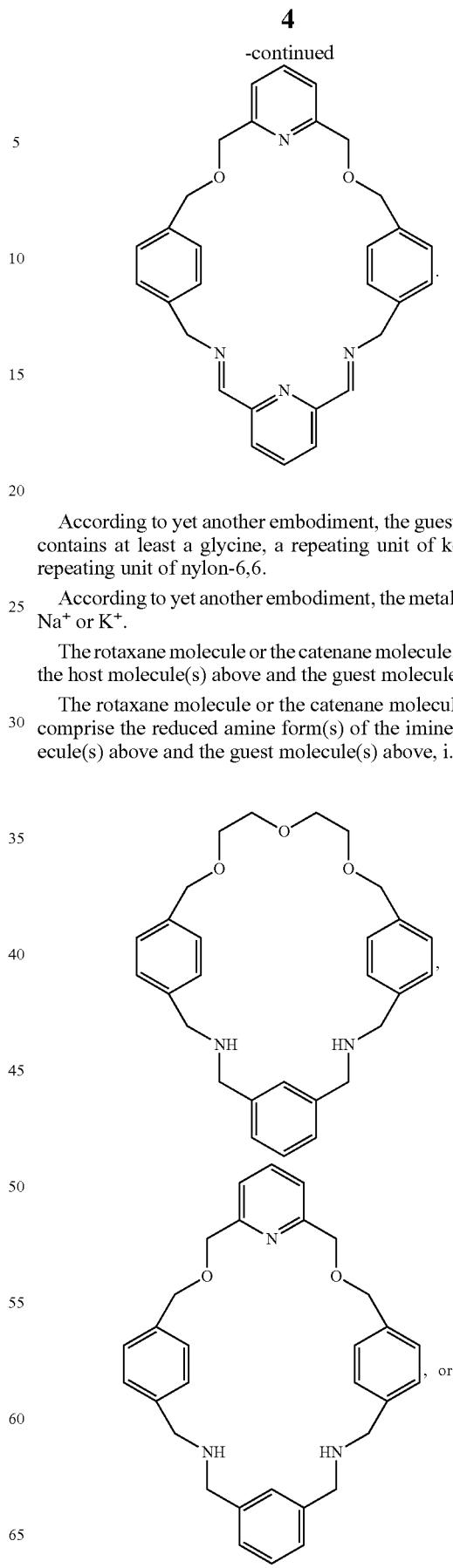

According to yet another embodiment, the guest molecule contains at least a glycine, a repeating unit of kevlar, or a repeating unit of nylon-6,6.

According to yet another embodiment, the metal ion is $Li^+$, $Na^+$ or $K^+$.

The rotaxane molecule or the catenane molecule comprises the host molecule(s) above and the guest molecule(s) above.

The rotaxane molecule or the catenane molecule also can comprise the reduced amine form(s) of the imine host molecule(s) above and the guest molecule(s) above, i.e.

-continued

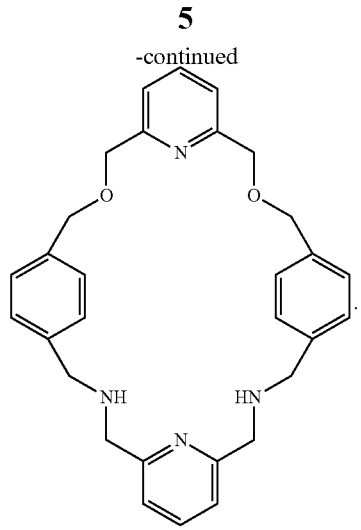

Accordingly, a new molecular recognition system has been discovered. In this new recognition system, a single recognition moiety of a threaded guest molecule can be recognized by a host molecule via a templating metal ion.

The foregoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later. It is to be understood that both the foregoing general description and the following detailed description are by examples, and are intended to provide further explanation of the invention as claimed.

BRIEF DESCRIPTION OF THE DRAWINGS

FIGS. 3A and 3B are $^1$H NMR (400 MHz, CDCl$_3$, 298 K) and $^{13}$C NMR (100 MHz, CDCl$_3$, 298 K) spectra of rotaxane 1, respectively.

FIGS. 4A and 4B are $^1$H NMR (400 MHz, CDCl$_3$, 298 K) and $^{13}$C NMR (100 MHz, CDCl$_3$, 298 K) spectra of rotaxane 2, respectively.

FIGS. 9A and 9B are $^1$H NMR (400 MHz, CDCl$_3$, 298 K) and $^{13}$C NMR (100 MHz, CDCl$_3$, 298 K) spectra of rotaxane 10, respectively.

FIGS. 11A and 11B are $^1$H NMR (400 MHz, CDCl$_3$, 298 K) and $^{13}$C NMR (100 MHz, CDCl$_3$, 298 K) spectra of rotaxane 14, respectively.

FIGS. 18A and 18B are $^1$H NMR (400 MHz, CDCl$_3$, 298 K) and $^{13}$C NMR (100 MHz, CDCl$_3$, 298 K) spectra of rotaxane 23, respectively.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

Pseudorotaxanes, Rotaxanes or Catenanes

In one aspect, a pseudorotaxane complex, a rotaxane or a catenane is provided. The pseudorotaxane complex comprises at least a host molecule, a guest molecule, and a metal ion. The rotaxanes and catenanes both comprise a host molecule and a guest molecule, and the guest molecule of the catenanes having a macrocyclic structure.

The host molecule has a macrocyclic structure. The macrocyclic structure has at least a binding unit and at least an aromatic linking spacer. The binding unit can be an oligo(ethylene glycol) group or a 2,6-bis(hydroxymethyl)pyridine.

The aromatic linking spacer can be a p-xylenyl group or a 2,6-lutidinyl group. Optionally, the macrocyclic structure can further has a binding assistant unit, such as an oligo(ethylene glycol) group, a 2,6-bis(hydroxymethyl)pyridine, a 2,2'-oxy-di(ethanethiol) group, a 1,3-bis(iminomethyl)benzene group, a 1,3-bis(aminomethyl)benzene group, a 2,6-bis(iminomethyl)pyridine group, or a 2,6-bis(aminomethyl)pyridine group. For example, the macrocyclic host molecule can has one binding unit, one binding assistant unit, and two linking spacers respectively disposed between the binding unit and the binding assistant unit to respectively link the binding unit and the binding assistant unit. According to an embodiment, some examples of the host molecule are listed in table 1 below.

TABLE 1

| Some examples of the host molecule | |
| --- | --- |
| 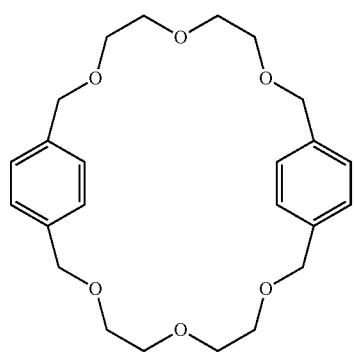 | MC1 |
| 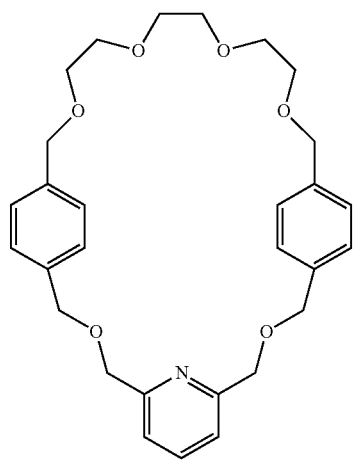 [SMILES: c1cc2nc(c1)COCc1ccc(cc1)COCCOCCOCCOCc1ccc(cc1)COC2] | MC2 |
| 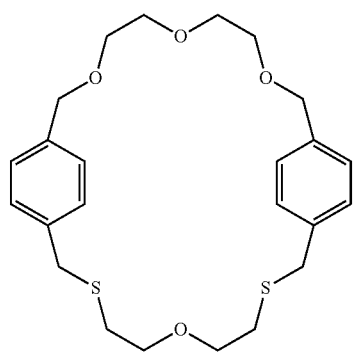 [SMILES: c1cc2ccc1COCCOCCOCc1ccc(cc1)CSCCOCCSC2] | MC3 |

TABLE 1-continued

| Some examples of the host molecule | |
| --- | --- |
| 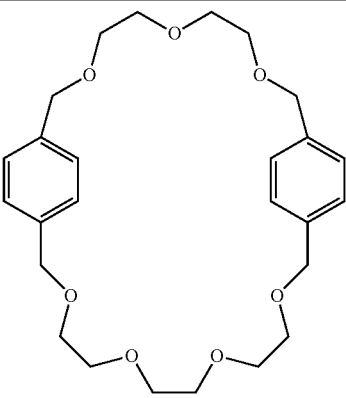 | MC4 |
| 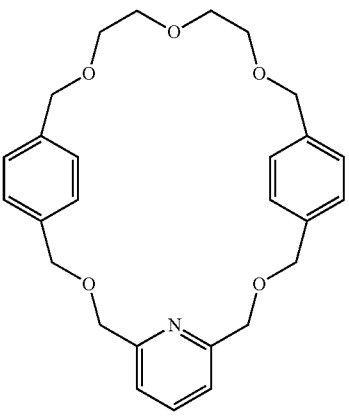 [SMILES: c1cc2nc(c1)COCc1ccc(cc1)COCCOCCOCc1ccc(cc1)COC2] | MC5 |
| 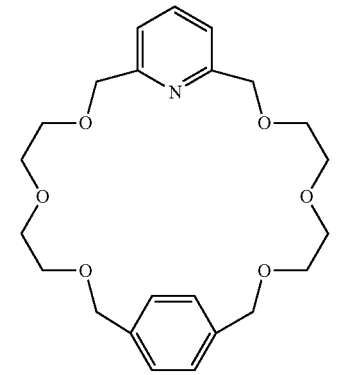 [SMILES: c1cc2nc(c1)COCCOCCOCc1ccc(cc1)COCCOCCOC2] | MC6 |
| 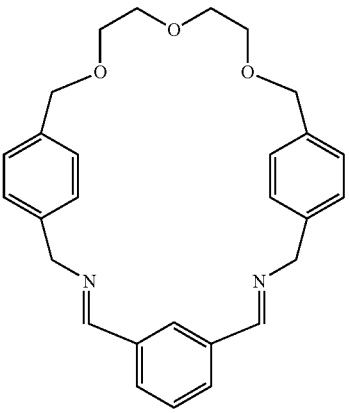 [SMILES: C1=N/Cc2ccc(cc2)COCCOCCOCc2ccc(cc2)C/N=C/c2cccc/1c2] | MC7 |

TABLE 1-continued

Some examples of the host molecule

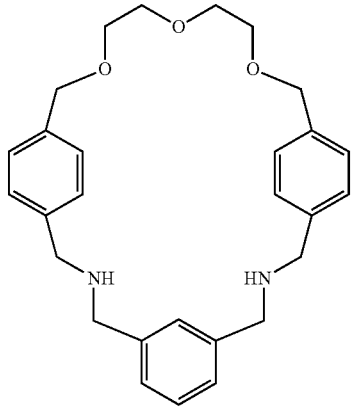 [SMILES: c1cc2cc(c1)CNCc1ccc(cc1)COCCOCCOCc1ccc(cc1)CNC2]
MC8

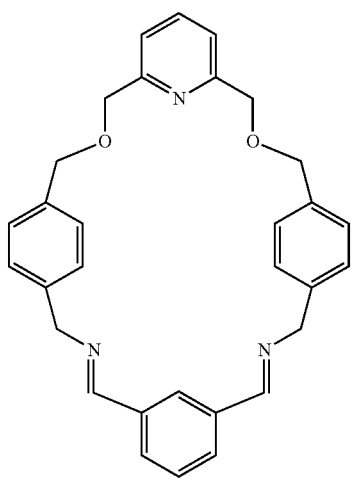
MC9

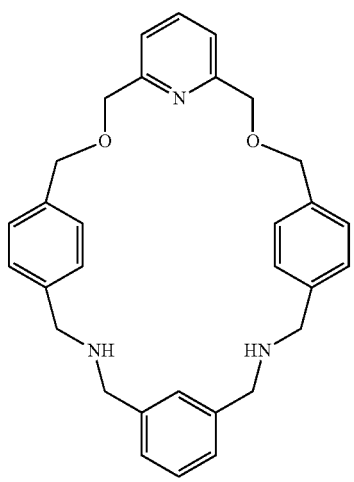 [SMILES: c1cc2cc(c1)CNCc1ccc(cc1)COCc1cccc(n1)COCc1ccc(cc1)CNC2]
MC10

TABLE 1-continued

Some examples of the host molecule

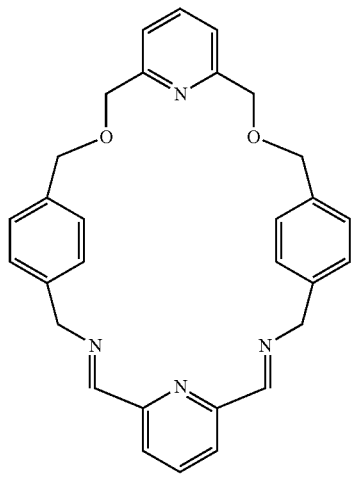 [SMILES: C1=N/Cc2ccc(cc2)COCc2cccc(n2)COCc2ccc(cc2)C/N=C/c2cccc/1n2]
MC11

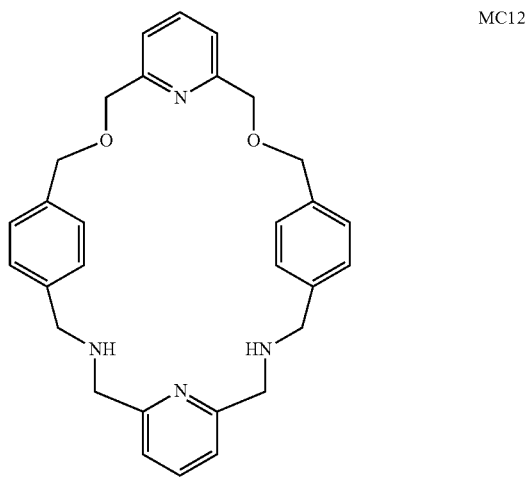
MC12

The guest molecule has at least a recognition moiety, such as a urea group, a carbamate group, an amide group, an oligo(ethylene glycol) group, or a 2,6-bis(hydroxymethyl) pyridine group.

The metal ion is used to template the threading of the guest molecule above through the macrocycle by coordinating to a binding pocket formed from the binding unit of the macrocyclic host molecule and the recognition moiety of the guest molecule. According to an embodiment, the metal ion can be an alkali metal ion, such as $Li^+$, $Na^+$ or $K^+$. For example, the binding pocket can be formed from the oligo(ethylene glycol) moiety of the macrocyclic host molecule, and the carbonyl (C=O) group or the ether (—$CH_2$—O—$CH_2$—) group of the guest molecule.

Figure 1A:
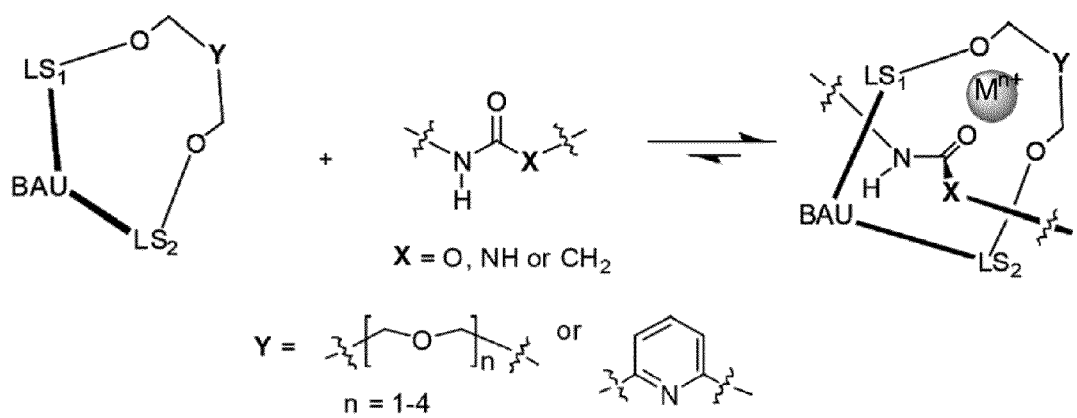
FIGS. 1A-1B are diagrams of the interaction between the host molecule, the guest molecule having a urea group, a carbamate group, an amide group, an oligo(ethylene glycol) group or a 2,6-bis(hydroxymethyl)pyridine group and the metal ion.
Figure 1B:
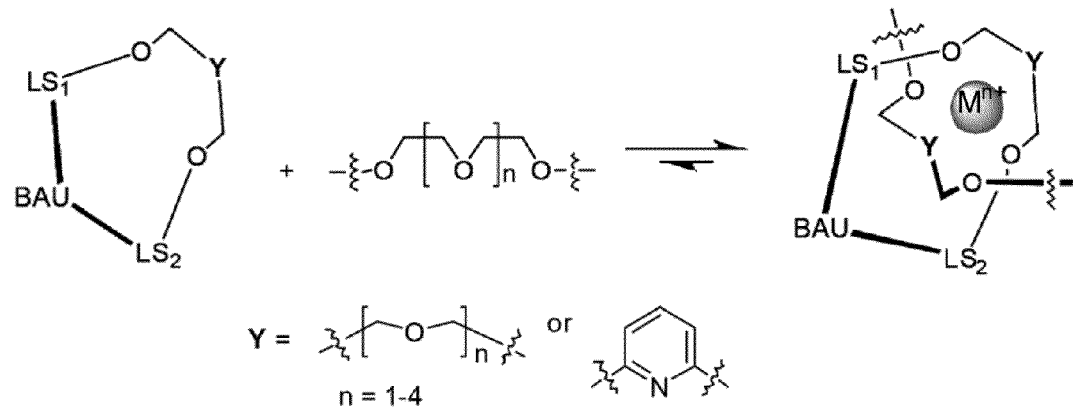

The interactions between the host molecule, the guest molecule, and the metal ion are shown in FIG. 1A and FIG. 1B. For better and easier illustrating the interactions between the host molecule, the guest molecule, and the metal ion, the binding unit is presented by

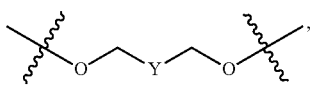

the binding assistant unit is abbreviated as BAU, and the two linking spacers are abbreviated as $LS_1$ and $LS_2$ in FIGS. 1A and 1B.

In FIG. 1A the guest molecule has a urea group, a carbamate group, or an amide group. In FIG. 1B, the guest molecule has an oligo(ethylene glycol) group or a 2,6-bis(hydroxymethyl)pyridine group. In FIG. 1A or 1B, the metal ion is used to template the threading of the guest molecule through the macrocycle by coordinating to the binding pocket formed from the oligo(ethylene glycol) moiety or the 2,6-bis(hydroxymethyl)pyridine moiety of the macrocycle, and the C=O group (FIG. 1A), the ether group (FIG. 1B) or the 2,6-bis(hydroxymethyl)pyridine (FIG. 1B) of the guest. In addition, [N—H . . . O] or [N—H . . . N] hydrogen bonds formed between the NH proton of the recognition moiety (i.e. the urea group, the carbamate group, or the amide group) to the oxygen or nitrogen atom in the binding assistant unit (BAU in FIGS. 1A and 1B), may help to further stabilize the structure of the pseudorotaxane complexes.

Some examples of the pseudorotaxane complexes and the interlocked molecules, such as rotaxanes and catenanes, are described below. The formation of the pseudorotaxane complexes in solution is proven by the successful synthesis of the corresponding rotaxanes or catenanes. For synthesizing a rotaxane molecule, a stoppering agent is used to interlock the host molecule to prevent its dethreading from the guest component. In the examples below, some stoppering agents were used, and are listed in table 2 below.

TABLE 2

| Stoppering agent | |
|---|---|
| ![SA1 structure] | SA1 |
| ![SA2 structure] | SA2 |
| ![SA3 structure] | SA3 |
| ![SA4 structure] | SA4 |
| ![SA5 structure] | SA5 |
| ![SA6 structure] | SA6 |
| ![SA7 structure] | SA7 |

A rotaxane or a catenane can also be synthesized through the self-assembly process, in which the recognition site of the guest molecule was encircled by the macrocycle preformed or in situ generated from the imine formation reaction of a dialdehyde and a diamine via the templating of metal ion. In the examples below, some dialdehydes and diamines were used and are listed in table 3 below.

TABLE 3

Dialdehydes and diamines used for the construction of catenanes

| Dialdehydes | Diamines |
|---|---|
| DAD1 | DAM1 |
| DAD2 | DAM2 |

Embodiment 1

Guest Molecules Containing a Urea Group

Example 1

Urea 1

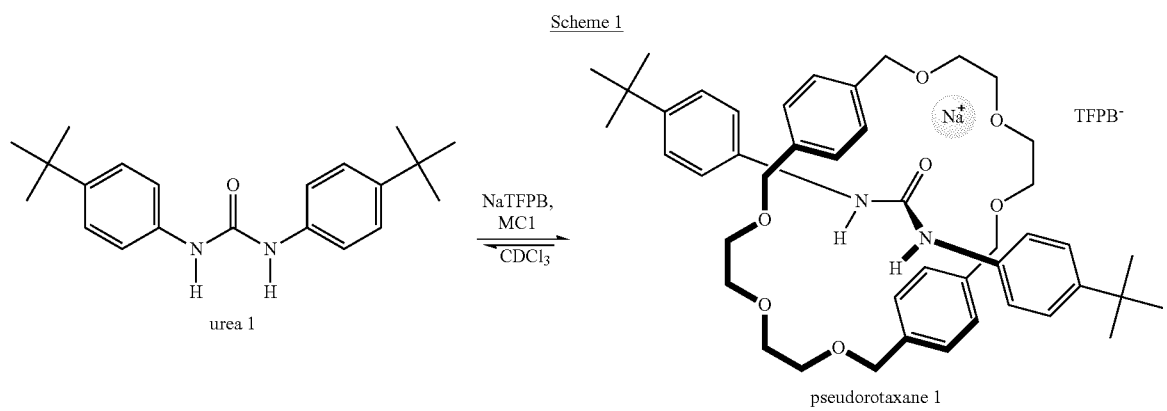

Scheme 1

In this example, urea 1 having a urea group conjugated to two aromatic rings was used as the guest molecule. MC1 was used as the host molecule. Since the hydrogen bonding between urea 1 and MC1 and the ion-dipole interaction between both of them and the metal ion template would both prefer less-polar solvents, sodium tetrakis(3,5-trifluoromethylphenyl)borate (NaTFPB) was chosen as the templating salt because of its relatively weak ion-pairing tendency in such solvents. The chemical structure of NaTFPB is shown below.

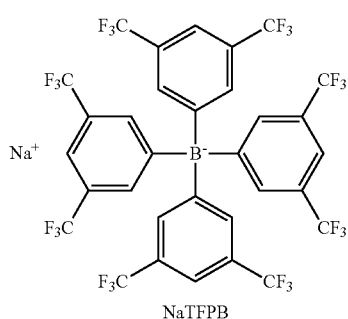

NaTFPB

Urea 1, MC1, and NaTFPB were mixed in various molar ratios in CDCl₃ for measuring ¹H NMR spectra. The obtained ¹H NMR spectra are shown in spectra 2C-2F in FIG. 2, respectively. In addition, the ¹H NMR spectra of urea 1 as well as an equimolar mixture of urea 1 and MC1 are also shown in spectra 2A and 2B in FIG. 2 for comparison.

Figure 2:
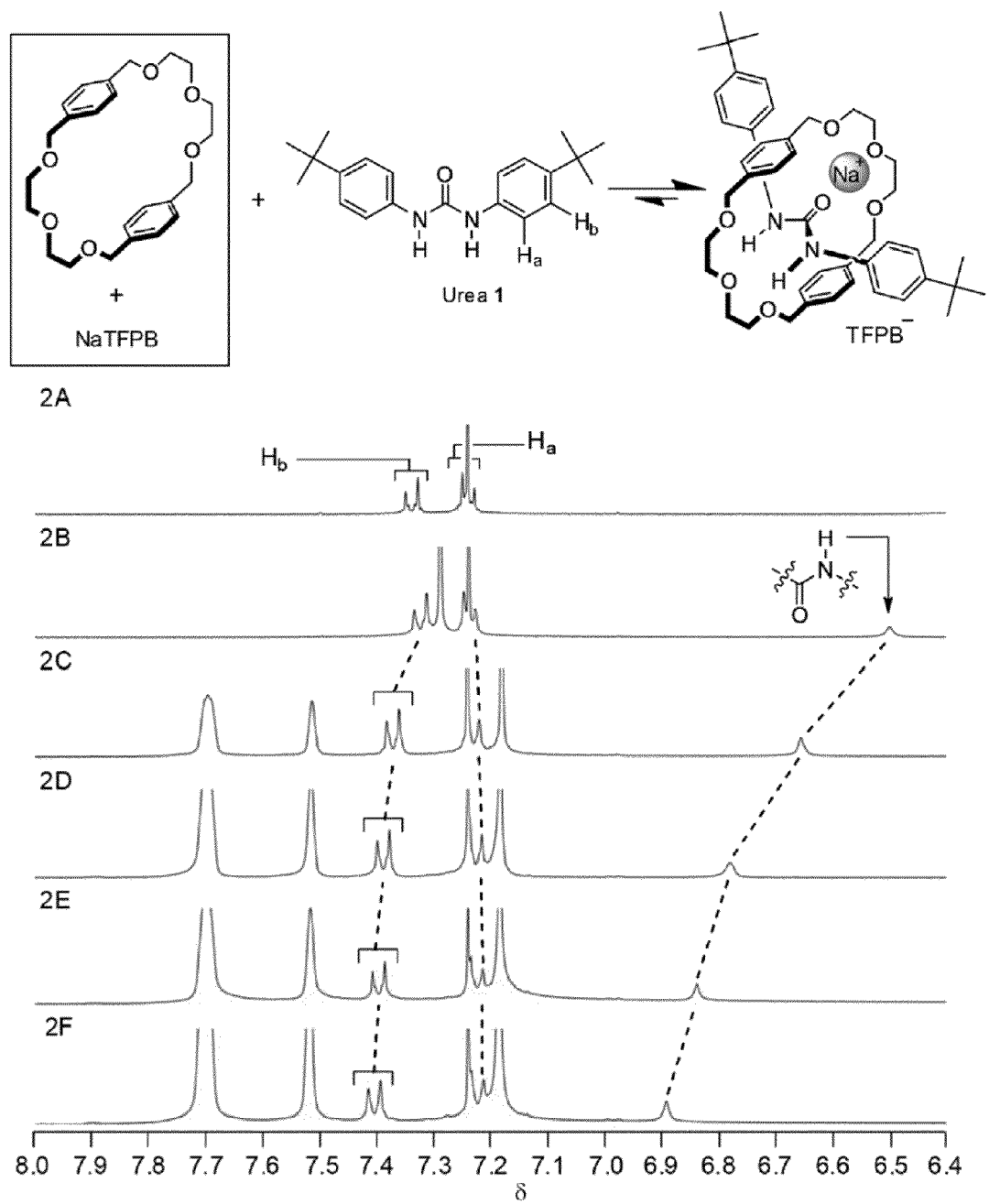
FIG. 2 containing spectra 2A to 2F, and spectrum 2A is $^1$H NMR spectrum (400 MHz, CDCl$_3$, 298 K) of the threadlike urea 1; spectrum 2B is $^1$H NMR spectrum (400 MHz, CDCl$_3$, 298 K) of an equimolar mixture of urea 1 and MC1 (5 mM); spectra 2C-2F are $^1$H NMR spectra (400 MHz, CDCl$_3$, 298 K) of mixtures of urea 1, MC1, and NaTFPB at concentrations of 5/5/5 mM, 5/10/10 mM, 5/15/15 mM, and 5/20/20 mM, respectively.

First, spectra 2B and 2C in FIG. 2 are compared. Spectrum 2B is the ¹H NMR spectra of equimolar mixture of urea 1 and MC1 at a concentration of 5 mM. In spectrum 2C, additional 5 mM NaTFPB was added to the CDCl₃ solution. It can be clearly seen that the NMR signals of the urea 1 (marked by $H_a$, $H_b$, and —CO—NH—, respectively) underwent significant shifts before and after adding NaTFPB. This observation suggested that the efficient threading of urea 1 through MC1 required the templating of Na⁺ ions, and the rates of complexation and decomplexation were both fast on the ¹H NMR spectroscopic timescale at 400 MHz and 298 K. The downfield shift of the signal of the NH protons and the respective upfield and downfield shifts of those aromatic protons $H_a$ and $H_b$ upon gradually increasing the concentrations of MC1 and NaTFPB from 5 mM to 20 mM is consistent with the formation of a pseudorotaxane between the host and guest components under these conditions.

The downfield shift of the NMR signal of the NH protons can be explained by the formation of [N—H . . . O] hydrogen bonds between the NH protons of the urea moiety and the oxygen atoms of the diethylene glycol segment. The respective upfield and downfield shifts of the signals of the protons $H_a$ and $H_b$ can be explained by the concomitant shielding and deshielding of the protons $H_a$ and $H_b$ by the p-xylene motifs of the MC1.

Example 2

Urea 2

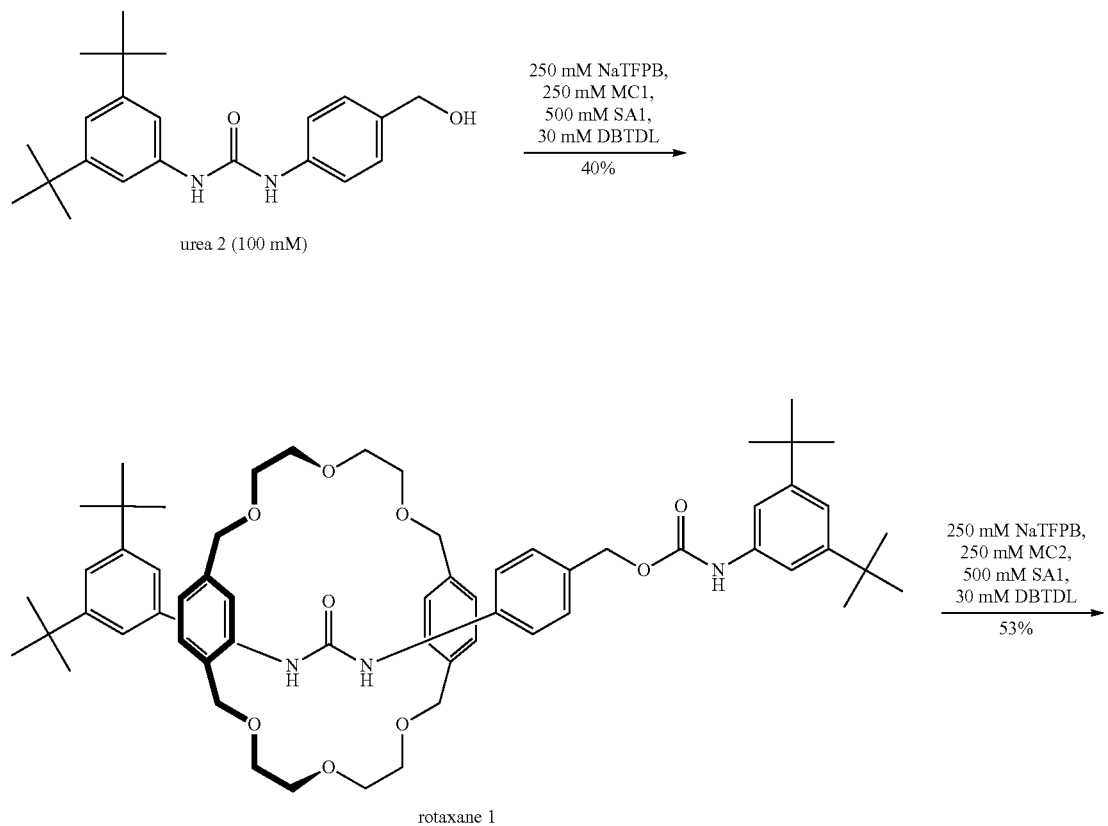

Scheme 2

-continued

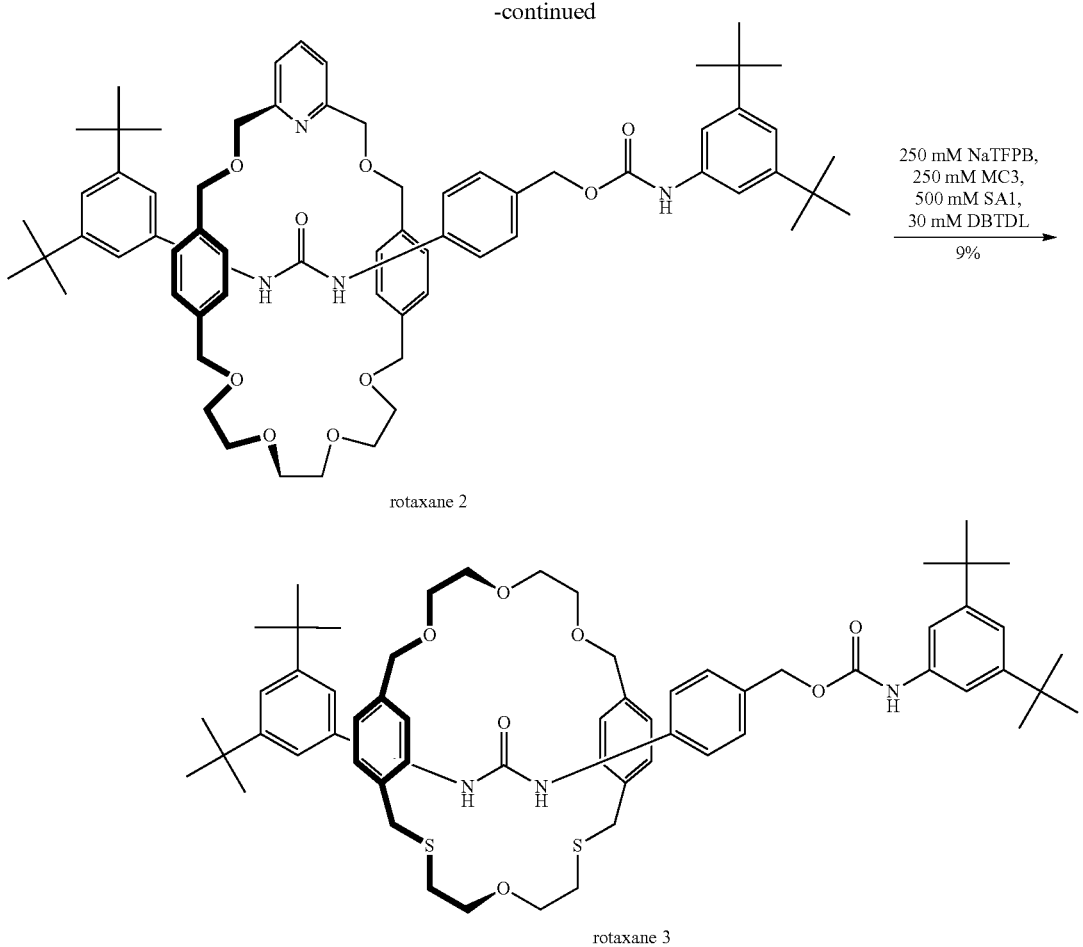

rotaxane 2

250 mM NaTFPB,
250 mM MC3,
500 mM SA1,
30 mM DBTDL
→
9% rotaxane 3

In this example, urea 2 having a urea group conjugated to two aromatic rings was used as the guest molecule. NaTFPB was used as the templating salt. SA1 was used as the stoppering agent. MC1, MC2 and MC3 were respectively used as the host molecule. Di-n-butyltin dilaurate (DBTDL) was used as a catalyst for capping the SA1 to the urea 2. For preparing the rotaxanes 1-3, a $CH_2Cl_2$ solution containing urea 2, NaTFPB, one of the host molecules, and DBTDL was added with SA1, and then stirred at ambient temperature for 16 hours.

The macrocycle interlocked in rotaxane 2 is MC2, in which the two diethylene glycol motifs in MC1 were replaced by a triethylene glycol and a 2,6-bis(hydroxymethyl)pyridine units. The higher yield in the synthesis of rotaxane 2 compared to the one of rotaxane 1, suggested that the 2,6-bis (hydroxymethyl)pyridine unit is a more preorganized and better chelating motif, which energetically overcomes the increasing structural flexibility introduced by the triethylene glycol unit in the host-guest complexation.

MC3, in which two oxygen atoms in the diethylene glycol moiety of MC1 were replaced by sulfur atoms, gave significantly lower yield in the synthesis of its interlocked rotaxane 3. This result may due to the relative flexible molecular structure and the weaker interaction of its binding assistant unit (BAU) to the NH proton of the guest molecule of MC3. Nevertheless, with the assistance from the $Na^+$ ion template, MC3 and urea 2 still can form pseudorotaxane complexes in solution and the corresponding rotaxane 3 was isolated in 9% yield.

The observation of no signal corresponding to TFPB anion in the $^1H$ NMR spectra of the [2]rotaxane 1-3, suggested the templating $Na^+$ ion was completely removed during the aqueous extraction and chromatography process. This result also suggested that the complexation of the $Na^+$ ion to the binding pocket in the [2]rotaxanes was not particularly strong under these conditions. The bulky terminal groups of the threaded guest, however, prevent the dethreading of the interlocked macrocycle even after the loss of the metal ion template.

Figure 5A:
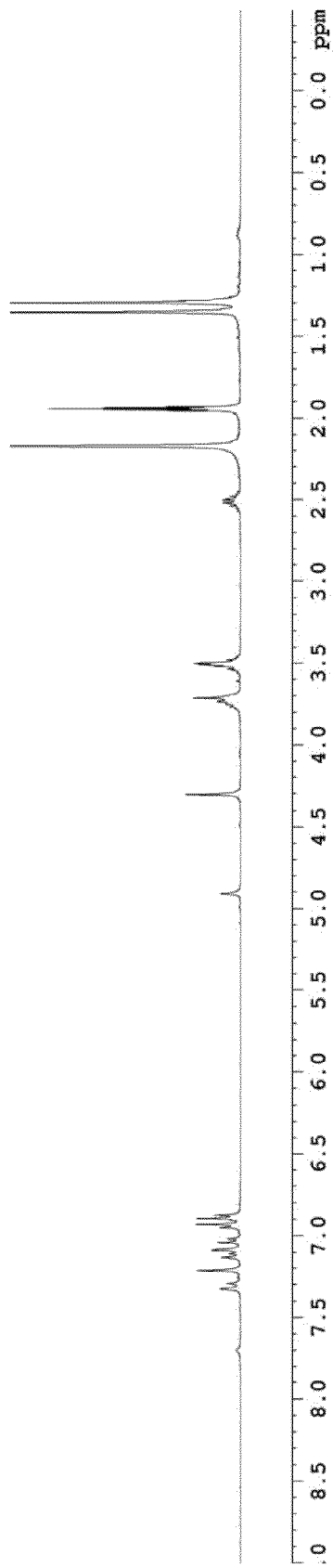
FIGS. 5A and 5B are $^1$H NMR (400 MHz, CD$_3$CN, 298 K) and $^{13}$C NMR (100 MHz, CD$_3$CN, 298 K) spectra of rotaxane 3, respectively.
Figure 5B:
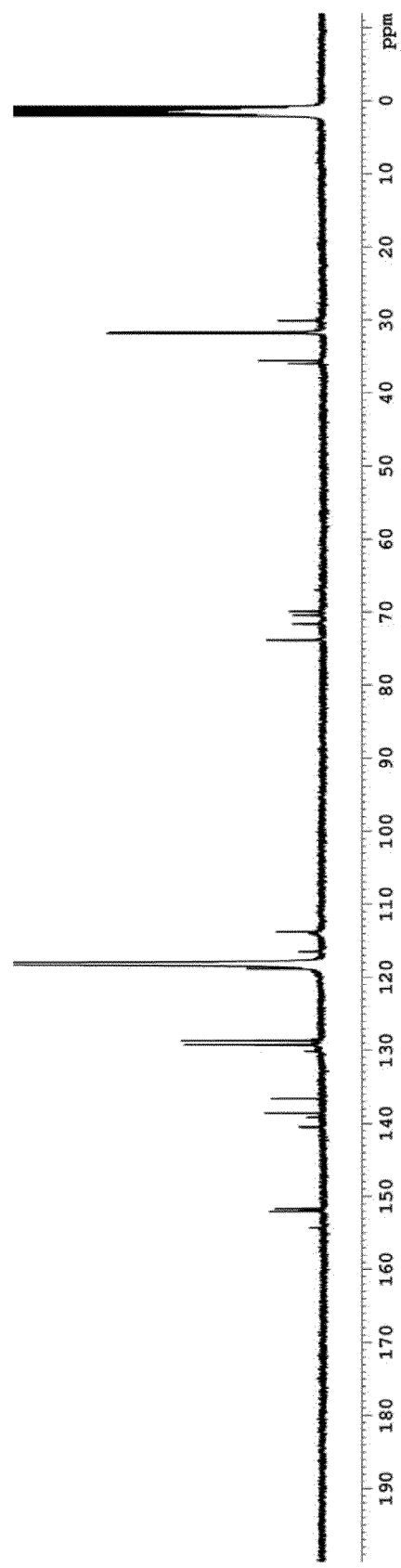

The $^1H$ NMR and $^{13}C$ NMR spectra of rotaxanes 1, 2 and 3 are shown in FIGS. 3, 4 and 5, respectively. All related spectral data are listed below.

Rotaxane 1: M.p. 126-127° C.; $^1H$ NMR (400 MHz, $CDCl_3$): δ=1.30 (s, 18H), 1.36 (s, 18H), 3.49-3.70 (m, 16H), 4.27 (d, J=11.2 Hz, 1H), 4.28 (d, J=11.2 Hz, 1H), 5.06 (s, 2H), 6.72 (d, J=8 Hz, 2H), 6.78 (s, 1H), 6.83-6.91 (m, 12H), 7.03 (s, 1H), 7.09-7.14 (m, 4H), 7.26 (s, 1H); $^{13}C$ NMR (100 MHz, $CDCl_3$): δ=31.4, 31.6, 34.9, 34.9, 66.6, 68.7, 70.6, 73.2, 113.0, 114.4, 115.9, 117.1, 119.0, 128.1, 128.1, 128.8, 136.3, 137.3, 138.7, 138.9, 150.2, 151.2, 153.2 (one signal is missing, possibly because of signal overlap). HRMS (ESI): m/z $[M+H]^+$: $C_{61}H_{83}N_3O_9$, calcd. 1002.6208, found 1002.6233; $[M+Na]^+$: $C_{61}H_{83}N_3O_9Na$ calcd. 1024.6027, found 1024.6011.

Rotaxane 2: $^1H$ NMR (400 MHz, $CDCl_3$, 298 K): δ=1.31 (s, 18H), 1.33 (s, 18H), 3.33-3.50 (m, 4H), 3.61-3.70 (m, 8H), 4.38 (s, 4H), 4.52 (d, J=5.6 Hz, 4H), 4.56 (d, J=1.6 Hz, 4H), 4.91 (s, 2H), 6.73 (d, J=8.4 Hz, 2H), 6.86 (d, J=8.4 Hz, 2H), 7.00-7.10 (m, 9H), 7.12 (d, J=1.6 Hz, 1H), 7.18 (d, J=1.6 Hz, 2H), 7.30 (s, 2H), 7.40 (d, J=7.6 Hz, 2H), 7.46 (s, 1H), 7.57 (s, 1H), 7.63 (b, 1H), 7.76 (t, J=7.6 Hz, 1H); $^{13}$C NMR (100 MHz, CDCl$_3$, 298 K): δ=31.4, 31.5, 34.8, 34.8, 66.5, 69.0, 70.6, 70.9, 71.8, 73.0, 112.9, 113.2, 116.0, 117.1, 118.1, 120.6, 127.7, 128.2, 128.3, 128.4, 136.0, 137.4, 137.7, 137.7, 139.1, 139.2, 151.0, 151.5, 151.7, 153.7, 157.6 (one signal is missing, possibly because of signal overlapping); HR-MS (ESI): calcd for C$_{61}$H$_{87}$N$_4$O$_9$$^+$ [M+H]$^+$, m/z 1079.6468; found, m/z 1079.7648.

Rotaxane 3: $^1$H NMR (400 MHz, CD$_3$CN): δ=1.29 (s, 18H), 1.35 (s, 18H), 2.43-2.58 (m, 4H), 3.43-3.57 (m, 8H), 3.68-3.79 (m, 8H), 4.30 (s, 4H), 4.90 (s, 4H), 6.88 (d, J=8.2 Hz, 2H), 6.94 (d, J=8.0 Hz, 2H), 7.03 (d, J=8.5 Hz, 2H), 7.07-7.14 (m, 4H), 7.19-7.24 (m, 3H), 7.28-7.35 (m, 3H), 7.70 (br s, 1H); $^{13}$C NMR (100 MHz, CD$_3$CN): δ=30.1, 31.7, 31.8, 35.6, 35.6, 35.9, 69.9, 70.4, 71.6, 73.8, 113.8, 114.0, 116.5, 118.8, 128.7, 129.2, 129.3, 130.2, 136.6, 138.6, 138.6, 139.2, 140.5, 140.6, 151.7, 151.9, 152.0, 154.3 ppm (one signal is missing, possibly because of overlapping); HRMS (ESI): calcd for C$_{61}$H$_{83}$N$_3$O$_7$S$_2$Na$^+$ [M+Na]$^+$, m/z 1056.5570; found, m/z 1056.5595.

In addition, another comparative experiment was done under a condition similar to the one used in the synthesis of rotaxane 1, but without the addition of NaTFPB. The $^1$H NMR spectrum of the crude product displayed no detectable signals corresponding to rotaxane 1, which indicated that the Na$^+$ ion template is crucial for efficiently threading the urea unit through the cavity of MC1.

Example 3

Urea 3

Scheme 3

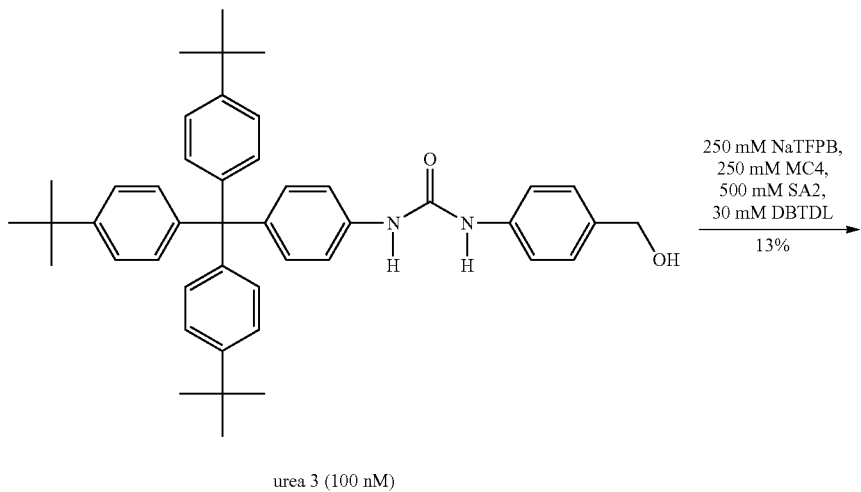

urea 3 (100 nM)

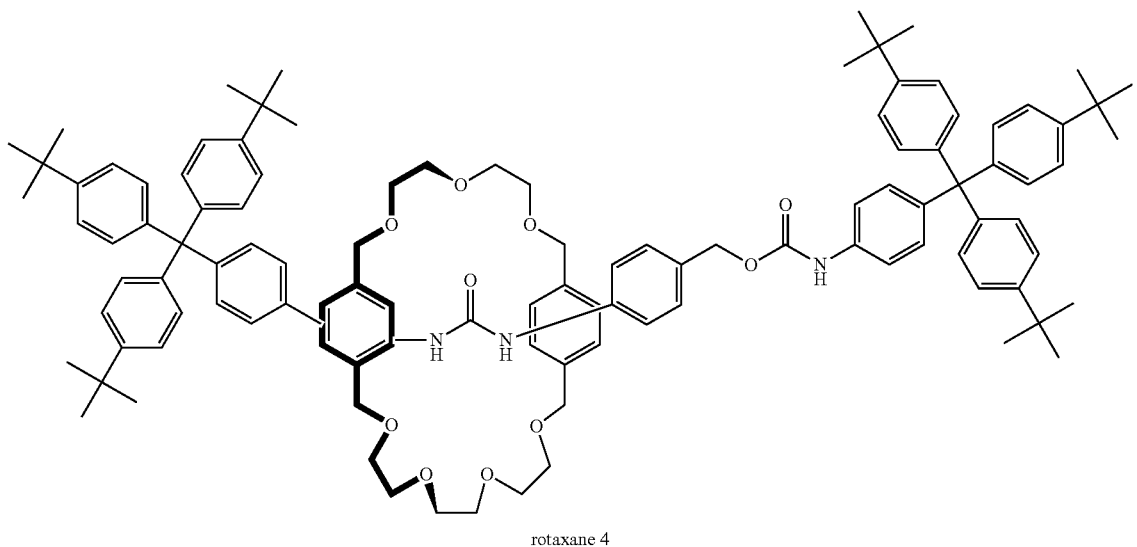

rotaxane 4

In this example, urea 3 having a urea group conjugated to two aromatic rings was used as the guest molecule and SA2 was used as the stoppering agent, because the 3,5-di-t-butylphenyl group in urea 2 and SA1 is not sterically bulky enough to prevent the dethreading of MC4. NaTFPB was used as the templating salt. DBTDL was used as a catalyst for capping the SA2 to the urea 3. For preparing the rotaxanes 4, a $CH_2Cl_2$ solution containing urea 3, NaTFPB, MC4, and DBTDL was added with SA2, and stirred at ambient temperature for 16 hours.

The macrocycle interlocked in rotaxane 4 is MC4, which different to MC1 is by replacing one of its diethylene glycol chains with a triethylene glycol one. The large terminal groups are required to prevent the dethreading of MC4. The lower yield in the synthesis of rotaxane 4 simply reflected that MC4 is a more flexible and less preorganized host for such a $Na^+$ ion templating host-guest complexation system, even it contains one more oxygen atom for the N—H groups in urea 3 to interact with. Nevertheless, with the assistance from the $Na^+$ ion template, MC4 and urea 3 still can form pseudorotaxane complexes in solution and rotaxane 4 was isolated in 13% yield.

Figure 6A:
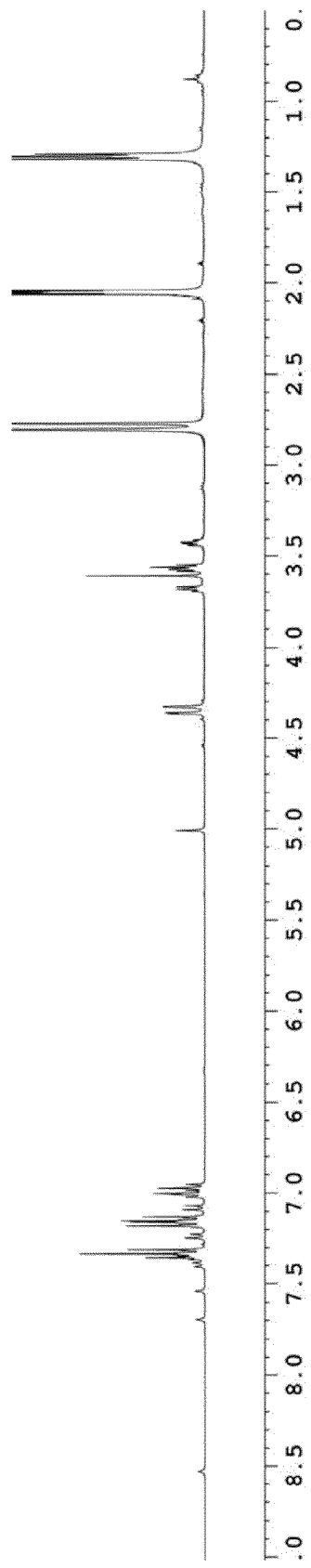
FIGS. 6A and 6B are $^1$H NMR (400 MHz, CDCl$_3$, 298 K) and $^{13}$C NMR (100 MHz, CDCl$_3$, 298 K) spectra of rotaxane 4, respectively.
Figure 6B:
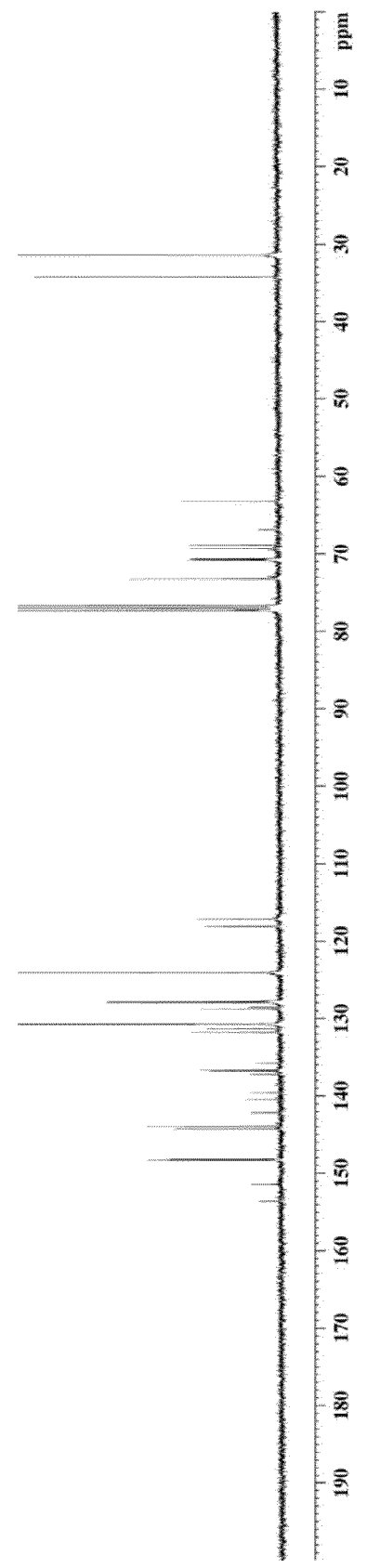

The $^1H$ NMR and $^{13}C$ NMR spectra of rotaxane 4 are shown in FIGS. 6A and 6B, respectively. All related spectral data are listed below.

Rotaxane 4: $^1H$ NMR (400 MHz, $CD_3COCD_3$): δ=1.30 (s, 27H), 1.32 (s, 27H), 3.40-3.45 (m, 4H), 3.54-3.59 (m, 8H), 3.61 (s, 4H), 3.66-3.70 (m, 4H), 4.29-4.40 (m, 8H), 5.01 (s, 2H), 6.94-7.04 (m, 10H), 7.08 (d, J=8.8 Hz, 2H), 7.11-7.20 (m, 14H), 7.24 (d, J=8.4 Hz, 2H), 7.30-7.37 (m, 14H), 7.39 (d, J=8.8 Hz, 2H), 7.54 (s, 1H), 7.70 (s, 1H), 8.53 (s, 1H); $^{13}C$ NMR (100 MHz, $CDCl_3$): δ=31.4, 31.4, 34.3, 34.3, 63.2, 66.8, 68.8, 69.3, 70.6, 70.7, 70.9, 73.2, 117.1, 118.1, 124.0, 124.0, 127.7, 127.8, 127.9, 128.6, 128.8, 130.7, 130.8, 131.3, 131.8, 135.8, 136.7, 136.8, 137.2, 139.6, 140.5, 142.2, 143.9, 144.2, 148.2, 148.3, 151.4, 153.6; HRMS (ESI): m/z $[M+Na]^+$: $C_{109}H_{131}N_3O_{10}Na$ cal. for 1664.9732, found 1664.9727.

Example 4

Urea 4

In this example, urea 4 having a urea group conjugated to one aromatic ring was used as the guest molecule. NaTFPB was used as the templating salt. MC1 was used as the host molecule. SA1 was used as the stoppering agent. For preparing the rotaxane 5, a $CH_2Cl_2$ solution containing urea 4, NaTFPB and MC1 was added SA1 and stirred at ambient temperature for 16 hours.

Scheme 4

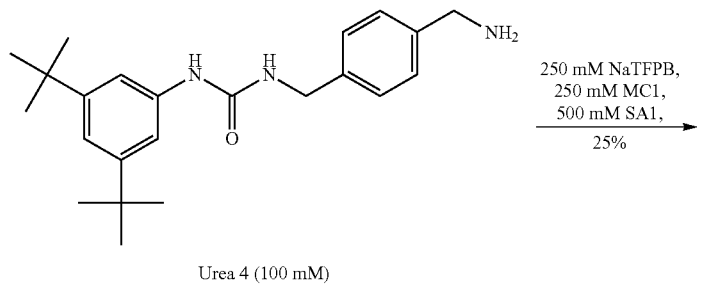

Urea 4 (100 mM)

250 mM NaTFPB,
250 mM MC1,
500 mM SA1,
25%

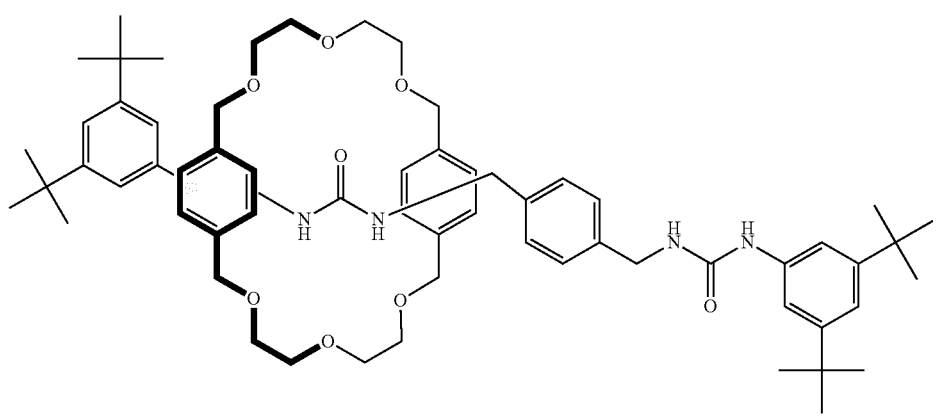

rotaxane 5

All related spectral data of rotaxane 5 are listed below.

Rotaxane 5: M.p. 120-121° C.; $^1$H NMR (400 MHz, CDCl$_3$): δ=1.34 (s, 36H), 3.50 (s, 16H), 3.60-3.70 (br, 4H), 4.30 (s, 8H), 4.74-4.82 (br, 2H), 6.66-6.71 (br, 2H), 6.84 (s, 4H), 7.06 (s, 8H), 7.10 (s, 2H), 7.27 (s, 4H); $^{13}$C NMR (100 MHz, CDCl$_3$): δ=31.6, 35.0, 43.3, 68.7, 70.6, 73.4, 114.0, 116.4, 127.1, 129.0, 136.7, 137.4, 139.0, 151.2, 155.3;

HRMS (ESI): m/z [M+H]$^+$: C$_{62}$H$_{87}$N$_4$O$_8$, calcd. 1015.6511, found 1015.6523; [M+Na]$^+$: C$_{62}$H$_{86}$N$_4$O$_8$Na calcd. 1037.6343, found 1037.6317.

Example 5

Urea 5

In this example, urea 5 having a urea group conjugated to no aromatic rings was used as the guest molecule. NaTFPB was used as the templating salt. MC1 or MC5 was used as the host molecule. SA1 was used as the stoppering agent. DBTDL was used as a catalyst for capping the SA1 to the urea 5. For preparing the rotaxanes 6 and 7, a CH$_2$Cl$_2$ solution containing urea 5, NaTFPB, one of the host molecules, and DBTDL was added with SA1 and stirred at ambient temperature for 16 hours.

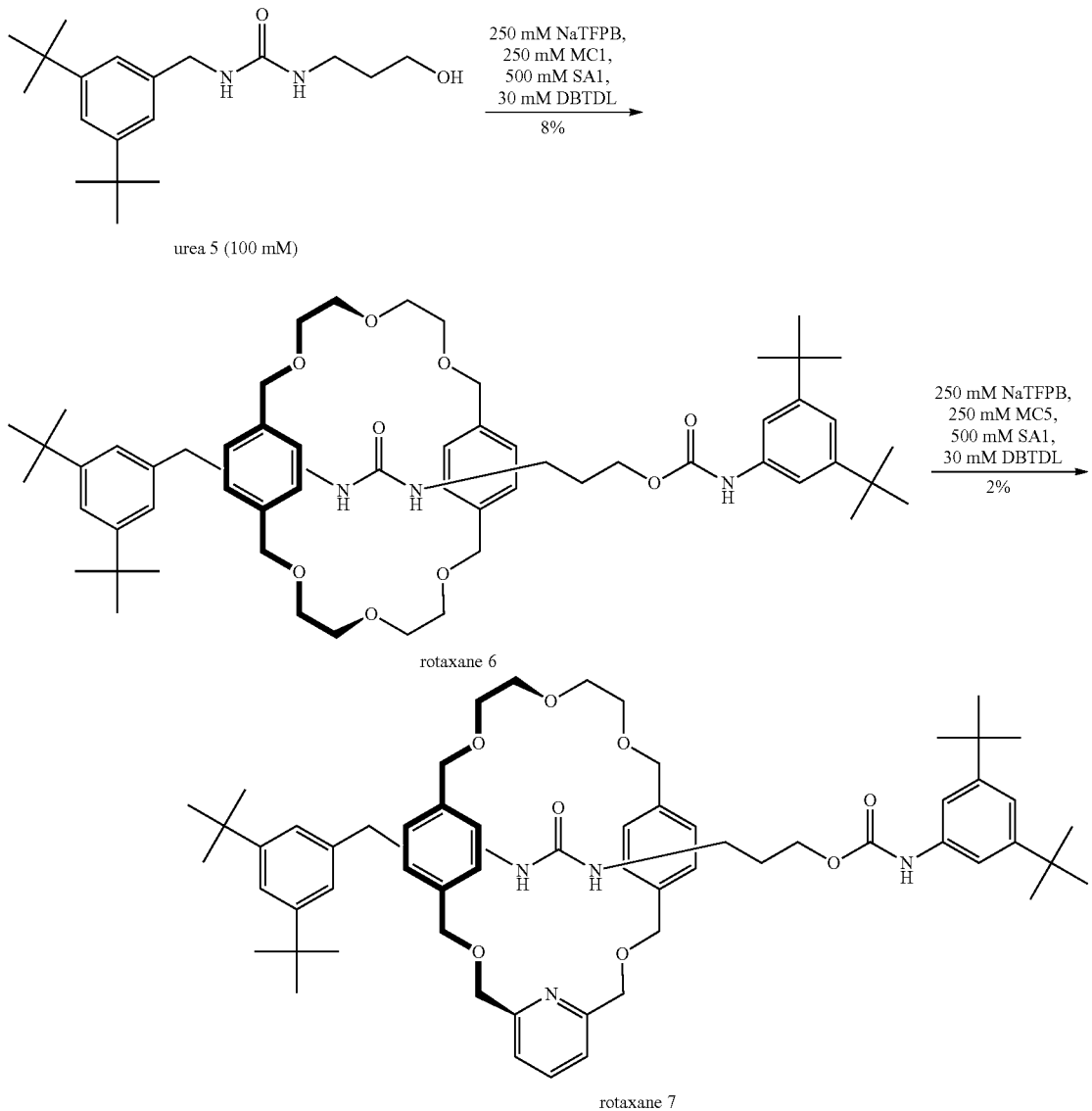

Scheme 5

Figure 7A:
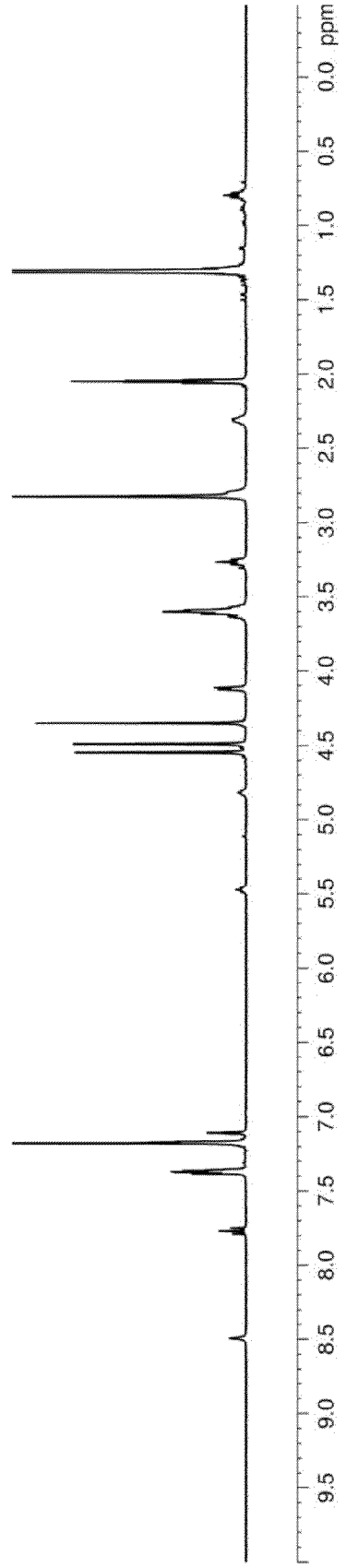
FIGS. 7A and 7B are $^1$H NMR (400 MHz, CDCl$_3$, 298 K) and $^{13}$C NMR (100 MHz, CDCl$_3$, 298 K) spectra of rotaxane 7, respectively.
Figure 7B:
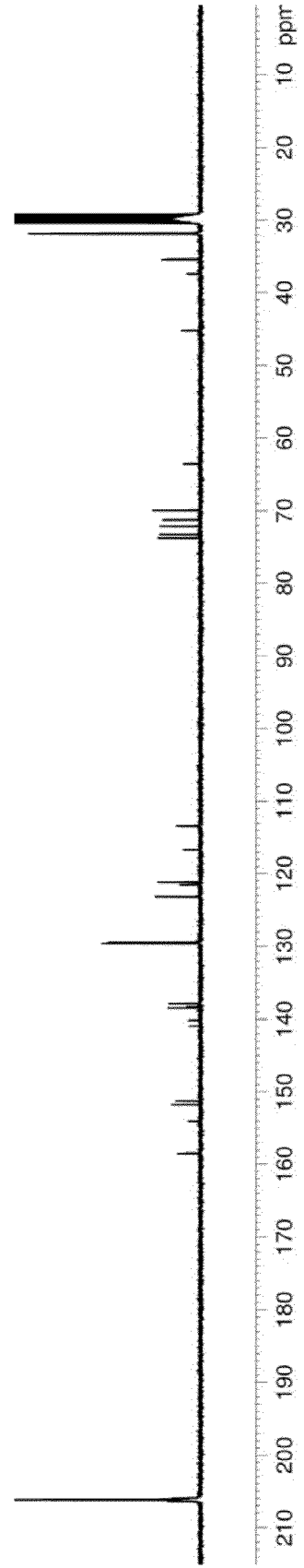

All related spectral data of rotaxane 6 and 7 are listed below. The $^1$H and $^{13}$C NMR spectra of rotaxane 7 were shown in FIGS. 7A and 7B, respectively.

Rotaxane 6: M.p. 113-114° C.; $^1$H NMR (400 MHz, CDCl$_3$): δ=0.77 (t, J=5.6 Hz, 2H), 1.32 (s, 18H), 1.34 (s, 18H), 1.92-2.00 (br, 2H), 3.19 (t, J=5.2 Hz, 2H), 3.40-3.59 (m, 16H), 4.29 (s, 8H), 4.33 (d, J=5.2 Hz, 2H), 4.40-4.46 (s, 1H), 5.29-5.34 (s, 1H), 7.07 (d, J=1.6 Hz, 1H), 7.14 (s, 8H), 7.20 (s, 2H), 7.31 (J=1.2 Hz, 1H), 7.37 (s, 2H), 7.80-7.84 (br, 1H); $^{13}$C NMR (100 MHz, CDCl$_3$): δ=27.8, 31.5, 31.5, 34.8, 34.9, 37.4, 45.2, 63.6, 68.9, 70.5, 73.5, 112.7, 116.2, 121.2, 122.8, 129.1, 137.0, 138.7, 139.1, 150.9, 151.3, 153.3, 158.0; HRMS (ESI): m/z [M+H]$^+$: $C_{58}H_{86}N_3O_9$ calcd. 968.6364, found 968.6343; [M+Na]$^+$: $C_{58}H_{85}N_3O_9Na$ calcd. 990.6184, found 990.6158.

Rotaxane 7: $^1$H NMR (400 MHz, CD$_3$COCD$_3$, 298 K): δ=0.80 (t, J=6.4 Hz, 2H), 1.30 (s, 18H), 1.31 (s, 18H), 2.27-2.35 (m, 2H), 3.27 (t, J=6.4 Hz, 2H), 3.55-3.66 (m, 8H), 4.12 (d, J=5.4 Hz, 2H), 4.35 (s, 4H), 4.52 (s, 4H), 4.55 (s, 4H), 4.82 (s, 1H), 5.47 (t, J=5.2 Hz, 1H), 7.11 (t, J=1.7 Hz, 1H), 7.16-7.19 (m, 10H), 7.35-7.40 (m, 5H), 7.77 (t, J=7.8 Hz, 1H), 8.49 (s, 1H); $^{13}$C NMR (100 MHz, CD$_3$COCD$_3$, 298 K): δ=31.8, 31.9, 35.3, 35.4, 37.4, 45.2, 63.6, 69.9, 71.2, 72.1, 73.3, 73.7 (one signal is missing possibly because of signal overlapping), 113.4, 116.7, 121.2, 121.5, 123.2, 129.4, 129.5, 137.9, 138.3, 138.5, 140.2, 140.9, 151.3, 151.8, 154.0, 158.4, 158.5; HR-MS (ESI): calcd for $C_{61}H_{84}N_4NaO_8^+$ [M+Na]$^+$, m/z 1023.6181; found, m/z 1023.6158.

The urea groups in urea 2, 4 and 5, were conjugated to two, one and zero aromatic rings, respectively. The yields of the corresponding rotaxanes 1, 5, and 6 were 40%, 25%, and 8%, respectively. This result may be explained by the acidity enhancement of the urea NH groups when conjugated to more aromatic rings, which increases the stability and concentration of the pseudorotaxanes in solution and thus, increases the synthetic efficiency of the corresponding rotaxanes.

Embodiment 2

Guest Molecule Containing a Carbamate Group

Example 6

Carbamate 1

In this example, carbamate 1 having a carbamate group conjugated to one aromatic ring by its NH motif was used as the guest molecule. NaTFPB was used as the templating salt. MC1 was used as the host molecule. SA1 was used as the stoppering agent. DBTDL was used as a catalyst for capping the SA1 to the carbamate 1. For preparing the rotaxane 8, a CH$_2$Cl$_2$ solution containing carbamate 1, NaTFPB, DBTDL and MC1 was added SA1 and stirred at ambient temperature for 16 hours.

Possibly because the conjugation to aromatic ring increases the acidity of the NH moiety of the carbamate group, pseudorotaxanes formed from carbamate 1, MC1 and NaTFPB were relatively stable in solution, and the yield of rotaxane 8 was up to 34%.

Figure 8A:
FIGS. 8A and 8B are $^1$H NMR (400 MHz, CDCl$_3$, 298 K) and $^{13}$C NMR (100 MHz, CDCl$_3$, 298 K) spectra of rotaxane 8, respectively.
Figure 8B:
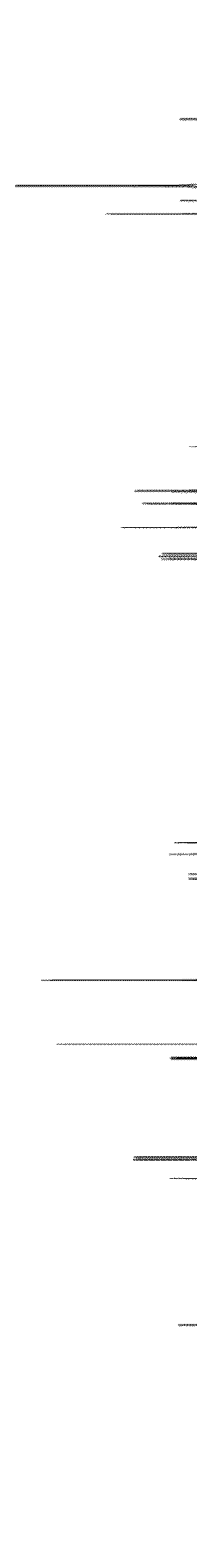

The $^1$H NMR and $^{13}$C NMR spectra of rotaxane 8 are shown in FIGS. 8A and 8B, respectively. All related spectral data are listed below.

Rotaxane 8: $^1$H NMR (400 MHz, CDCl$_3$): δ=0.69-0.75 (m, 2H), 1.15-1.21 (m, 4H), 1.37 (s, 36H), 3.18 (t, J=6 Hz, 2H), 3.56-3.70 (m, 16H), 4.32 (d, J=10.4 Hz, 4H), 4.36 (d, J=10.4 Hz, 4H), 7.10 (t, J=1.6 Hz, 1H), 7.13 (t, J=1.6 Hz, 1H), 7.17 (s, 8H), 7.42 (d, J=1.6 Hz, 2H), 7.54 (d, J=1.6 Hz, 2H), 7.85 (s, 1H), 7.98 (s, 1H); $^{13}$C NMR (100 MHz, CDCl$_3$): δ=23.3, 31.5, 31.5, 33.3, 34.9, 34.9, 63.5, 68.9, 70.5, 73.4, 112.1, 113.5, 116.0, 116.6, 129.0, 136.9, 138.5, 138.7, 150.8, 151.0, 153.3, 171.3 (one signal is missing possibly because of signal overlapping); HRMS (ESI): m/z [M+H]$^+$ $C_{58}H_{85}N_2O_{10}$ calcd. 969.6204, found 969.6185; [M+Na]$^+$: $C_{58}H_{84}N_2O_{10}Na$ calcd. 991.6024, found 991.6011.

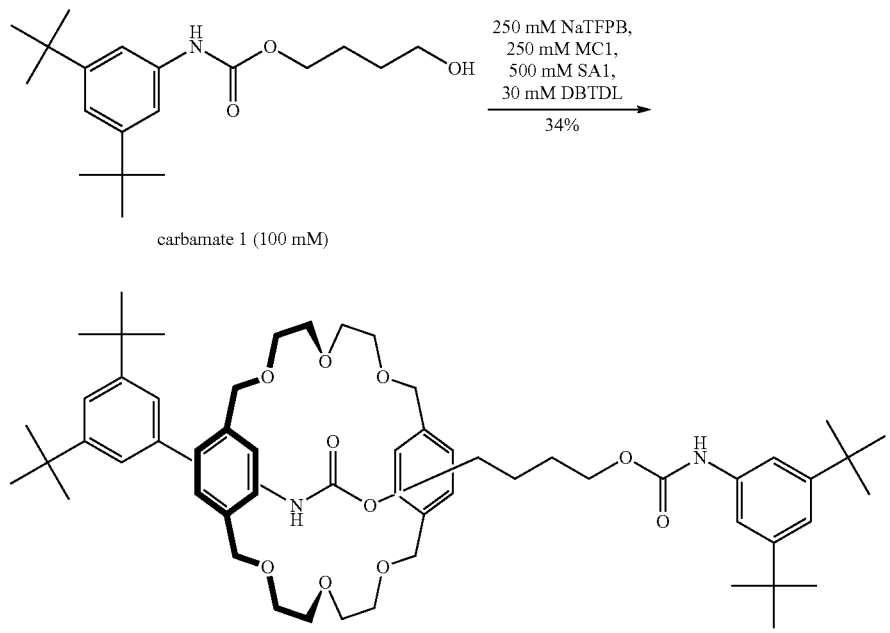

rotaxane 8

Example 7

Carbamate 2

Scheme 7

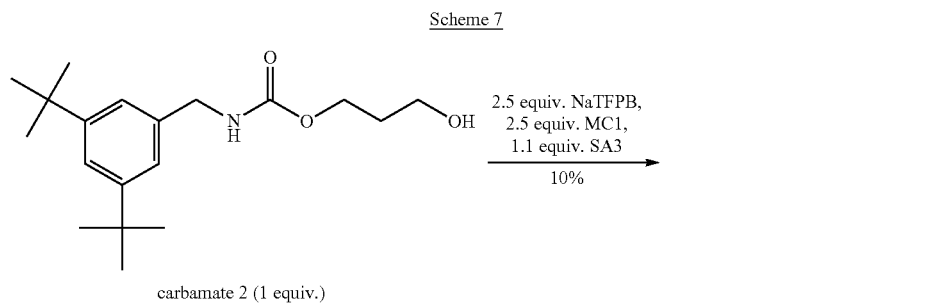

carbamate 2 (1 equiv.)

2.5 equiv. NaTFPB,
2.5 equiv. MC1,
1.1 equiv. SA3
⟶
10%

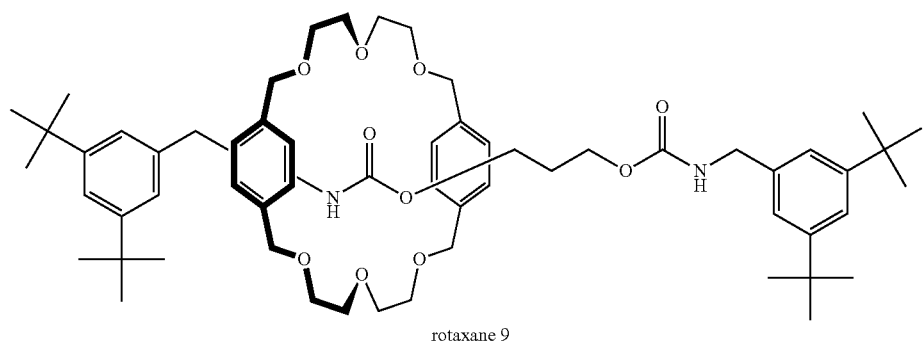

rotaxane 9

In this example, carbamate 2 having a carbamate group conjugated to no aromatic ring was used as the guest molecule. NaTFPB was used as the templating salt. MC1 was used as the host molecule. SA3 was used as the stoppering agent. For preparing the rotaxane 9, a sticky liquid obtained from concentrating a $CH_2Cl_2$ solution containing MC1, NaTFPB and carbamate 2 was added SA3 (in neat), and stirred at ambient temperature until solidified.

Since the carbamate group in carbamate 2 is not conjugated to any aromatic rings, its NH moiety in less acidic and the synthesis of rotaxane 9 is less efficient in solution. This problem was resolved by concentrating a $CH_2Cl_2$ solution mixture of MC1, NaTFPB and carbamate 2 to afford a neat mixture containing the corresponding pseudorotaxane and reacting it with SA3 under solvent-free condition. Rotaxane 9 can be isolated in 10% yield by using this approach.

All related spectral data of rotaxane 9 are listed below.

Rotaxane 9: $^1$H NMR (400 MHz, $CDCl_3$): δ=0.98-1.08 (m, 2H), 1.33 (s, 36H), 3.35 (t, J=6.8 Hz, 4H), 3.39-3.51 (m, 16H), 4.13 (d, J=2.4 Hz, 4H), 4.30 (s, 8H), 5.60 (t, J=5.6 Hz, 2H), 7.11 (s, 12H), 7.31 (s, 2H); $^{13}$C NMR (100 MHz, $CDCl_3$): δ=31.6, 34.9, 45.8, 61.6, 68.5, 70.2, 73.1, 121.2, 122.6, 128.6, 137.0, 137.6, 150.7, 156.1 (one signal is missing, possibly because of signal overlap); HRMS (ESI): m/z $[M+H]^+$ $C_{59}H_{87}N_2O_{10}$ calcd. 983.6361, found 983.6397; $[M+Na]^+$: $C_{59}H_{86}N_2O_{10}Na$ calcd. 1005.6180, found 1005.6199.

Embodiment 3

Guest Molecules Containing at Least One Amide Group

Example 8

Amide 1

Scheme 8

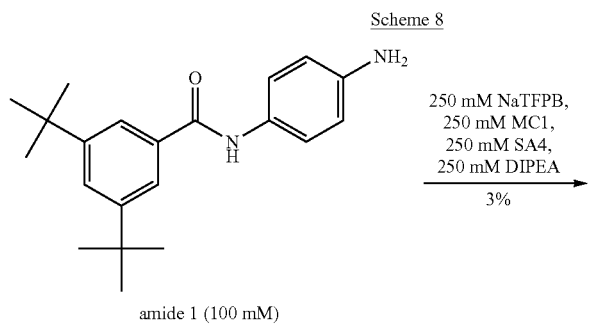

amide 1 (100 mM)

250 mM NaTFPB,
250 mM MC1,
250 mM SA4,
250 mM DIPEA
⟶
3%

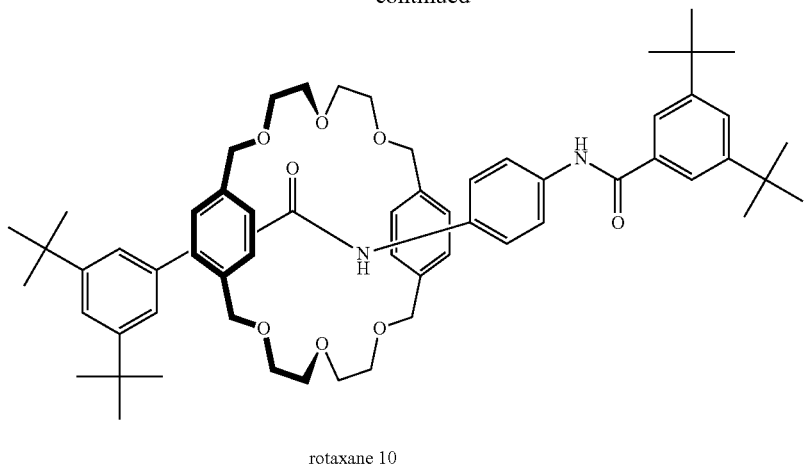

rotaxane 10

In this example, guest amide 1 has an amide group conjugated to two aromatic rings and represents a repeating unit of a para-aramid synthetic fiber, Kevlar. NaTFPB was used as the templating salt. MC1 was used as the host molecule. SA4 was used as the stoppering agent. Diisopropylethylamine (DIPEA) was used as a base to remove the HCl generated during the reaction. For preparing the rotaxane 10, a $CH_2Cl_2$ solution mixture of amide 1, NaTFPB, MC1 and DIPEA was added with SA4 and stirred at ambient temperature for 16 hours.

Due to the Kevlar polymer was synthesized by reacting monomers 1,4-phenylene-diamine and terephthaloyl chloride in solution, SA4 was chosen as the stoppering agent to react with the aniline of amide 1 to mimic the polymerization process of the Kevlar polymer. The isolation of rotaxane 10 suggested that such a $Na^+$ ion templating host-guest recognition system can be used to generate pseudorotaxanes or rotaxanes from the polymer without alternating much of its synthetic process. The low yield (3%) of rotaxane 10 can be rationalized by the release of the chloride anions during the reaction progress, which destabilized the pseudorotaxane intermediate by weakening the metal ion chelating and/or hydrogen bonding interactions among the components.

The $^1H$ NMR and $^{13}C$ NMR spectra of rotaxane 10 are shown in FIGS. 9A and 9B, respectively. All related spectral data are listed below.

Rotaxane 10: $^1H$ NMR (400 MHz, $CDCl_3$): δ=1.42 (s, 36H), 3.50-3.60 (m, 8H), 3.61-3.69 (m, 8H), 4.22 (s, 8H), 6.84 (s, 8H), 7.13 (s, 4H), 7.56 (t, J=1.6 Hz, 2H), 7.73 (d, J=1.6 Hz, 4H), 8.36 (s, 2H); $^{13}C$ NMR (100 MHz, $CDCl_3$): δ=31.5, 35.1, 69.0, 70.6, 73.4, 120.4, 121.7, 124.9, 127.9, 133.7, 136.1, 136.2, 150.7, 165.9; HRMS (ESI): m/z $[M]^+$: $C_{60}H_{80}N_2O_8$ calcd. 956.5914, found 956.5902.

Example 9

Amide 2

Scheme 9

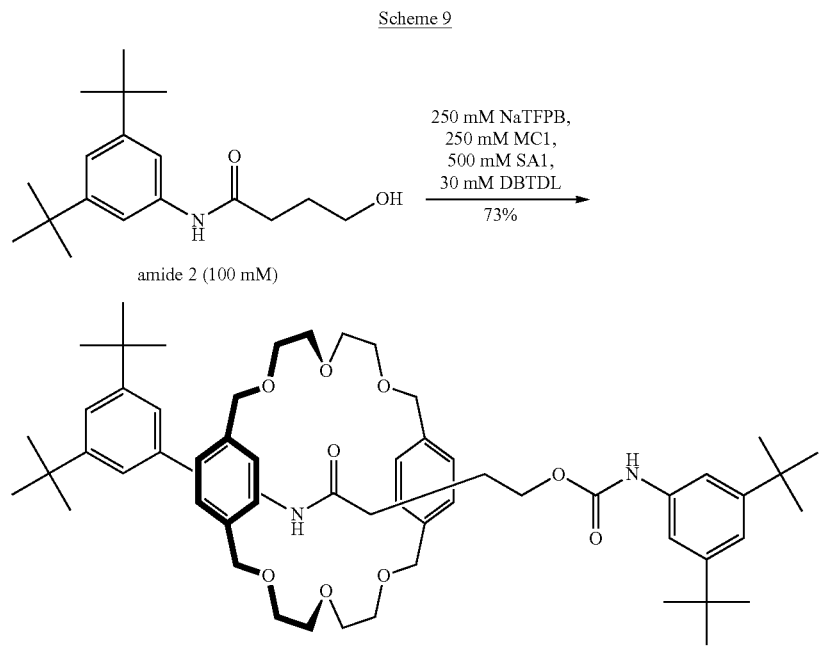

rotaxane 11

In this example, amide 2 having its NH moiety conjugated to an aromatic ring was used as the guest molecule. NaTFPB was used as the templating salt. MC1 was used as the host molecule. SA1 was used as the stoppering agent. DBTDL was used as a catalyst for capping the SA1 to the amide 2. For preparing the rotaxane 11, a CH$_2$Cl$_2$ solution containing amide 2, NaTFPB, MC1 and DBTDL was added SA1 and stirred at ambient temperature for 16 hours.

Characterization data for rotaxane 11: M.p. 176-177° C.; $^1$H NMR (400 MHz, CDCl$_3$): δ=0.70-0.76 (m, 2H), 1.17-1.21 (m, 2H), 1.37 (s, 36H), 3.18 (t, J=6 Hz, 2H), 3.58-3.70 (m, 16H), 4.33 (d, J=10.4 Hz, 4H), 4.36 (d, J=10.4 Hz, 4H), 7.10 (t, J=1.6 Hz, 1H), 7.13 (t, J=1.6 Hz, 1H), 7.17 (s, 8H), 7.42 (d, J=1.6 Hz, 2H), 7.54 (d, J=1.6 Hz, 2H), 7.83-7.88 (br, 1H), 7.97-8.00 (br, 1H); $^{13}$C NMR (100 MHz, CDCl$_3$): δ=23.2, 31.5, 31.5, 33.3, 34.9, 34.9, 63.5, 68.9, 70.5, 73.4, 112.1, 113.5, 116.0, 116.6, 129.0, 136.9, 138.5, 138.7, 150.8, 151.0, 153.3, 171.3; HRMS (ESI): m/z [M+H]$^+$: C$_{57}$H$_{83}$N$_2$O$_9$ calcd. 939.6099, found 939.6062.

Example 10

Amide 3

In this example, amide 3 having its carbonyl moiety conjugated to an aromatic ring was used as the guest molecule. NaTFPB was used as the templating salt. MC1 was used as the host molecule. SA1 or SA5 was used as the stoppering agent. DBTDL was used as a catalyst for capping the SA1 to the amide 3. For preparing the rotaxane 12 or 13, a CH$_2$Cl$_2$ solution containing amide 3, NaTFPB, MC1 and DBTDL was added SA1 or SA5, and stirred at ambient temperature for 16 hours.

The amide groups in amides 2 and 3 have their N—H and carbonyl motif attached directly to the aromatic ring, respectively. The higher yield in the synthesis of rotaxane 11 compared to the one of rotaxane 12 is likely to because of the aromatic conjugation, which makes the NH proton in amide 2 more acidic than the one in amide 3 and thus, enhanced its complexation to MC1.

The successful synthesis of rotaxane 13 by using SA5 as the stoppering reagent, eliminates the possibility that threading the carbonyl group of SA1 into the cavity of the macrocycle in the presence of a templating Na$^+$ ion is the key intermediate in the syntheses of rotaxanes 1-12 and confirms the formation of the pseudorotaxane structure based on the

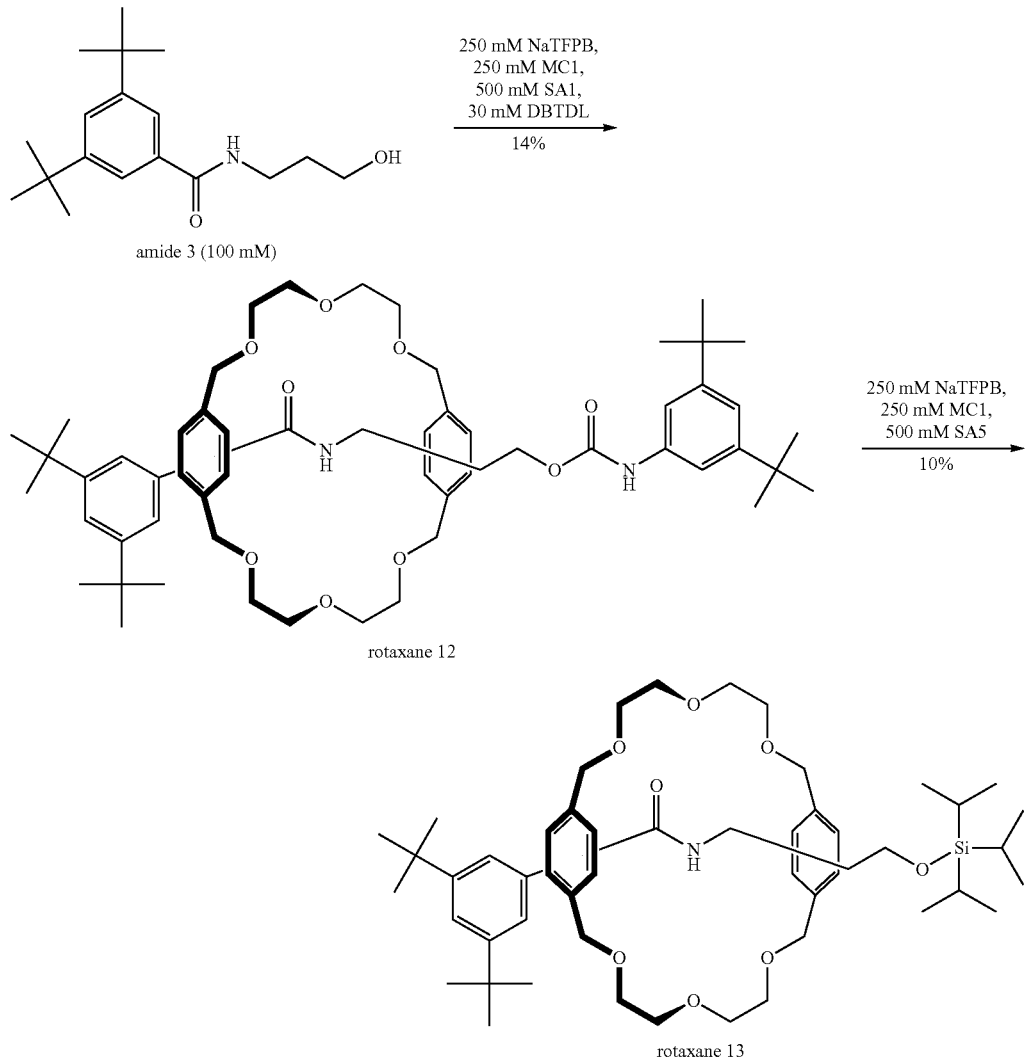

Scheme 10 recognition of MC1 and the guest units through a templating Na⁺ ion in solution. The relative low yield (10%) in the synthesis of rotaxane 13 compared to the one of rotaxane 12, can be rationalized by the release of triflate anions during the reaction progress, which destabilized the corresponding pseudorotaxanes by weakening the metal ion chelating and/or hydrogen bonding interactions among the components.

Figure 10A:
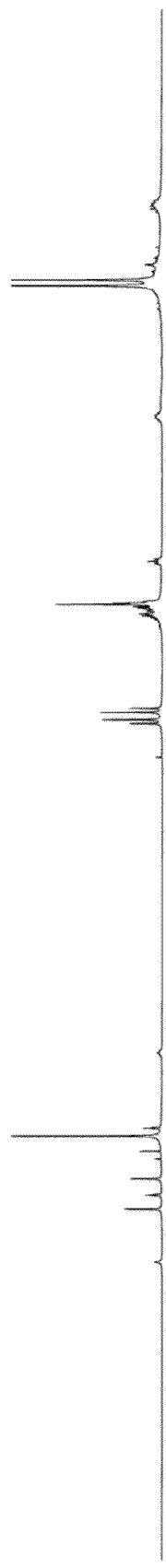
FIGS. 10A and 10B are $^1$H NMR (400 MHz, CDCl$_3$, 298 K) and $^{13}$C NMR (100 MHz, CDCl$_3$, 298 K) spectra of rotaxane 12, respectively.
Figure 10B:
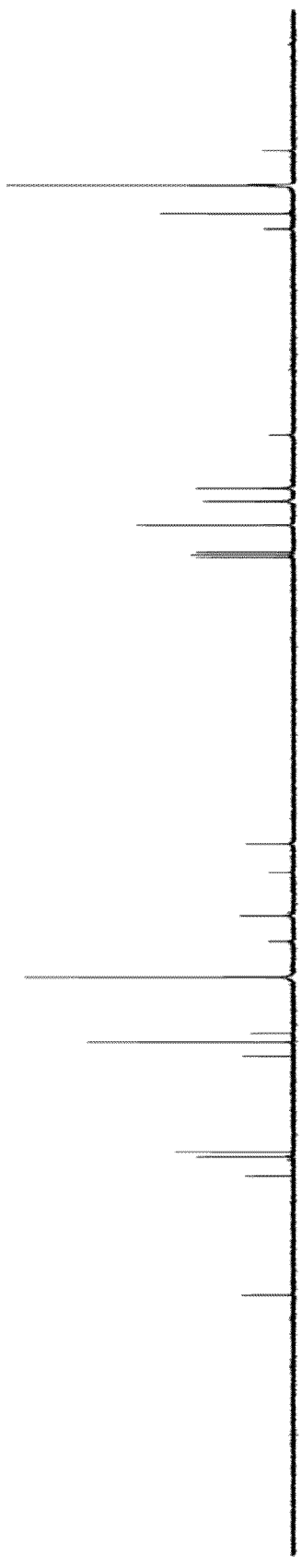

All related spectral data of rotaxane 12 and 13 are listed below. The $^1$H NMR and $^{13}$C NMR spectra of rotaxane 12 are shown in FIGS. 10A and 10B, respectively.

Rotaxane 12: $^1$H NMR (400 MHz, CDCl$_3$): δ=0.80-0.90 (m, 2H), 1.36 (s, 18H), 1.40 (18H), 2.25-2.31 (m, 2H), 3.26 (t, J=6 Hz, 2H), 3.50-3.70 (m, 16H), 4.26 (d, J=10.8 Hz, 4H), 4.34 (d, J=10.8 Hz, 4H), 6.55-6.60 (br, 1H), 7.08 (t, J=1.6 Hz, 1H), 7.14 (s, 8H), 7.43 (d, J=1.6 Hz, 2H), 7.54 (t, J=1.6 Hz, 1H), 7.63 (d, J=1.6 Hz, 2H), 7.97-8.00 (br, 1H); $^{13}$C NMR (100 MHz, CDCl$_3$): δ=27.2, 31.6, 35.0, 35.0, 36.9, 62.2, 68.8, 70.4, 73.3, 112.5, 116.0, 121.3, 124.5, 128.9, 135.7, 136.9, 138.6, 150.4, 151.0, 153.4, 168.0 (one signal is missing, possibly because of signal overlapping); HRMS (ESI): m/z [M+H]⁺: C$_{57}$H$_{83}$N$_2$O$_9$ calcd. 939.6099, found 939.6126; [M+Na]⁺: C$_{57}$H$_{82}$N$_2$O$_9$Na calcd. 961.5918, found 961.5944.

Rotaxane 13: $^1$H NMR (400 MHz, CDCl$_3$): δ=0.65-0.75 (m, 2H), 1.04-1.15 (m, 23H), 1.39 (18H), 3.09 (t, J=6.4 Hz, 2H), 3.50-3.70 (m, 16H), 4.24 (d, J=10.8 Hz, 4H), 4.34 (d, J=10.8 Hz, 4H), 7.02-7.10 (m, 9H), 7.55 (d, J=1.6 Hz, 2H), 7.90 (s, 1H); $^{13}$C NMR (100 MHz, CDCl$_3$): δ=12.1, 18.3, 26.6, 31.8, 32.8, 35.1, 63.5, 68.8, 70.6, 73.2, 113.9, 115.7, 128.6, 136.9, 139.4, 150.4, 170.2; HRMS (ESI): m/z [M+Na]⁺: C$_{51}$H$_{81}$NO$_8$SiNa calcd. 886.5629, found 886.5657.

Example 11

Amide 4 Containing One Glycine Residue

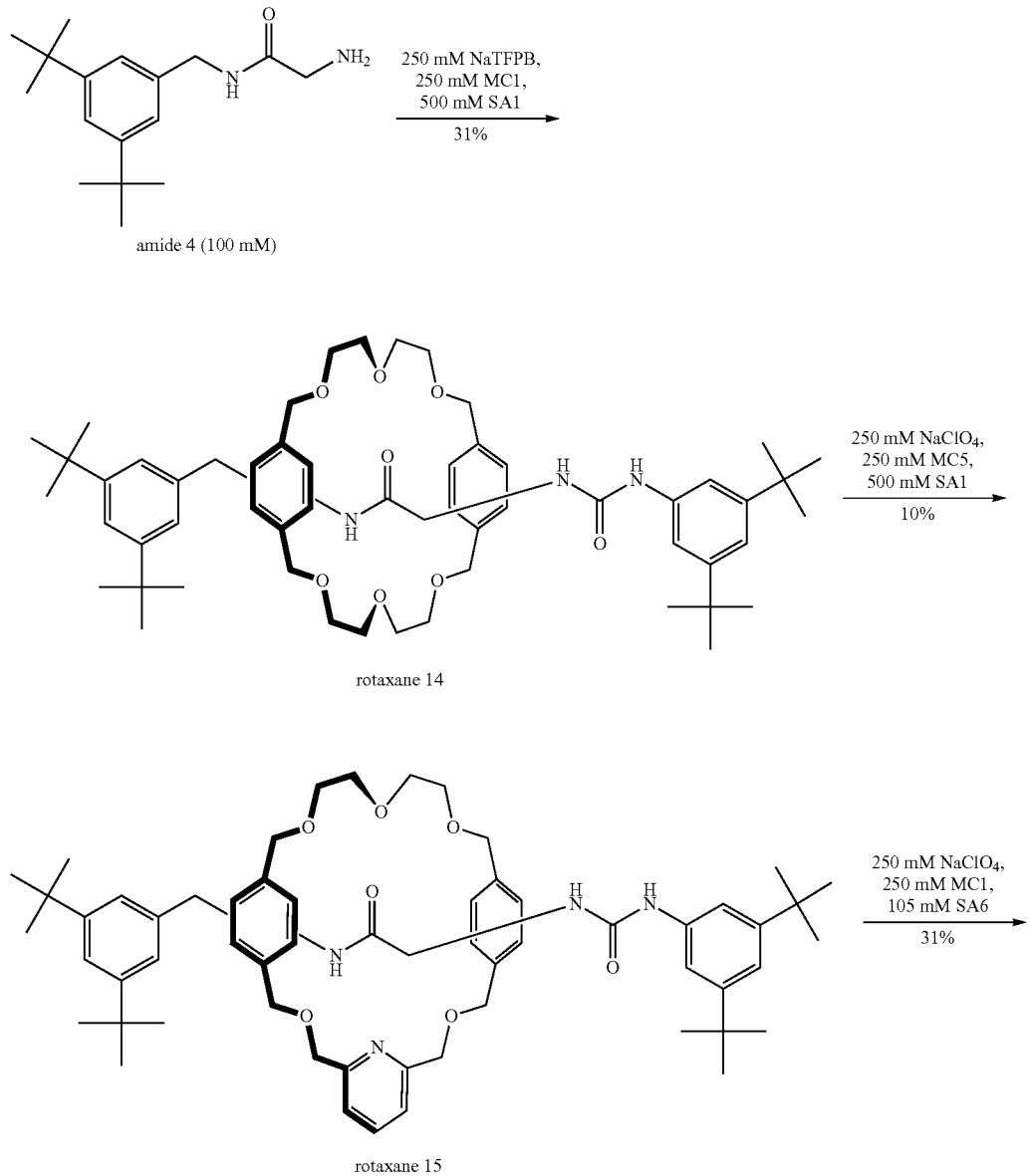

Scheme 11

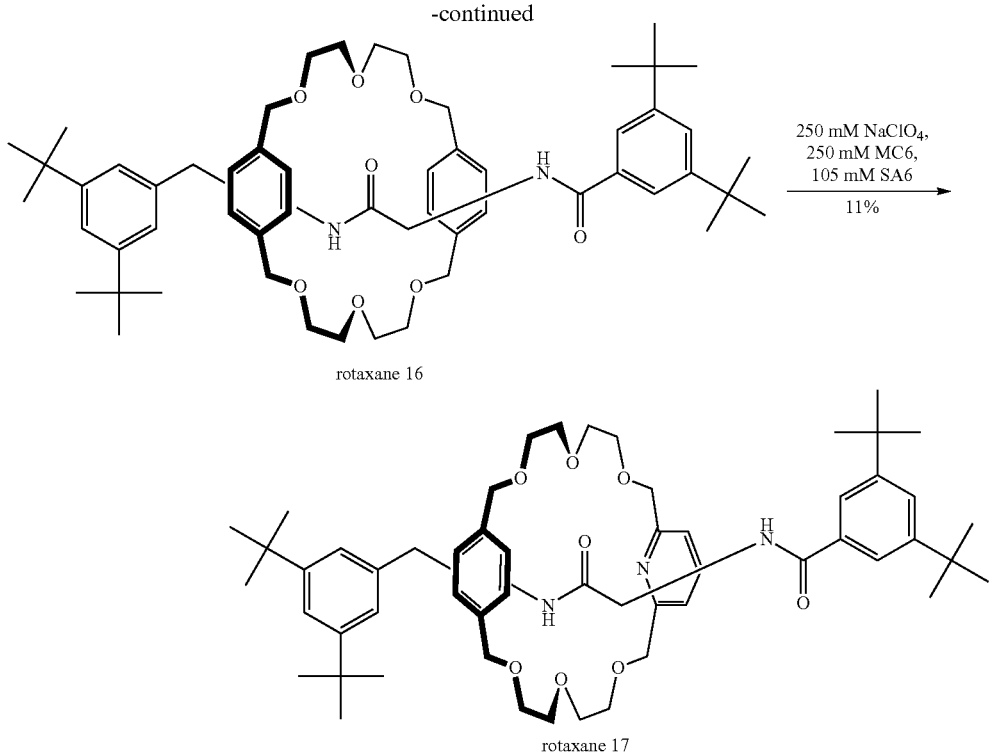

rotaxane 16 rotaxane 17

In this example, amide 4 containing one C-amidated glycine moiety and having an amide group conjugated to no aromatic rings was used as the guest molecule. NaTFPB or NaClO$_4$ was used as the templating salt. MC1, MC5, or MC6 was used as the host molecule. SA1 or SA6 was used as the stoppering agent. For preparing the rotaxanes 14-17, a CH$_2$Cl$_2$ solution containing amide 4, the macrocyclic host and the templating salt was added the stoppering agent and stirred at ambient temperature for 16 hours.

From the result above, it can be seen that even though the amide moiety is not directly linking to any aromatic rings, threading of a single amide unit through the cavity of a macrocyclic molecule in the presence of a templating Na$^+$ ion is still feasible. Using SA6 as the stoppering reagent, rotaxane 16 and 17 can still be synthesized in reasonable yields. This result suggested that no additional functionality will need to be introduced into the main chain structure of the peptide (unlike the urea moiety found in rotaxane 14), thereby allowing this recognition system to be used for constructing interlocked or interwoven structures featuring pure peptide chains. The successful syntheses of rotaxanes 14-17 also suggested that counter anion for the Na$^+$ ion template is not only limited to TFPB, other weakly ion-pairing anions, such as ClO$_4^-$ can also be used. Moreover, the above results suggested that the recognition of the host molecules above required only one single amide functionality, thereby potentially allowing higher-order [n]rotaxanes to be prepared from relatively long peptides.

When LiTFPB and KTFPB were used in place of NaTFPB in the synthesis of rotaxane 15 under similar conditions, the yield of the [2]rotaxane dropped to 9% and 4%, respectively, suggesting that Li$^+$ and K$^+$ ions are also qualified templates in such a recognition system but just not as good as Na$^+$ ions.

Figure 12A:
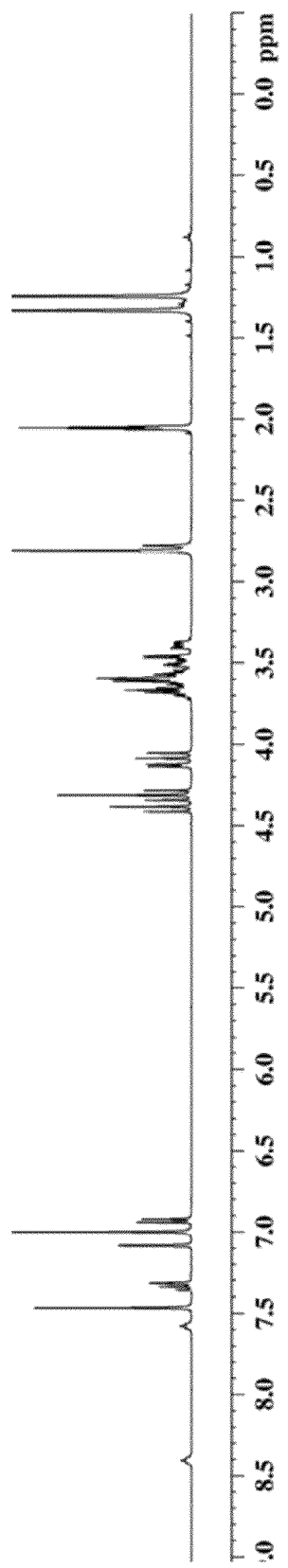
FIGS. 12A and 12B are $^1$H NMR (400 MHz, CD$_3$COCD$_3$, 298 K) and $^{13}$C NMR (100 MHz, CD$_3$COCD$_3$, 298 K) spectra of rotaxane 17, respectively.
Figure 12B:
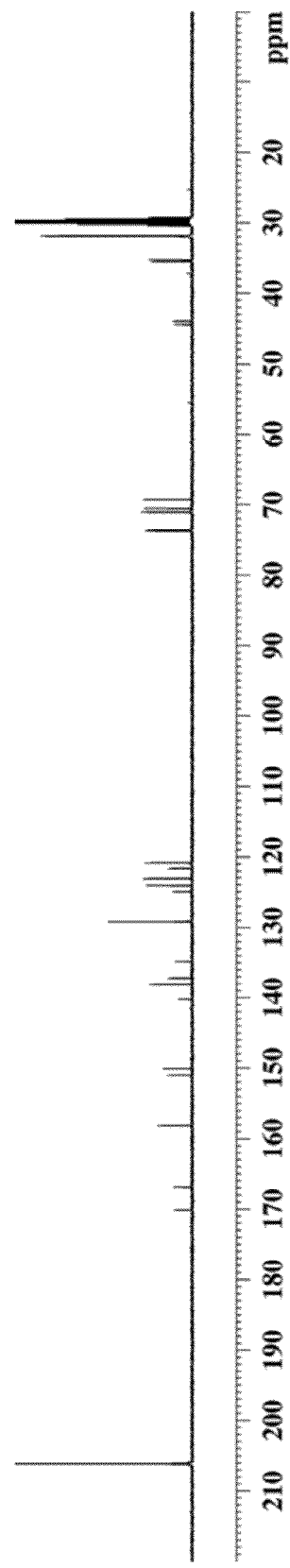

All related spectral data of rotaxane 14-17 are listed below. The $^1$H NMR and $^{13}$C NMR spectra of rotaxane 14 and 17 are shown in FIGS. 11 and 12, respectively.

Figure 13:
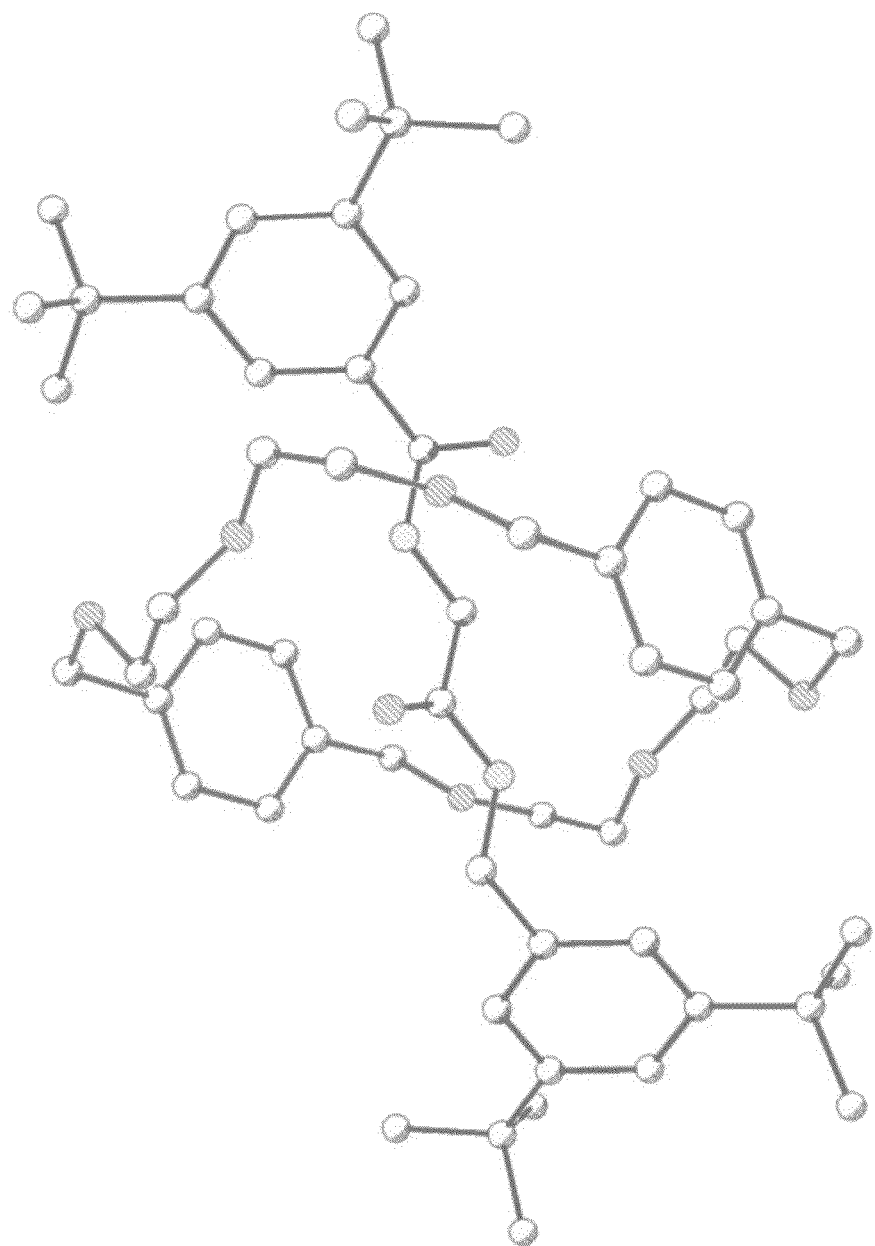
FIG. 13 is the solid state structure of rotaxane 16, respectively.

The solid state structure of rotaxane 16 is shown in FIG. 13. Single crystals suitable for X-ray crystallography were grew through liquid diffusion of hexane into a CH$_2$Cl$_2$ solution of rotaxane 16. The solid state structure of rotaxane 16 reveals the expected geometry, in which the amide group of the threadlike component penetrated MC1 and had its NH proton hydrogen bonding to the oxygen atoms of the ethylene glycol chain of MC1.

Rotaxane 14: M.p. 152-153° C.; $^1$H NMR (400 MHz, CDCl$_3$): δ=1.36 (s, 18H), 1.36 (s, 18H), 2.35 (d, J=3.6 Hz, 2H), 3.48-3.62 (m, 16H), 4.21 (d, J=5.6 Hz, 2H), 4.28 (d, J=10.8 Hz, 4H), 4.29 (d, J=10.8 Hz, 4H), 4.80-4.83 (t, J=3.6 Hz, 1H), 6.60-6.65 (br, 1H), 7.00 (t, J=1.6 Hz, 1H), 7.10 (s, 8H), 7.19 (d, J=2 Hz, 2H), 7.35 (t, J=1.6 Hz, 1H), 7.40 (d, J=2 Hz, 2H), 7.55 (s, 1H); $^{13}$C NMR (100 MHz, CDCl$_3$): δ=31.6, 31.7, 34.9, 35.0, 41.7, 44.2, 68.8, 70.4, 73.3, 112.4, 114.8, 121.4, 123.5, 128.5, 136.6, 137.6, 140.3, 150.6, 150.7, 153.9, 168.1; HRMS (ESI): m/z [M+H]$^+$: C$_{56}$H$_{82}$N$_3$O$_8$ calcd. 924.6102, found 924.6133; [M+Na]$^+$: C$_{56}$H$_{81}$N$_3$O$_8$Na calcd. 946.5921, found 946.5948.

Rotaxane 15: $^1$H NMR (400 MHz, CDCl$_3$): δ=1.26 (s, 18H), 1.28 (s, 18H), 2.45 (d, J=2.4 Hz, 2H), 3.49-3.68 (m, 8H), 4.19 (d, J=4.8 Hz, 2H), 4.25 (d, J=10.8 Hz, 2H), 4.29 (d, J=10.8 Hz, 2H), 4.36 (s, 4H), 4.44 (d, J=11.6 Hz, 2H), 4.50 (d, J=11.6 Hz, 2H), 5.30 (s, 1H), 6.96 (s, 1H), 7.12 (s, 10H), 7.22-7.32 (m, 4H), 7.50 (s, 1H), 7.67 (t, J=8 Hz, 1H), 8.09 (s, 1H); $^{13}$C NMR (100 MHz, CDCl$_3$): δ=31.4, 31.5, 34.7, 34.8, 41.6, 44.1, 69.1, 70.6, 71.1, 72.6, 73.3, 112.3, 114.7, 120.4, 121.4, 123.6, 128.5, 128.6, 136.3, 136.9, 137.4, 137.5, 140.5, 150.7, 150.8, 154.3, 157.4, 167.8; HRMS (ESI): m/z [M+H]$^+$: C$_{59}$F$_{81}$N$_4$O$_7$ cal. for 957.6105, found 957.6077; [M+Na]$^+$: C$_{59}$H$_{80}$N$_4$O$_7$Na cal. for 979.5925, found 979.5911.

Rotaxane 16: M.p. 150-151° C.; $^1$H NMR (400 MHz, CDCl$_3$): δ=1.34 (s, 18H), 1.39 (s, 18H), 3.04 (d, J=5.2 Hz, 2H), 3.38-3.50 (m, 16H), 3.79 (d, J=5.2 Hz, 2H), 4.27 (d, J=10.8 Hz, 4H), 4.31 (d, J=10.8 Hz, 4H), 6.68-6.71 (br, 1H), 6.90-6.96 (br, 1H), 7.08 (d, J=1.6 Hz, 2H), 7.11 (s, 8H), 7.30 (t, J=1.6 Hz, 1H), 7.51 (t, J=1.6 Hz, 1H), 7.57 (d, J=1.6 Hz, 2H); $^{13}$C NMR (100 MHz, CDCl$_3$): δ=31.5, 31.6, 34.8, 35.0, 42.8, 43.7, 68.8, 70.3, 73.2, 121.0, 121.8, 123.4, 124.6, 128.7, 134.8, 136.8, 137.7, 150.1, 150.2, 167.5 (one signal is missing, possibly because of signal overlapping); HRMS (ESI): m/z [M+H]$^+$: C$_{56}$H$_{81}$N$_2$O$_8$ calcd. 909.5993, found 909.6069; [M+Na]$^+$: C$_{56}$H$_{80}$N$_2$O$_8$Na calcd. 931.5812, found 931.5808.

Rotaxane 17: $^1$H NMR (400 MHz, CD$_3$COCD$_3$): δ=1.24 (s, 18H), 1.33 (s, 18H), 3.35-3.42 (m, 2H), 3.43-3.73 (m, 16H), 4.07 (d, J=12.4 Hz, 2H), 4.13 (d, J=5.6 Hz, 2H), 4.27-4.35 (m, 4H), 4.40 (d, J=11.2 Hz, 2H), 6.93 (d, J=7.6 Hz, 2H), 7.00 (s, 4H), 7.08 (d, J=1.6 Hz, 2H), 7.30-7.36 (m, 2H), 7.47 (s, 3H), 7.58 (t, J=5.6 Hz, 1H), 8.40 (d, J=5.8 Hz, 1H); $^{13}$C NMR (100 MHz, CD$_3$COCD$_3$): δ=31.8, 31.9, 35.2, 35.4, 43.9, 44.4, 69.3, 70.5, 71.0, 71.0, 73.5, 73.7, 120.8, 121.6, 123.1, 124.1, 124.9, 129.2, 134.8, 137.2, 138.1, 140.2, 150.0, 151.0, 158.1, 166.9, 170.1; HRMS (ESI): m/z [M+H]$^+$: C$_{55}$H$_{80}$N$_3$O$_8$ calcd. 910.5945, found 910.5978; [M+Na]$^+$ C$_{55}$H$_{79}$NaN$_3$O$_8$ calcd. 932.5764, found 932.5791.

Example 12

Amide 5 Containing Three Glycine Residues

In this example, amide 5 containing three glycine residues was used as the guest molecule. The template ion, the host molecule, and the stoppering agent were NaClO$_4$, MC1, and SA6, respectively. For preparing the [2]rotaxane 18 and the [3]rotaxane 19, a CH$_2$Cl$_2$ solution containing amide 5, NaClO$_4$, and MC1 was added with SA6, and stirred at ambient temperature for 16 hours.

Amide 6 has three amide units presented in its gly-gly-gly backbone for the binding of MC1. The isolation of [3]rotaxane 19 suggested that the three amide units in amide 5 can, at least, accommodate two MC1 hosts in the same time. This result demonstrates the potential application of this recognition system in the assembly of interlocked structures from peptides and other amide bond containing bio- or artificial (macro)molecules.

Figures 14A, 14B:
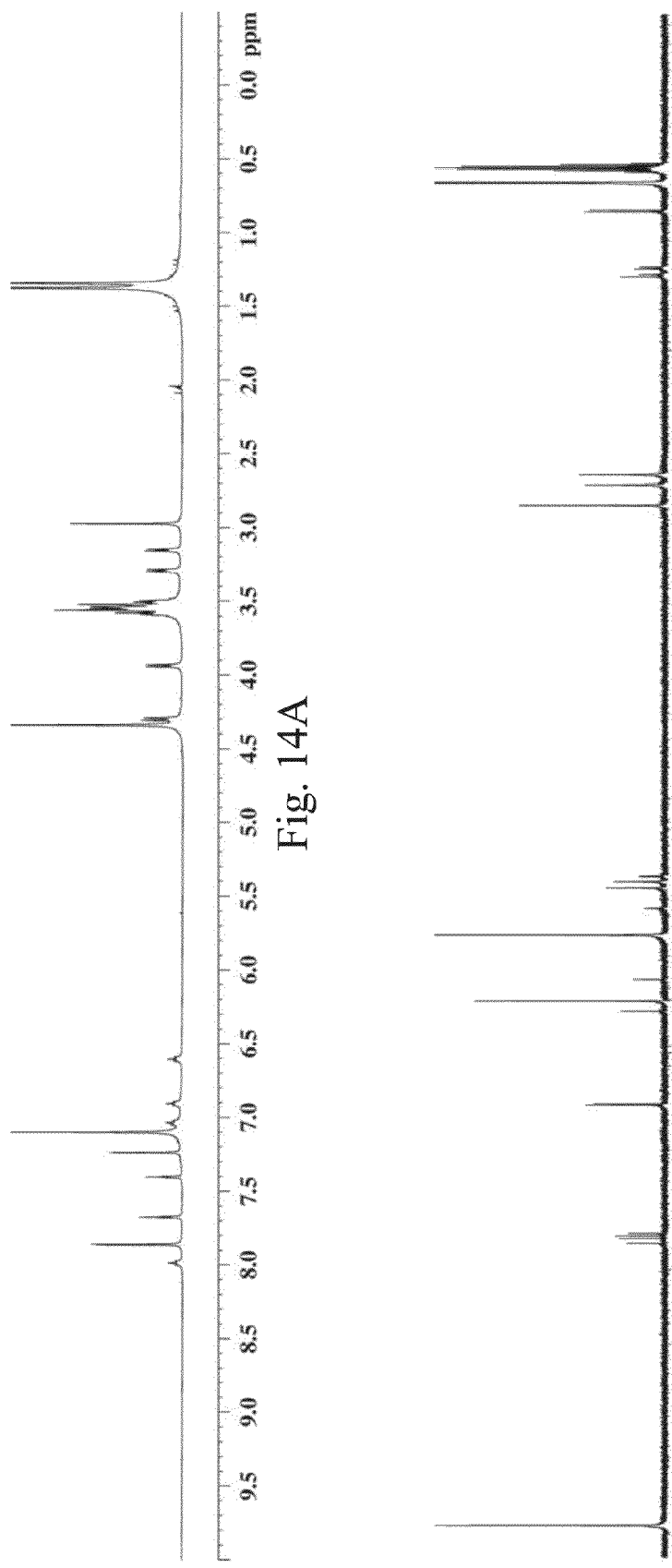
FIGS. 14A and 14B are $^1$H NMR (400 MHz, CD$_3$COCD$_3$, 298 K) and $^{13}$C NMR (100 MHz, CD$_3$COCD$_3$, 298 K) spectra of rotaxane 18, respectively.
Figure 15A:
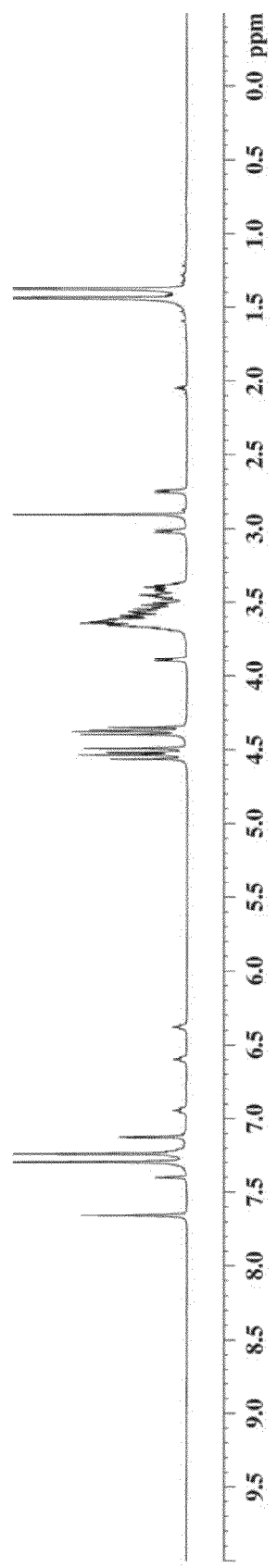
FIGS. 15A and 15B are $^1$H NMR (400 MHz, CD$_3$COCD$_3$, 298 K) and $^{13}$C NMR (100 MHz, CD$_3$COCD$_3$, 298 K) spectra of rotaxane 19, respectively.
Figure 15B:
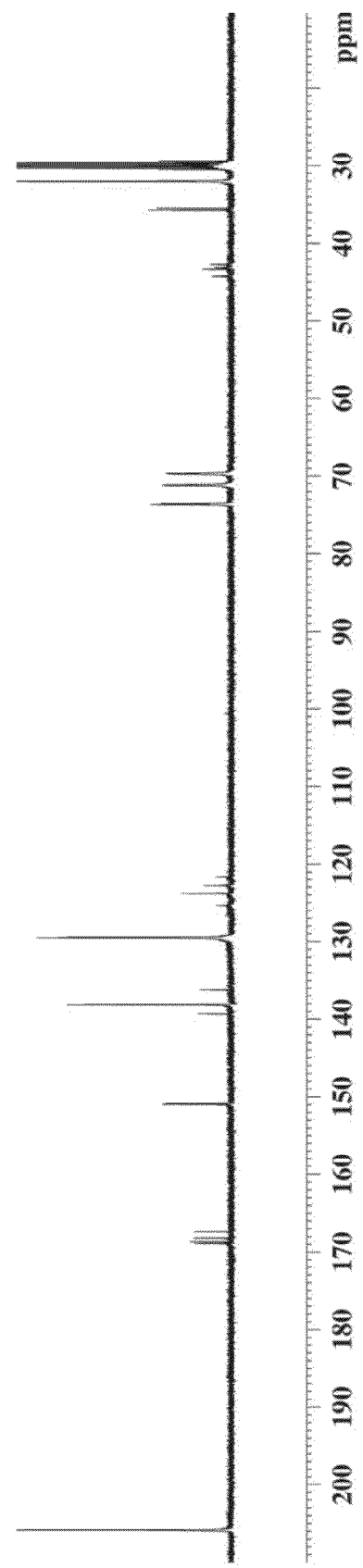

The $^1$H NMR and $^{13}$C NMR spectra of rotaxane 18 and 19 are shown in FIGS. 14 and 15, respectively. All related spectral data are listed below.

[2]Rotaxane 18: $^1$H NMR (400 MHz, CD$_3$COCD$_3$): δ=1.34 (s, 18H), 1.38 (s, 18H), 3.15 (d, J=5.6 Hz, 2H), 3.29 (d, J=4.8 Hz, 2H), 3.49-3.61 (m, 16H), 3.94 (d, J=5.6 Hz, 2H), 4.30 (d, J=5.6 Hz, 2H), 4.34 (s, 8 H), 6.60 (t, J=5.2 Hz, 1H), 6.91 (t, J=4.8 Hz, 1H), 7.04 (t, J=5.2 Hz, 1H), 7.10 (s, 8H), 7.24 (d, J=2 Hz, 2H), 7.40 (t, J=2 Hz, 1H), 7.67 (t, J=2 Hz, 1 H), 7.86 (d, J=2 Hz, 2H), 7.99 (t, J=5.6 Hz, 1H); $^{13}$C NMR

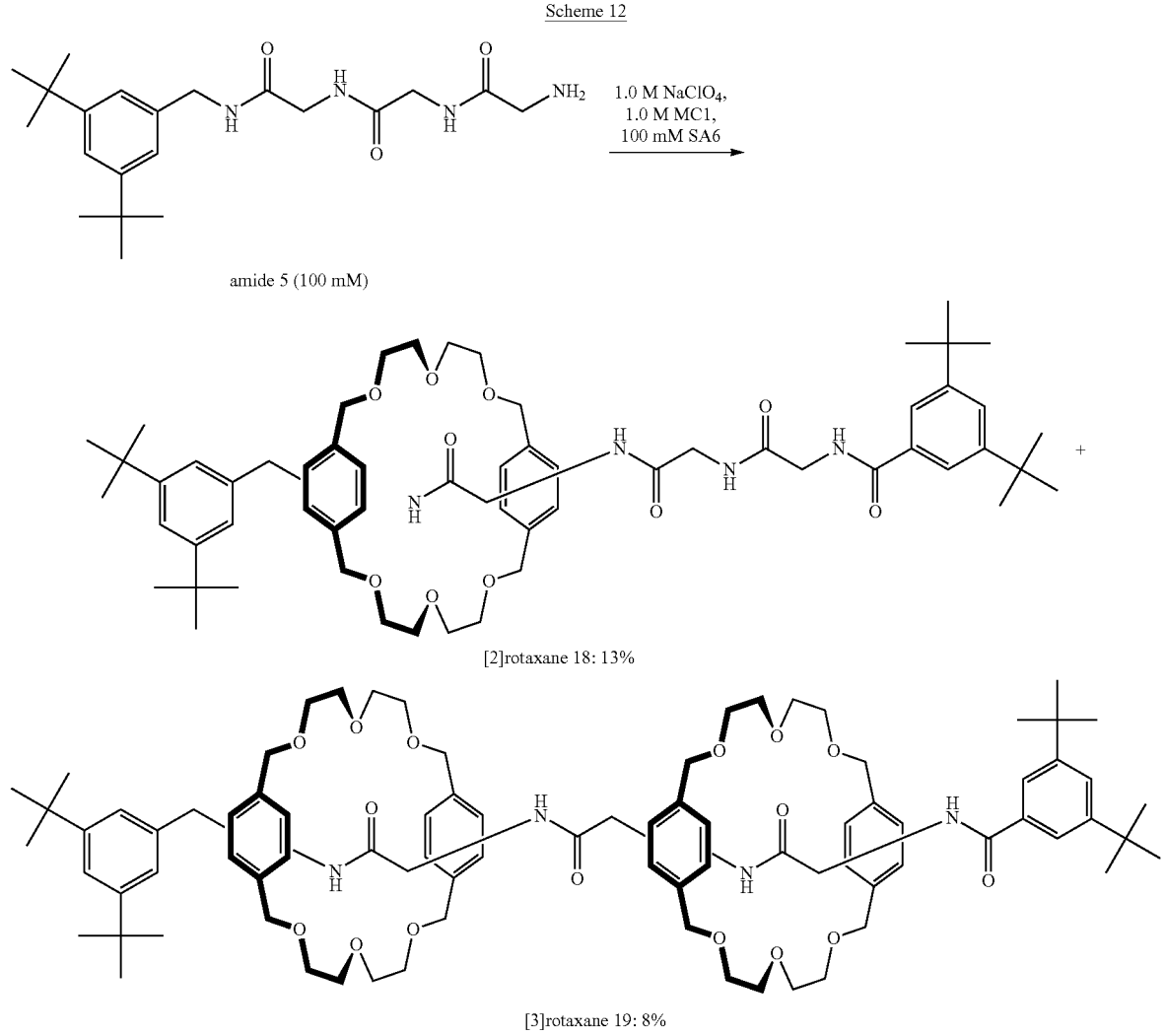

Scheme 12 amide 5 (100 mM)

1.0 M NaClO$_4$,
1.0 M MC1,
100 mM SA6

[2]rotaxane 18: 13%

[3]rotaxane 19: 8%

(100 MHz, CD$_3$COCD$_3$): δ=31.8, 31.9, 35.4, 35.6, 42.8, 43.0, 43.8, 44.1, 69.7, 71.0, 73.6, 121.8, 122.4, 123.2, 125.9, 129.3, 135.0, 137.9, 139.2, 151.2, 151.3, 168.0, 168.3, 168.7, 169.3; HRMS (ESI): m/z [M+H]$^+$: C$_{60}$H$_{87}$N$_4$O$_{10}$ calcd. 1023.6422, found 1023.6401; [M+Na]$^+$: C$_{60}$H$_{86}$N$_4$O$_{10}$Na calcd. 1045.6242, found 1045.6211.

[3]Rotaxane 19: $^1$H NMR (400 MHz, CD$_3$COCD$_3$): δ=1.38 (s, 18H), 1.44 (s, 18H), 2.75 (d, J=4.8 Hz, 2H), 3.02 (d, J=5.2 Hz, 2H), 3.36-3.71 (m, 34H), 3.89 (d, J=5.6 Hz, 2H), 4.35-4.40 (m, 8H), 4.49-4.56 (m, 8H), 6.38 (t, J=4.8 Hz, 1H), 6.60 (t, J=5.2 Hz, 1H), 6.94 (t, J=5.6 Hz, 1H), 7.12 (d, J=2 Hz, 2H), 7.24 (s, 9H), 7.30 (s, 8H), 7.40 (t, J=2 Hz, 1H), 7.66 (s, 3H); $^{13}$C NMR (100 MHz, CD$_3$COCD$_3$): δ=31.9, 32.0, 35.5, 35.7, 42.7, 43.0, 43.2, 44.3, 69.6, 69.7, 71.1, 71.2, 73.5, 73.6, 121.6, 122.8, 123.8, 125.4, 129.4, 129.5, 136.2, 138.1, 138.1, 139.3, 150.9, 150.9, 167.4, 168.2, 168.7, 168.9; HRMS (ESI): m/z [M+H]$^+$: C$_{84}$H$_{119}$N$_4$O$_{16}$ calcd. 1439.8621, found 1439.8571; [M+Na]$^+$: C$_{84}$H$_{118}$N$_4$O$_{16}$Na calcd. 1461.8441, found 1461.8384.

Example 13

Amide 6 Containing One Repeating Unit of Nylon-6,6

Scheme 13

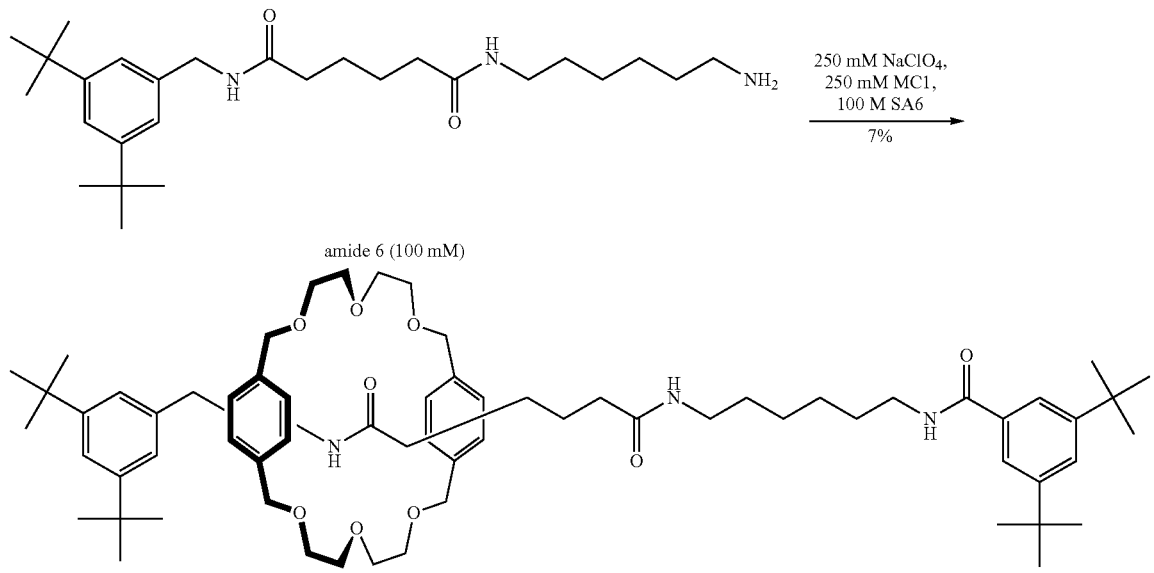

[2]rotaxane 20

In this example, amide 6 containing one repeating unit of nylon-6,6 was used as the guest molecule. The templating salt, the host molecule, and the stoppering agent were NaClO$_4$, MC1, and SA6, respectively. For preparing the rotaxane 20, a CH$_2$Cl$_2$ solution containing amide 6, NaClO$_4$, and MC1 was added with SA6, and then stirred at ambient temperature for 16 hours.

Since amide 6 containing the repeating unit of nylon-6,6, the successful synthesis of rotaxane 20 supported that such a Na$^+$ ion-assisted host-guest complexation system can be used directly to form interwoven or interlocked structures from common peptides and other amide bond containing bio- and artificial (macro)molecules without alternating their key molecular structures.

Figure 16A:
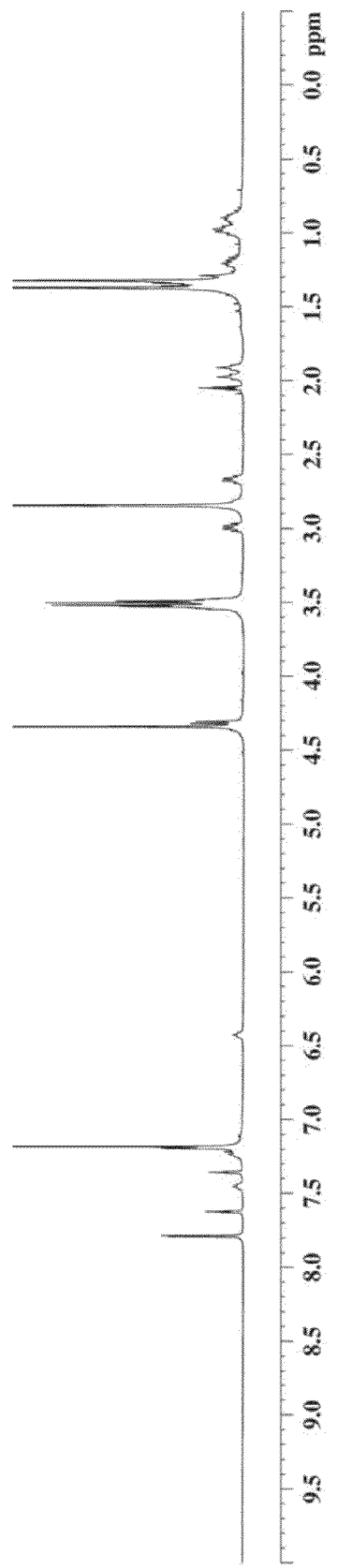
FIGS. 16A and 16B are $^1$H NMR (400 MHz, CD$_3$COCD$_3$, 298 K) and $^{13}$C NMR (100 MHz, CD$_3$COCD$_3$, 298 K) spectra of rotaxane 20, respectively.
Figure 16B:
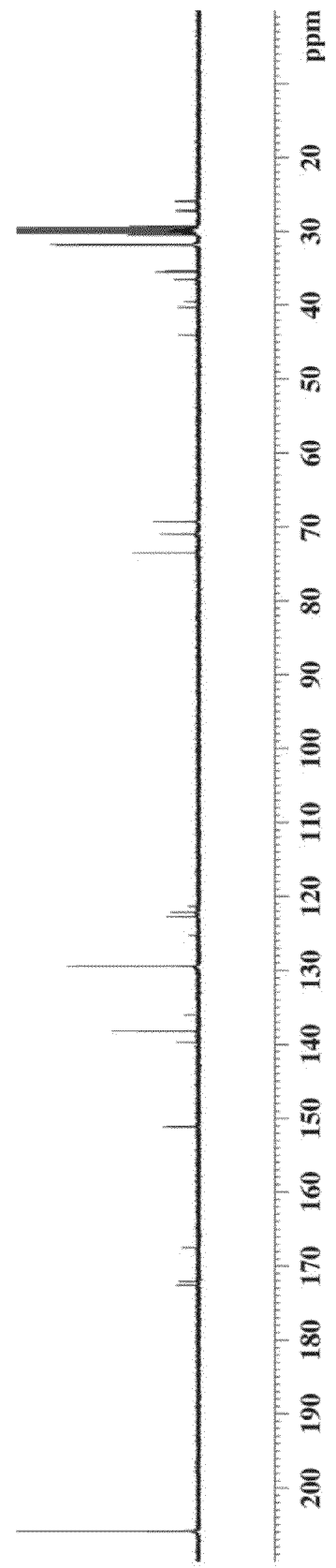

The $^1$H NMR and $^{13}$C NMR spectra of rotaxane 20 are shown in FIGS. 16A and 16B, respectively. All related spectral data are listed below.

Rotaxane 20: M.p. 161-163° C., $^1$H NMR (400 MHz, CD$_3$COCD$_3$): δ=0.82-1.02 (m, 8H), 1.14-1.25 (m, 4H), 1.32 (s, 18H), 1.37 (s, 18H), 1.91 (t, J=6.8 Hz, 2H), 1.97 (t, J=7.2 Hz, 2H), 2.67 (q, J=6.4 Hz, 2H), 2.99 (q, J=6.8 Hz, 2H), 3.48-3.54 (m, 16H), 4.31 (d, J=5.6 Hz, 2H), 4.34 (s, 8H), 6.40-6.45 (br, 1H), 7.16-7.23 (m, 11H), 7.36 (t, J=1.6 Hz, 1H), 7.42-7.47 (br, 1H), 7.62 (t, J=1.6 Hz, 1H), 7.79 (d, J=1.6 Hz, 2H); $^{13}$C NMR (100 MHz, CD$_3$COCD$_3$): δ=25.8, 26.0, 27.1, 27.3, 31.8, 31.9, 35.3, 35.6, 36.6, 36.6, 39.5, 40.3, 44.0, 69.3, 71.0, 73.5, 121.4, 122.1, 122.7, 125.3, 129.4, 136.0, 138.1, 139.7, 151.0, 151.1, 167.5, 172.1, 172.6 (two signals are missing, possibly because of signal overlapping); HRMS (ESI): m/z [M+Na]$^+$: C$_{66}$H$_{99}$N$_3$O$_9$Na calcd. 1100.7279, found 1100.7243.

Embodiment 4

Guest Molecules Containing at Least One Oligo(Ethylene Glycol) Group

Example 14

Ether 1 Containing a Di-Ethylene Glycol Moiety

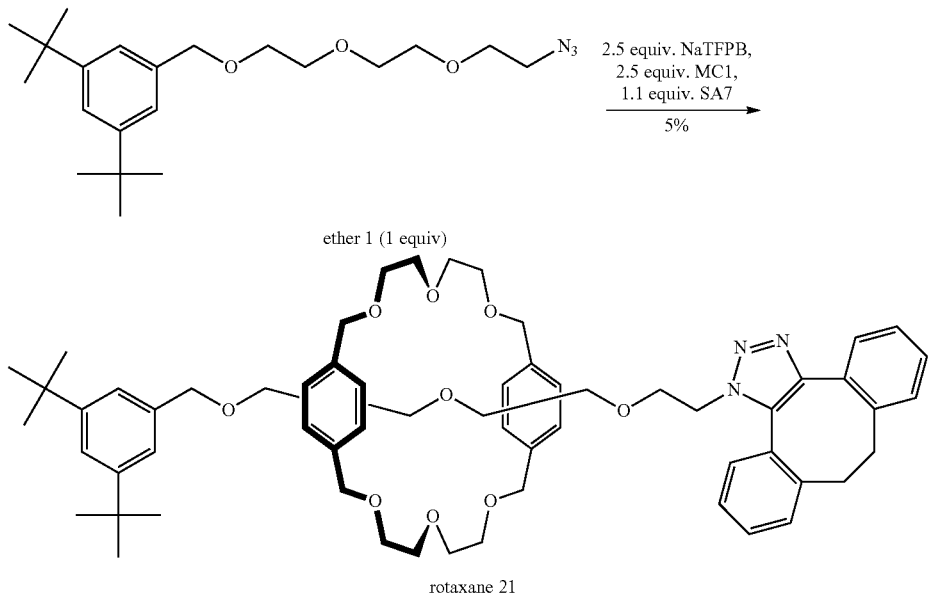

Scheme 14

In this example, ether 1 containing a diethylene glycol segment was used as the guest molecule. NaTFPB was used as the templating salt. MC1 was used as the host molecule. SA7 was used as the stoppering agent. For preparing the rotaxane 21, a solid mixture obtained from concentrating a CH$_2$Cl$_2$ solution mixture of ether 1, NaTFPB and MC1 was mixed with solid SA7 and ball-milled at 20 Hz for 90 minutes.

Since ether 1 and MC1 contain only aromatic and diethylene glycol units, between which hydrogen bond cannot be generated, the pseudorotaxane precursor for the synthesis of rotaxane 21 must be assembled by using Na$^+$ ion to template the threading the diethylene glycol segment of ether 1 into MC1.

Figure 17A:
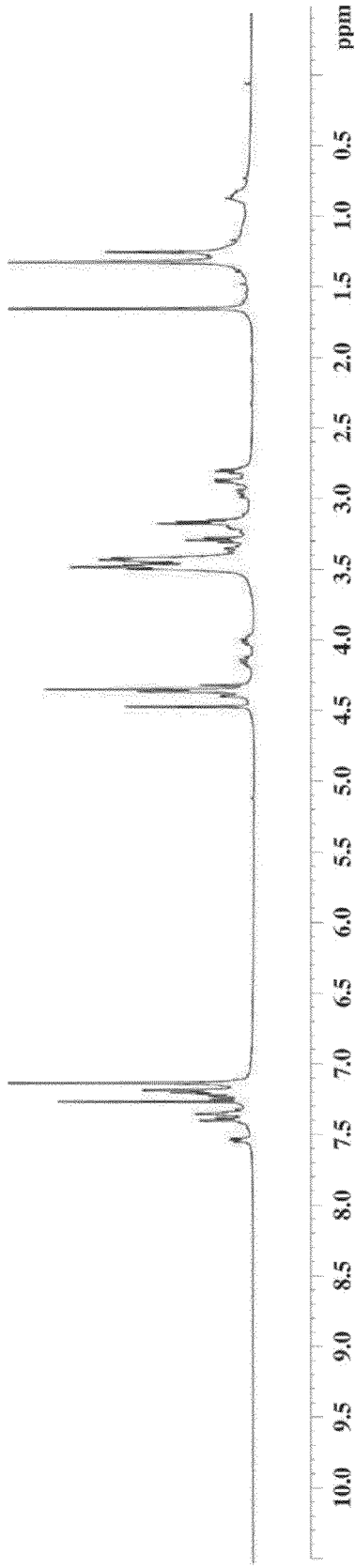
FIGS. 17A and 17B are $^1$H NMR (400 MHz, CDCl$_3$, 298 K) and $^{13}$C NMR (100 MHz, CDCl$_3$, 298 K) spectra of rotaxane 21, respectively.
Figure 17B:
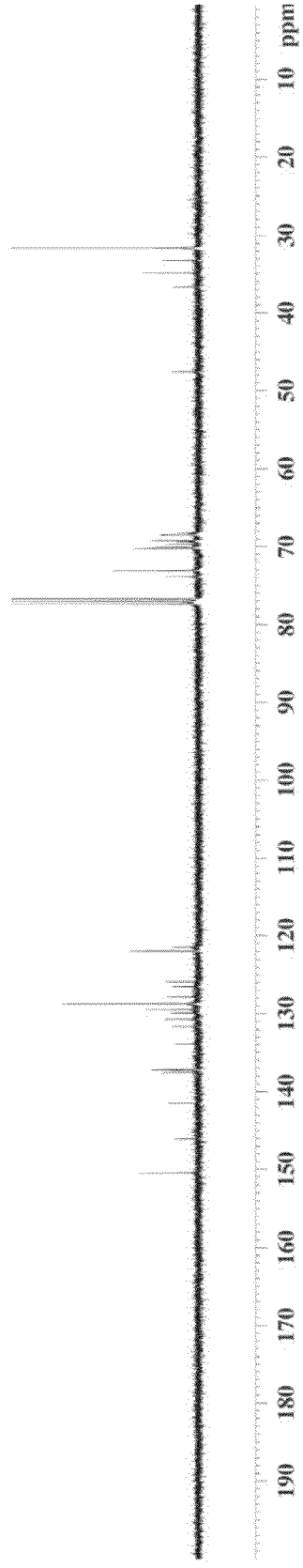

The $^1$H NMR and $^{13}$C NMR spectra of rotaxane 21 are shown in FIGS. 17A and 17B, respectively. All related spectral data are listed below.

Rotaxane 21: $^1$H NMR (400 MHz, CDCl$_3$): δ=1.33 (s, 18H), 2.63-2.74 (m, 2H), 2.75-2.83 (m, 2H), 2.91-3.01 (m, 1H), 3.01-3.09 (m, 1H), 3.09-3.31 (m, 6H), 3.33-3.55 (m, 21H), 3.63-3.74 (m, 1H), 3.86-3.97 (m, 1H), 4.03-4.14 (m, 1H), 4.29-4.39 (m, 8H), 4.43 (s, 2H), 7.09 (s, 8H), 7.16-7.22 (m, 6H), 7.30-7.41 (m, 4H), 7.49-7.55 (m, 1H); $^{13}$C NMR (100 MHz, CDCl$_3$): δ=31.6, 33.2, 34.9, 36.7, 47.5, 68.0, 68.5, 68.9, 69.1, 69.4, 69.5, 70.3, 73.1, 73.9, 121.5, 122.0, 125.9, 126.5, 126.6, 127.4, 127.8, 128.7, 129.5, 129.9, 130.0, 130.7, 131.6, 133.9, 137.2, 137.3, 137.5, 141.5, 146.0, 150.4; HRMS (ESI): m/z [M+H]$^+$ C$_{61}$H$_{80}$N$_3$O$_9$ calcd. 998.5894, found 998.5837; [M+Na]$^+$: C$_{61}$H$_{8679}$N$_3$O$_9$Na calcd. 1020.5714, found 1020.5688.

Example 15

Ether 2 Containing a Tri-Ethylene Glycol Moiety

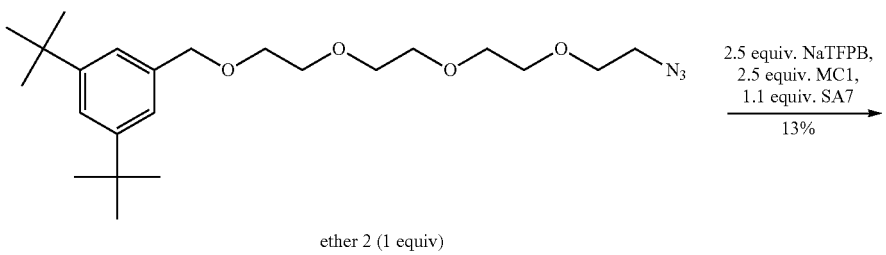

Scheme 15

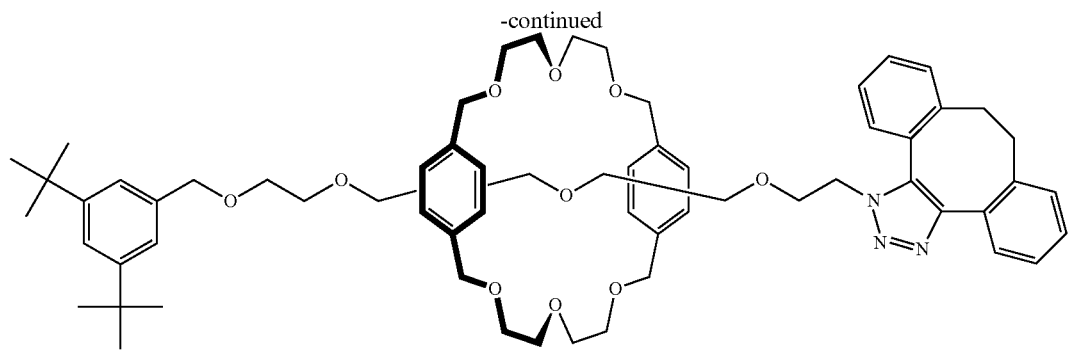

rotaxane 22

In this example, ether 2 containing a triethylene glycol segment was used as the guest molecule. NaTFPB was used as the templating salt. MC1 was used as the host molecule. SA7 was used as the stoppering agent. For preparing the rotaxane 22, a solid mixture obtained from concentrating a $CH_2Cl_2$ solution mixture of ether 2, NaTFPB and MC1 was mixed with solid SA7 and ball-milled at 20 Hz for 90 minutes.

The higher yield in the synthesis of rotaxane 22 compared to the one of rotaxane 21 under similar condition is likely to due to the triethylene glycol motif of ether 2 contains more oxygen atoms than the diethylene glycol one of ether 1, which increases its affinity to the templating $Na^+$ ion and stabilizes the corresponding pseudorotaxane more.

All related spectral data of rotaxane 22 are listed below.

Rotaxane 22: $^1H$ NMR (400 MHz, $CDCl_3$): δ=1.31 (s, 18H), 2.73-2.82 (m, 2H), 2.82-2.89 (m, 2H), 2.89-2.99 (m, 2H), 3.07-3.21 (m, 6H), 3.24-3.30 (m, 2H), 3.36-3.51 (m, 20H), 3.91-4.03 (m, 1H), 4.08-4.19 (m, 1H), 4.27-4.40 (m, 8H), 4.45 (s, 2H), 4.457.11 (s, 8H), 7.14-7.23 (m, 6H), 7.28-7.41 (m, 4H), 7.49-7.53 (m, 1H), $^{13}C$ NMR (100 MHz, $CDCl_3$): δ=31.6, 33.2, 34.9, 36.7, 47.5, 68.2, 68.5, 69.2, 69.2, 69.3, 69.7, 70.1, 70.3, 73.1, 73.9, 121.5, 122.0, 125.9, 126.5, 126.5, 127.8, 128.7, 129.4, 129.9, 129.9, 130.7, 131.6, 133.9, 137.2, 137.2, 137.3, 137.5, 141.5, 146.0, 150.5 (one signals is missing, possibly because of signal overlapping); HRMS (ESI): m/z $[M+H]^+$ $C_{63}H_{84}N_3O_{10}$ calcd. 1042.6156, found 1042.6188.

Example 16

Ether 3 Containing a Tetra-Ethylene Glycol Moiety

Scheme 16

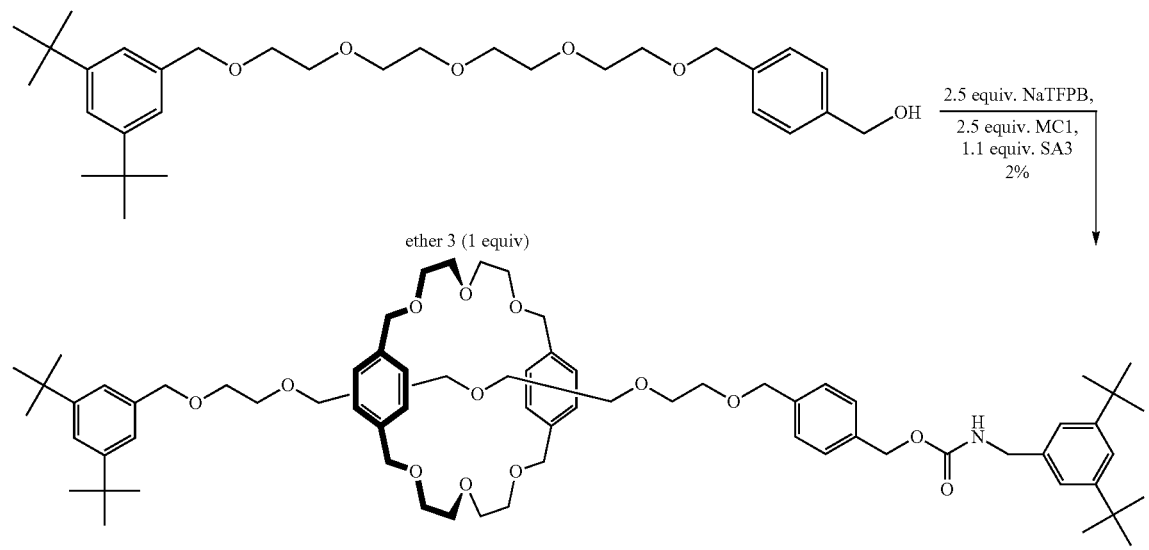

rotaxane 23

In this example, ether 3 containing a tetra-ethylene glycol segment was used as the guest molecule. NaTFPB was used as the templating salt. MC1 was used as the host molecule. SA3 was used as the stoppering agent. For preparing the rotaxane 23, a sticky liquid obtained from concentrating a $CH_2Cl_2$ solution mixture of ether 3, NaTFPB and MC1 was mixed with SA3 and the neat mixture was stirred until solidified.

Compared to ether 2, ether 3 contains an even longer ethylene glycol chain for binding the Na⁺ ion template. The relatively low yield in the synthesis of rotaxane 23 compared to the one of rotaxane 22, however, may due to different stoppering method applied or the increasing tendency for ether 3 to bind Na⁺ ion template alone.

The $^1$H NMR and $^{13}$C NMR spectra of rotaxane 23 are shown in FIGS. 18A and 18B, respectively. All related spectral data are listed below.

Rotaxane 23: $^1$H NMR (400 MHz, CDCl$_3$, 298 K): δ=1.30 (s, 18H), 1.32 (s, 18H), 3.39-3.69 (m, 32H), 3.80 (d, J=5.3 Hz, 2H), 4.21-4.34 (m, 10H), 4.50 (s, 2H), 4.52 (s, 2H), 5.81 (t, J=4.7 Hz, 1H), 6.95 (s, 8H), 7.03-7.08 (m, 4H), 7.14-7.20 (m, 4H), 7.30 (d, J=10.2 Hz, 2H); $^{13}$C NMR (100 MHz, CDCl$_3$, 298 K): δ=31.6, 31.7, 34.9, 34.9, 45.6, 65.1, 68.6, 69.2, 69.4, 70.3, 70.6, 73.1, 73.9, (five aliphatic carbon signals are missing possibly because of signal overlapping) 120.9, 121.5, 121.9, 123.0, 126.8, 127.5, 128.4, 136.3, 136.8, 137.1, 137.5, 150.3, 150.5, 155.6; (one aromatic carbon signal is missing possibly because of signal overlap); HRMS (ESI): m/z [M+H]⁺ C$_{71}$H$_{104}$NO$_{13}$ calcd.1178.7507, found 1178.7553.

Embodiment 5

Using Diamine and Dialdehyde to Synthesize Host Molecules, Guest Molecules, or Both Example 17

DAM1 Containing a Di-Ethylene Glycol Moiety

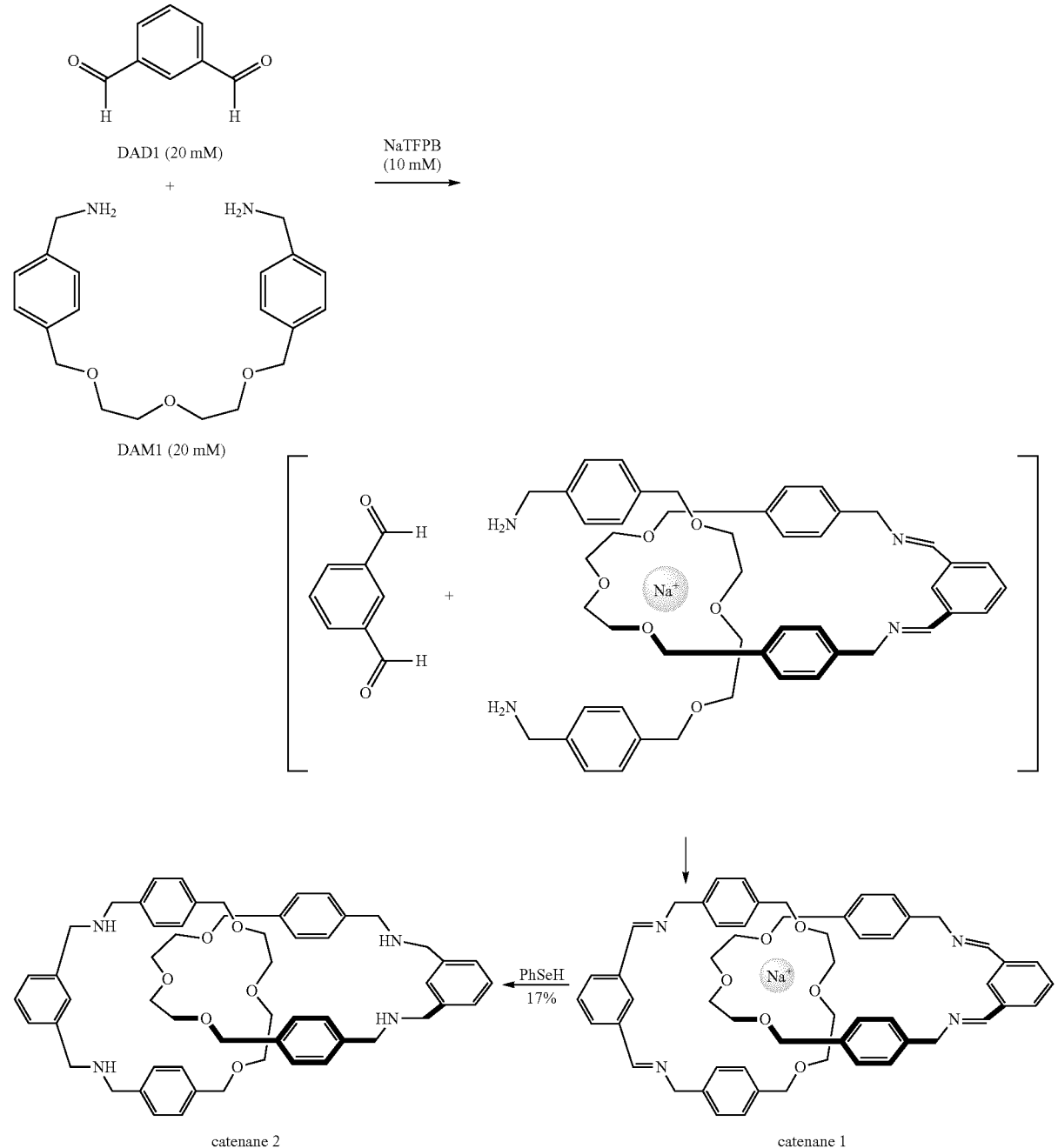

In this example, DAM1 containing a diethylene glycol segment was used as the guest molecule. NaTFPB was used as the templating salt. MC7, which in situ generated from the imine formation reaction of DAM1 and DAD1 was used as the host molecule. For preparing the catenane 1, DAM1, NaTFPB and DAD1 were mixed in $CH_2Cl_2$ and the solution mixture was stirred at 50° C. for 16 hours.

Figure 19:
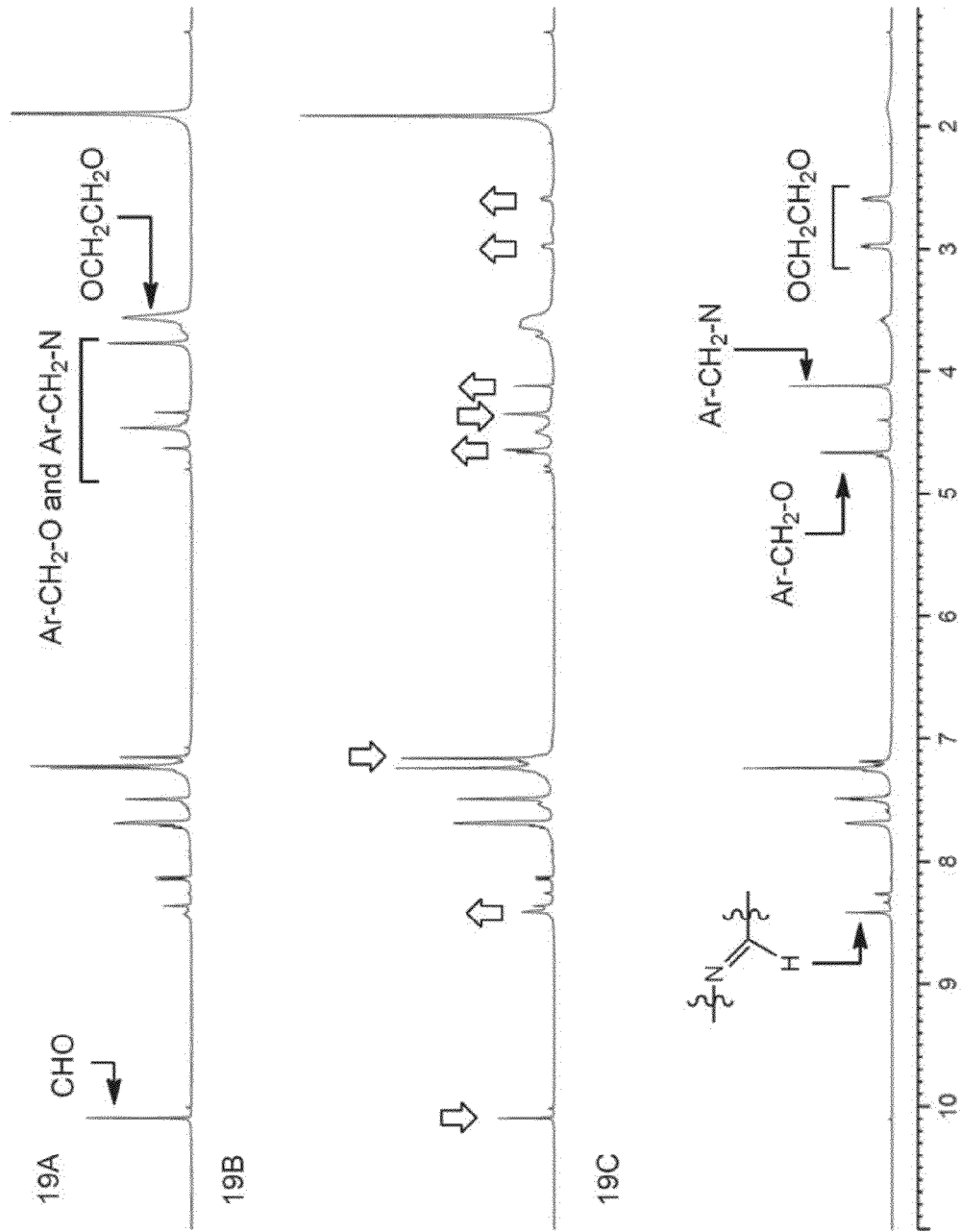
FIG. 19 containing spectra 19A-19C, and spectra 19A-19C are the partial $^1$H NMR spectra (400 MHz, CDCl$_3$, 298 K) displaying the formation of catenane 1 from an mixture of DAM1, DAD1, and NaTFPB (20 mM:20 mM:10 mM) for 0, 0.33, and 3 h, respectively.

Spectra 19A-19C in FIG. 19 are the partial $^1H$ NMR spectra (400 MHz, $CDCl_3$, 298 K) displaying the formation of catenane 1 from an mixture of DAM1, DAD1, and NaTFPB (20 mM:20 mM:10 mM) over time. A new set of signals corresponding to catenane 1 was observed in the original mixture (spectrum 19B), which then became the predominated species in solution after 3 hours (spectrum 19C). Comparing spectra 19A and 19C, the disappearance of the aldehyde signal at δ 10.10 and the appearance of the imine signal at δ 8.42, suggested that the DAD1 and DAM1 have been linked by imine bonds. The significant upfield shifted of the diethylene glycol signal at δ 2.59 and 2.98 in the $^1H$ NMR spectrum, indicated its location in the shielding zone of the xylene groups and supported the formation of the catenane 1.

According to similar NMR experiments, signals belong to catenane 1 cannot be observed in the spectra when zero or one equivalent of NaTFPB was applied under similar reaction condition. This result not only suggested that $Na^+$ ion is a crucial template for the formation of catenane 1 but also supported the need for two diethylene glycol chains in such a complexation.

Since imine bonds are easily hydrolyzed, catenane 1 was not subject to further purification. PhSeH was used to reduce the imine bonds in catenane 1 and catenane 2, which has two MC8 interlocked, was isolated in 17% yield after column chromatography. According to the $^1H$ NMR spectrum, catenane 1 was the predominate species in solution; the relative low yield in the synthesis of catenane 2, however, suggested that the PhSeH reduction reaction is not efficient enough to prevent the dissociation of the components.

MC7 contains a diethylene glycol, a 1,3-bis(iminomethyl)benzene and two xylene groups. The formation of catenane 1 in solution suggested that DAM1 is capable to thread through MC7 with the assistance from $Na^+$ ion template. This result confirmed that pseudorotaxane formed from threading one oligo(ethylene glycol) containing guest into another oligo(ethylene glycol) containing macrocycle can not only be used to synthesize rotaxanes but also to construct catenanes. Therefore, pseudorotaxanes formed from guests containing urea, carbamate and amide groups and similar macrocyclic imine hosts should also be reasonable precursors for preparing the corresponding catenanes and rotaxanes.

Figure 20A:
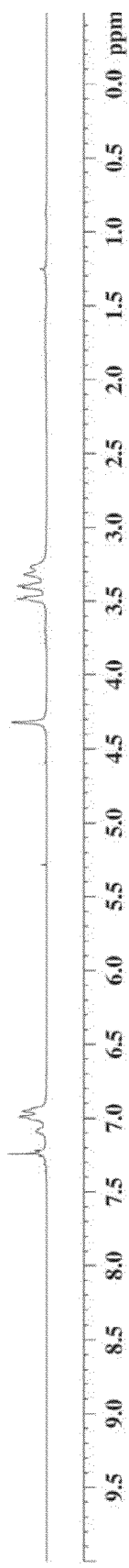
FIGS. 20A and 20B are $^1$H NMR (400 MHz, CDCl$_3$, 298 K) and $^{13}$C NMR (100 MHz, CD$_3$OD, 298 K) spectra of catenane 2, respectively.
Figure 20B:

All related spectral data of catenane 2 are listed below. The $^1H$ NMR and $^{13}C$ NMR spectra of catenane 2 are shown in FIGS. 20A and 20B, respectively.

Catenane 2: $^1H$ NMR (400 MHz, $CDCl_3$): δ=3.20-3.35 (br, 16 H), 3.37-3.43 (br, 8 H), 3.45-3.51 (br, 8 H), 4.32 (s, 8 H), 6.90-7.03 (br, 18 H), 7.06-7.11 (br, 4 H), 7.24 (t, J=8 Hz, 4H); $^{13}C$ NMR (100 MHz, $CD_3OD$): δ=$^{13}C$ NMR (100 MHz, $CD_3OD$): δ=53.9, 54.6, 70.1, 71.2, 74.1, 128.2, 129.1, 129.7, 130.0, 130.1, 138.1, 140.2, 140.8; HR-MS (ESI): m/z calcd for $[M+H]^+$ $C_{56}H_{69}N_4O_6^+$: 893.5212, found 893.5158.

Example 18

MC1 Containing Two Di-Ethylene Glycol Moiety

In this example, DAM2 containing a 2,6-bis(hydroxymethyl)pyridine segment was used as the guest molecule. NaTFPB was used as the templating salt. MC1 was used as the host molecule. For preparing the catenane 3, DAM2, NaTFPB and DAD1 were mixed in $CH_2Cl_2$ and the solution mixture was stirred at 50° C. for 48 hours.

Since imine bonds are easily hydrolyzed, catenane 3, which has MC1 and MC9 interlocked, was not subject to further purification. PhSeH was used to reduce the imine bonds in catenane 3 and catenane 4, which has MC1 and MC10 interlocked, was isolated in 7% yield after column chromatography.

Scheme 18

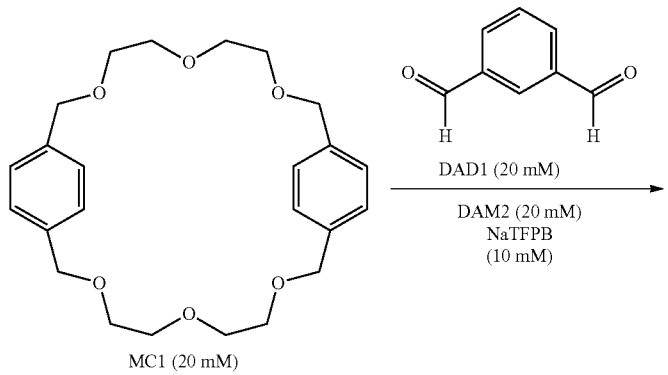

MC1 (20 mM)

DAD1 (20 mM)

DAM2 (20 mM)
NaTFPB
(10 mM)

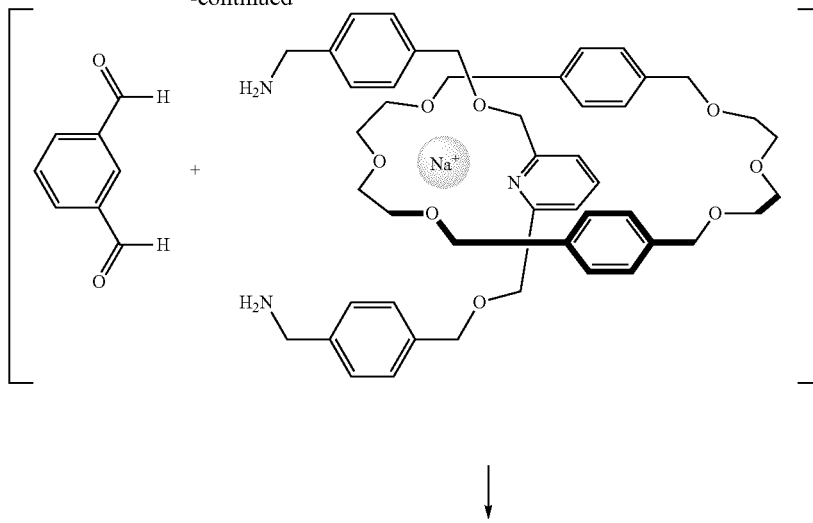

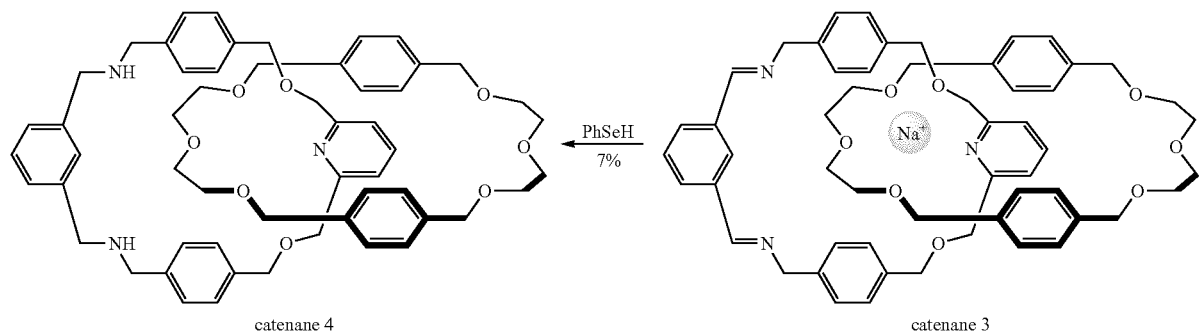

catenane 4    catenane 3

MC1 contains two diethylene glycol and two xylene groups. MC9 contains a 2,6-bis(hydoxymethyl)pyridine, a 1,3-bis(iminomethyl)benzene and two xylene groups. The formation of catenane 3 in solution suggested that the 2,6-bis(hydroxymethyl)pyridine motif in DAM2 is also capable to thread through MC1 with the assistance from $Na^+$ ion template. In the other hand, this result also suggested that the 2,6-bis(hydroxymethyl)pyridine motif in MC9 is also capable to accommodate the threading of an oligo(ethylene) glycol-containing guest under similar condition.

Figure 21A:
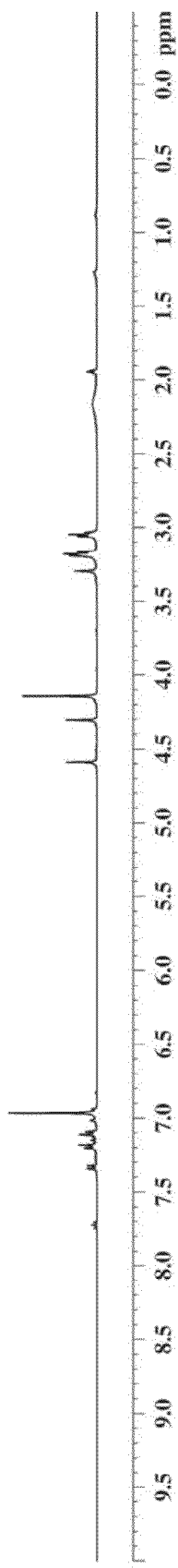
FIGS. 21A and 21B are $^1$H NMR (400 MHz, CD$_3$CN, 298 K) and $^{13}$C NMR (100 MHz, CD$_3$CN, 298 K) spectra of catenane 4, respectively.
Figure 21B:
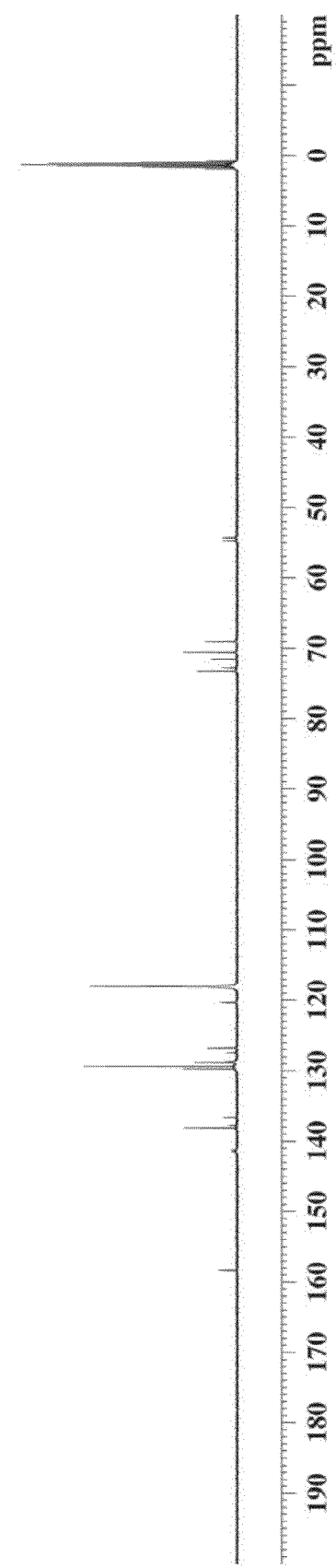

All related spectral data of catenane 4 are listed below. The $^1$H NMR and $^{13}$C NMR spectra of catenane 4 are shown in FIGS. 21A and 21B, respectively.

Catenane 4: $^1$H NMR (400 MHz, $CD_3CN$): δ=3.05 (t, J=6 Hz, 8H), 3.16-3.21 (m, 12H), 3.30 (s, 4H), 4.14 (s, 8H), 4.30 (s, 4H), 4.59 (s, 4H), 6.93-6.98 (m, 10H), 7.02 (s, 1H), 7.10 (d, J=8 Hz, 4H), 7.15 (t, J=8 Hz, 1H), 7.19 (d, J=8 Hz, 4H), 7.33 (d, J=8 Hz, 2H), 7.72 (t, J=8 Hz, 1H); $^{13}$C NMR (100 MHz, $CD_3CN$): δ=54.3, 54.7, 69.0, 70.5, 71.5, 72.8, 73.3, 120.3, 26.8, 127.4, 128.7, 128.8, 129.4, 129.7, 136.6, 137.8, 138.1, 41.2, 141.5, 158.4; HR-MS (ESI): m/z calcd for $[M+H]^+$ $C_{55}H_{66}N_3O_8^+$: 896.4850, found 896.4850.

Example 19
DAM2 Containing a 2,6-Bis(hydroxymethyl)pyridine Moiety and DAD1
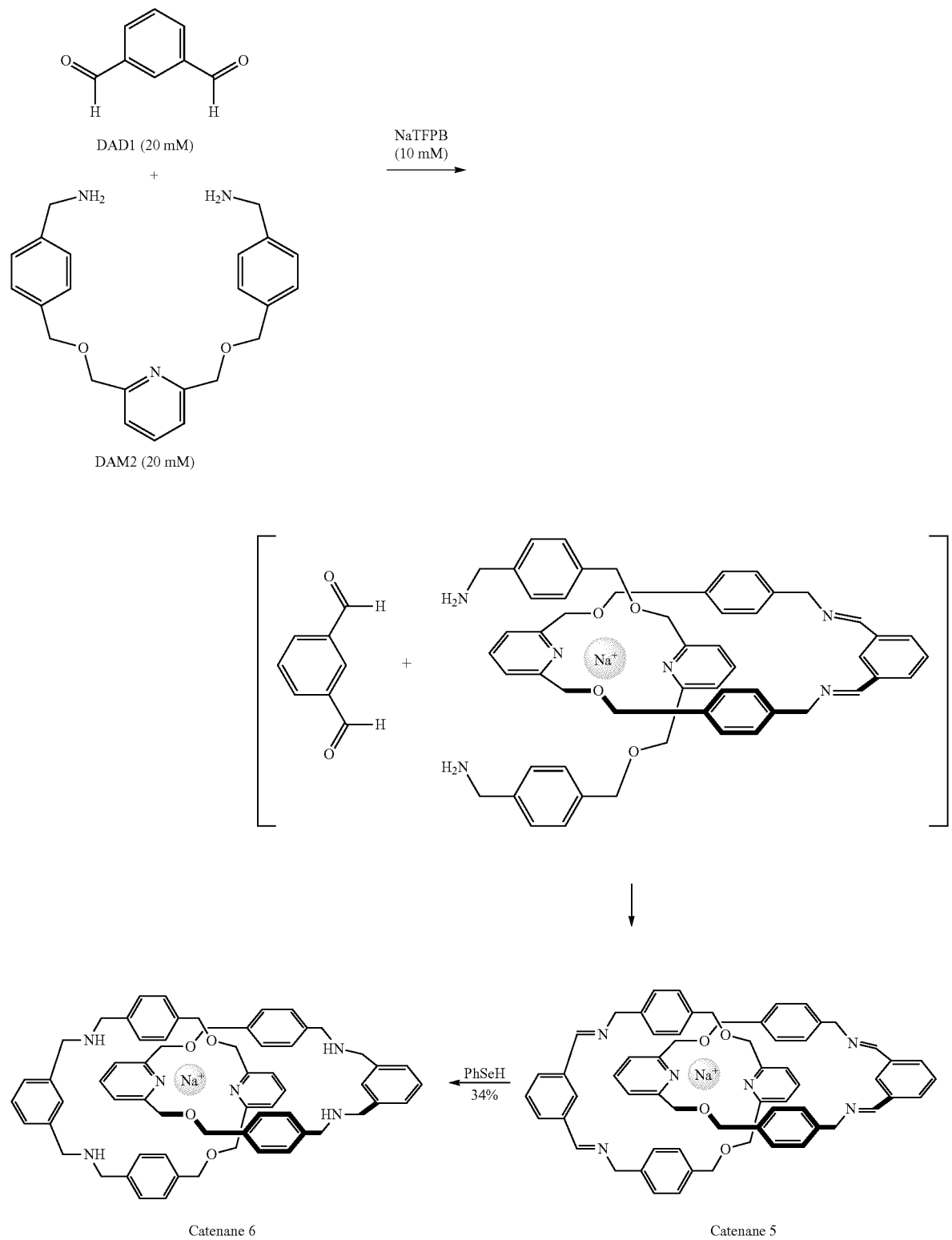
Scheme 19

In this example, DAM2 containing a 2,6-bis(hydroxymethyl)pyridine segment was used as the guest molecule. NaTFPB was used as the templating salt. MC9, which in situ generated from the imine formation reaction of DAM2 and DAD1 was used as the host molecule. For preparing the catenane 5, DAM2, NaTFPB and DAD1 were mixed in CH$_2$Cl$_2$ and the solution mixture was stirred at 50° C. for 48 hours.

Since imine bonds are easily hydrolyzed, catenane 5 was not subject to further purification. PhSeH was used to reduce the imine bonds in catenane 5 and catenane 6, which has two MC10 interlocked, was isolated in 34% yield after column chromatography.

MC9 contains a 2,6-bis(hydroxymethyl)pyridine, a 1,3-bis(iminomethyl)benzene and two xylene groups. The formation of catenane 5 in solution suggested that DAM2 is capable to thread through MC9 with the assistance from Na$^+$ ion template. This result confirmed that pseudorotaxane formed by threading one 2,6-bis(hydroxymethyl)pyridine containing guest into another 2,6-bis(hydroxymethyl)pyridine containing macrocycle can not only be used to synthesize rotaxanes but also to construct catenanes. Therefore, pseudorotaxane formed from guests containing urea, carbamate, amide or oligo(ethylene glycol) group and similar macrocyclic imine hosts should also be reasonable precursors for preparing the corresponding catenanes and rotaxanes.

Figure 22A:
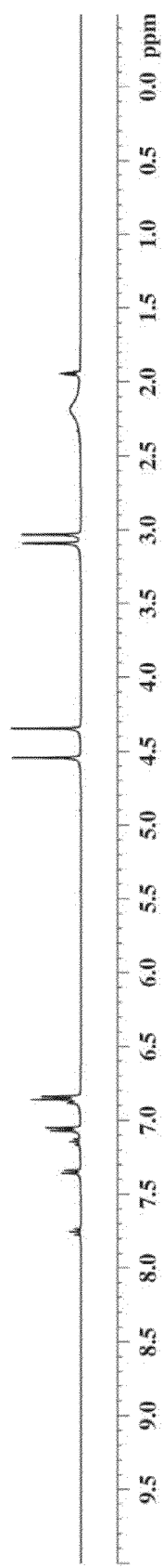
FIGS. 22A and 22B are $^1$H NMR (400 MHz, CD$_3$CN, 298 K) and $^{13}$C NMR (100 MHz, CD$_3$CN, 298 K) spectra of catenane 6, respectively.
Figure 22B:
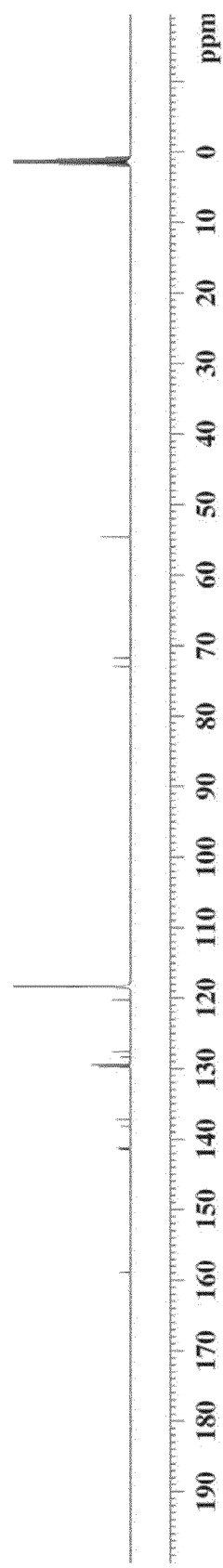

All related spectral data of catenane 6 are listed below. The $^1$H NMR and $^{13}$C NMR spectra of catenane 6 are shown in FIGS. 22A and 22B, respectively.

Catenane 6: $^1$H NMR (400 MHz, CD$_3$CN): δ=3.03 (s, 8H), 3.08 (s, 8H), 4.35 (s, 8H), 4.54 (s, 8H), 6.83-6.90 (m, 16H), 7.06 (d, J=8 Hz, 8H), 7.14 (t, J=8 Hz, 2H), 7.35 (d, J=8 Hz, 4H), 7.75 (t, J=8 Hz, 2H); $^{13}$C NMR (100 MHz, CD$_3$CN): δ=54.6, 71.7, 73.0, 120.3, 127.6, 128.4, 129.5, 129.7, 129.8, 137.2, 138.2, 141.3, 141.4, 158.9 (one signal is missing, possibly because of signal overlapping); HR-MS (ESI): m/z calcd for [M+H]$^+$ C$_{62}$H$_{67}$N$_6$O$_4{}^+$: 959.5218, found 959.5269.

Example 20

DAM2 Containing 2,6-Bis(hydroxymethyl)pyridine Moiety and DAD2

Scheme 20

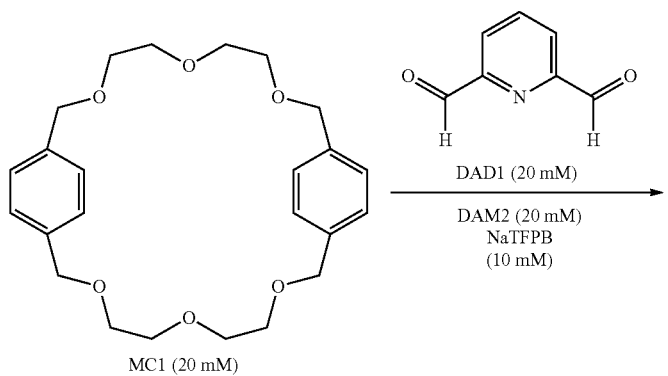

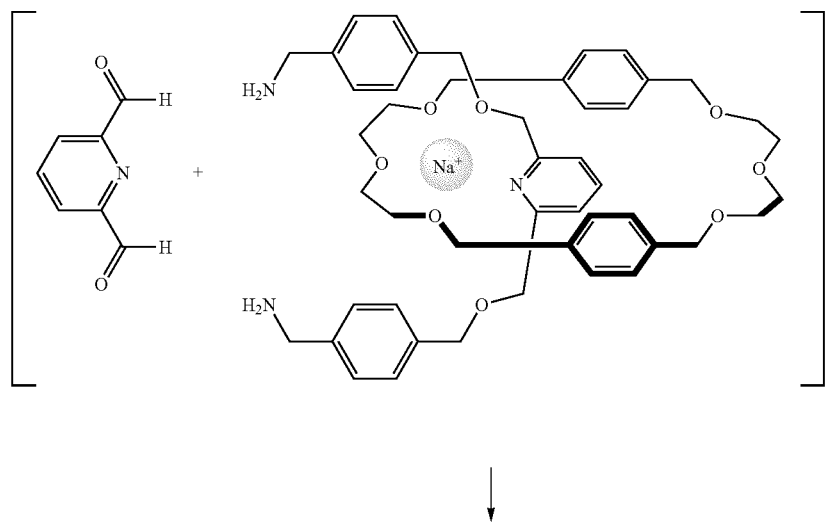

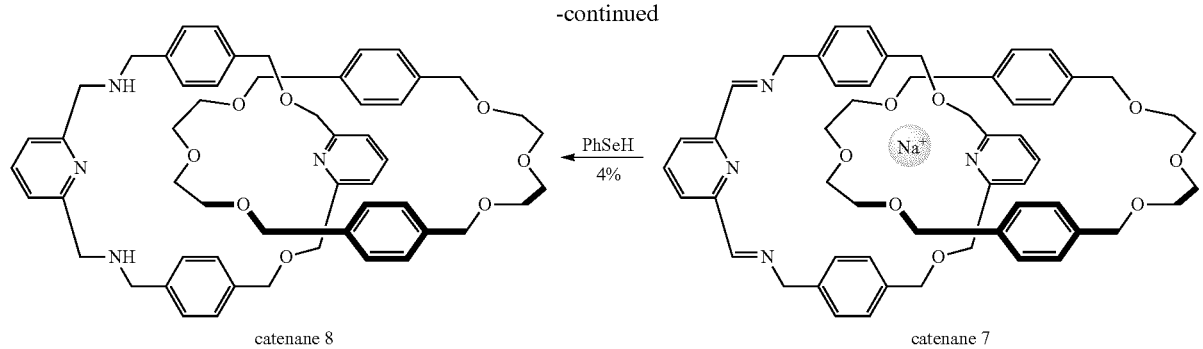

catenane 8          catenane 7

In this example, DAM2 containing a 2,6-bis(hydroxymethyl)pyridine segment was used as the guest molecule. NaTFPB was used as the templating salt. MC1 was used as the host molecule. For preparing the catenane 7, DAM2, NaTFPB and DAD2 were mixed in CH$_2$Cl$_2$ and the solution mixture was stirred at 50° C. for 48 hours.

Since imine bonds are easily hydrolyzed, catenane 7 was not subject to further purification. PhSeH was used to reduce the imine bonds in catenane 7 and catenane 8, which has MC1 and MC12 interlocked, was isolated in 4% yield after column chromatography.

MC1 contains two diethylene glycol and two xylene groups. MC11 contains a 2,6-bis(hydroxymethyl)pyridine, a 2,6-bis(iminomethyl)pyridine and two xylene groups. The formation of catenane 7 in solution indicated that DAD2 is also capable to cyclize the pseudorotaxane formed from DAM2, MC1 and Na$^+$ ion and suggested the existence of structural flexibilities in the dialdehyde used in such a self-assembly approach.

Figure 23A:
FIGS. 23A and 23B are $^1$H NMR (400 MHz, CD$_3$CN, 298 K) and $^{13}$C NMR (100 MHz, CD$_3$CN, 298 K) spectra of catenane 8, respectively.
Figure 23B:
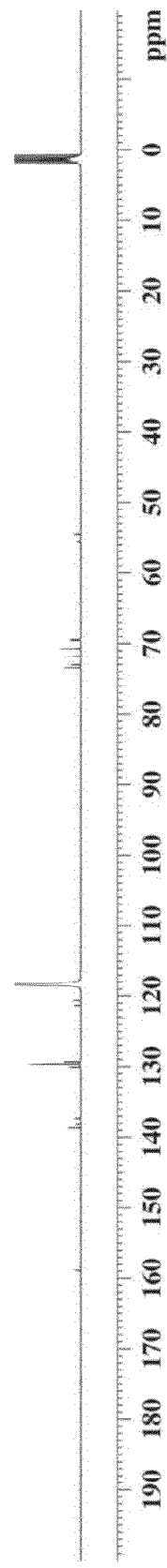

All related spectral data of catenane 8 are listed below. The $^1$H NMR and $^{13}$C NMR spectra of catenane 8 are shown in FIGS. 23A and 23B, respectively.

Catenane 8: $^1$H NMR (400 MHz, CD$_3$CN): δ=3.10-3.15 (br, 8H), 3.18-3.23 (br, 8H), 3.30 (br, 4H), 3.34 (s, 4H), 4.11 (s, 8H), 4.32 (s, 4H), 4.57 (s, 4H), 6.97 (s, 8H), 7.03-7.10 (m, 6H), 7.18 (d, J=8 Hz, 4H), 7.33 (d, J=8 Hz, 2H), 7.63 (t, J=8 Hz, 1H), 7.73 ppm (t, J=8 Hz, 1H), $^{13}$C NMR (100 MHz, CD$_3$CN): δ=54.5, 55.5, 69.4, 70.7, 71.8, 73.0, 73.4, 120.6, 121.3, 129.4, 129.6, 130.1, 137.3, 138.1, 138.6, 158.9 ppm (three signals are missing, possibly because of signals overlapping); HR-MS (ESI): m/z calcd for [M+H]$^+$ C$_{54}$H$_{65}$N$_4$O$_8$$^+$: 897.4797, found 897.4785.

Example 21

Urea 6 Containing a Urea Moiety

Scheme 21

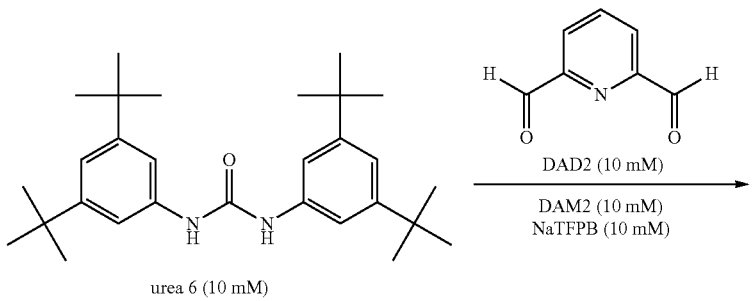

urea 6 (10 mM)

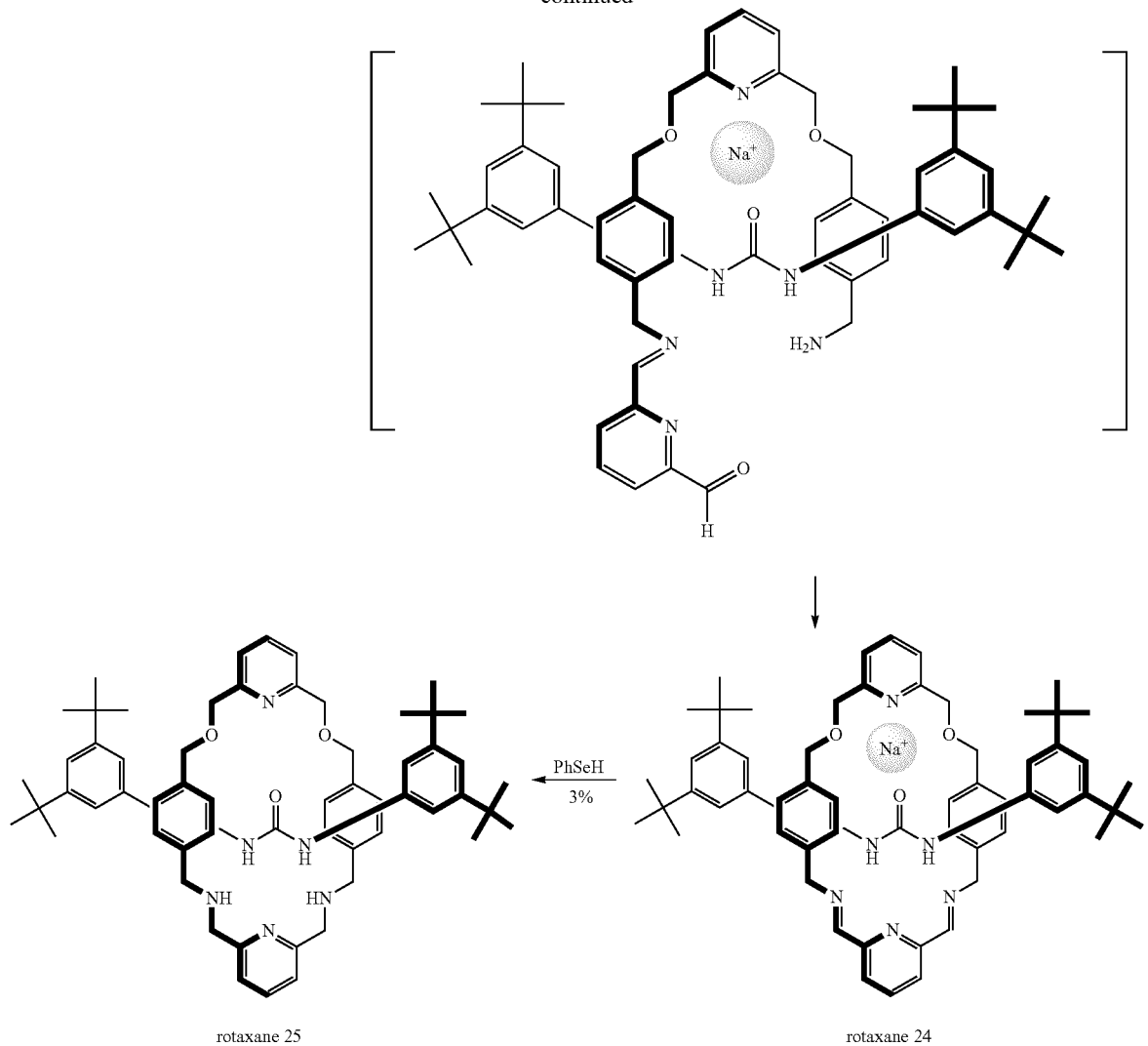

rotaxane 25          rotaxane 24

In this example, urea 6 was used as the dumbbell-shaped guest. DAM2 and DAD2 were used to generate MC11 in situ. NaTFPB was used as the templating salt. For preparing rotaxane 24, urea 6, DAM2, NaTFPB and DAD2 were mixed in $CH_2Cl_2$ and the solution mixture was stirred at 50° C. for 16 hours.

Since imine bonds are easily hydrolyzed, rotaxane 24 was not subject to further purification. PhSeH was used to reduce the imine bonds in rotaxane 24 and rotaxane 25, which has MC12 interlocked inside urea 6, was isolated in 3% yield after column chromatography.

MC11 contains a 2,6-bis(hydroxymethyl)pyridine, a 2,6-bis(iminomethyl)pyridine and two xylene groups. The formation of rotaxane 24 in solution indicated that $Na^+$ ion is capable to template the formation and encircling of MC11 on the urea functionality of urea 6. Thus, the same imine-formation "clipping" approach should also allow the formation of rotaxanes or catenanes from similar macrocyclic imine host and guests containing urea, carbamate, amide, oligo(ethylene glycol) and 2,6-bis(hydroxymethyl)pyridine groups.

Figure 24A:
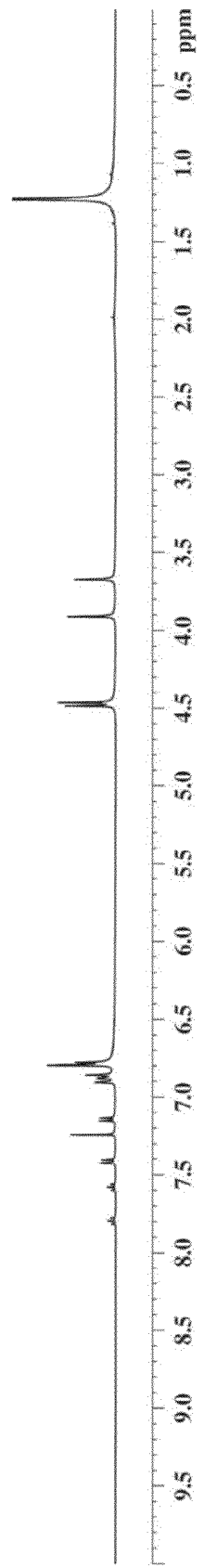
FIGS. 24A and 24B are $^1$H NMR (400 MHz, CDCl$_3$, 298 K) and $^{13}$C NMR (100 MHz, CDCl$_3$, 298 K) spectra of rotaxane 25, respectively.
Figure 24B:
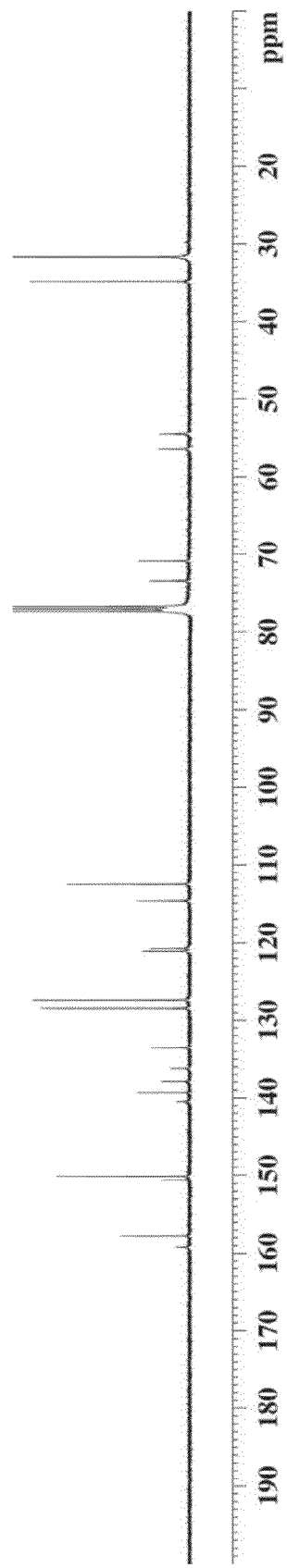

All related spectral data of rotaxane 25 are listed below. The $^1H$ NMR and $^{13}C$ NMR spectra of rotaxane 25 are shown in FIGS. 24A and 24B, respectively.

Rotaxane 25: $^1H$ NMR (400 MHz, $CDCl_3$): δ=1.23 (s, 36H), 3.68 (s, 4H), 3.91 (s, 4H), 4.46 (s, 4H), 4.48 (s, 4H), 6.76-6.81 (m, 8H), 6.87 (d, J=8 Hz, 4H), 6.90 (t, J=2 Hz, 2H), 7.14 (d, J=8 Hz, 2H), 7.41 (d, J=8 Hz, 2H), 7.58 (t, J=8 Hz, 1H), 7.80 (t, J=8 Hz, 1H); $^{13}C$ NMR (400 MHz, $CDCl_3$): δ=31.5, 34.7, 54.4, 56.4, 70.8, 73.4, 112.6, 114.7, 120.8, 121.2, 127.5, 128.6, 133.6, 136.3, 138.0, 139.5, 140.7, 150.3, 150.7, 157.9, 159.4; HR-MS (ESI): m/z calcd for $[M+H]^+$ $C_{59}H_{77}N_6O_3^+$: 917.6057, found 917.6057.

Accordingly, a new molecular recognition system has been discovered. In this new recognition system, a single recognition moiety, such as a urea group, a carbamate group, an amide group, an oligo(ethylene glycol) group or a 2,6-bis(hydroxymethyl)pyridine, of a threaded guest molecule can be recognized by a host molecule having a macrocyclic structure containing at least a binding unit (an oligo(ethylene glycol) group or a 2,6-bis(hydroxymethyl)pyridine group) and an aromatic linking spacer via a templating metal ion. This recognition system can also be applied on a guest molecule containing glycine residues, a repeating unit of Kelvar or a repeating unit of nylon-6,6. The extremely high structural flexibility of the guests for this recognition system will facilitate the introduction of interlocked or interwoven structures into (bio)materials found commonly in our daily lives to endow them with new functions or properties.

An the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. A pseudorotaxane complex comprising:
    a host molecule having a macrocycle structure comprising at least a binding unit and an aromatic linking spacer, wherein the binding unit is oligo(ethylene glycol);
    a guest molecule having at least a recognition moiety, wherein the recognition moiety is a urea group, a carbamate group, an amide group, an oligo(ethylene glycol) group or a 2,6-bis(hydroxymethyl)pyridine group; and
    a metal ion, wherein the metal ion coordinates to the binding unit of the host molecule and the recognition moiety of the guest molecule.

2. The pseudorotaxane complex of claim 1, wherein the host molecule further comprises a binding assistant unit, and the binding assistant unit is an oligo(ethylene glycol) group, a 2,6-bis(hydroxymethyl)pyridine, a 2,2'-oxy-di(ethanethiol) group, a 1,3-bis(iminomethyl)benzene group, or a 2,6-bis(iminomethyl)pyridine group.

3. The pseudorotaxane complex of claim 1, wherein the aromatic linking spacer is a p-xylenyl group or a 2,6-lutidinyl group.

4. The pseudorotaxane complex of claim 1, wherein the host molecule is

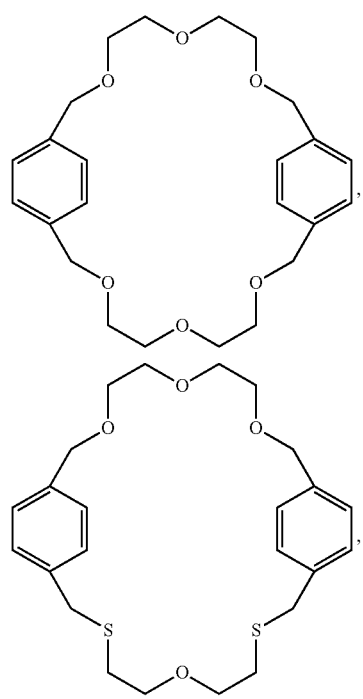

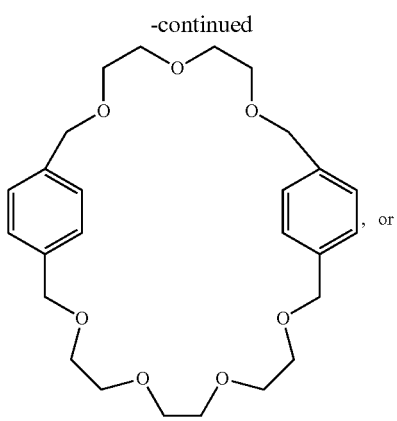, or

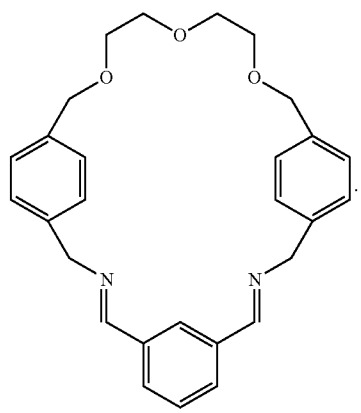 [SMILES: c1cc2cc(c1)CNCc1ccc(cc1)COCCOCCOCc1ccc(cc1)CNC2]

5. The pseudorotaxane complex of claim 1, wherein the guest molecule contains at least a glycine, a repeating unit of kevlar, or a repeating unit of nylon-6,6.

6. The pseudorotaxane complex of claim 1, wherein the metal ion is $Li^+$, $Na^+$ or $K^+$.

7. A rotaxane or a catenane synthesized from the pseudorotaxane complex of claim 1, comprising:
    a host molecule having a macrocycle structure comprising at least a binding unit and an aromatic linking spacer, wherein the binding unit is oligo(ethylene glycol); and
    a guest molecule having at least a recognition moiety, wherein the recognition moiety is a urea group, a carbamate group, an amide group, an oligo(ethylene glycol) group, or a 2,6-bis(hydroxymethyl)pyridine group.

8. The rotaxane or catenane of claim 7, wherein the host molecule further comprises a binding assistant unit, and the binding assistant unit is an oligo(ethylene glycol) group, a 2,6-bis(hydroxymethyl)pyridine, a 2,2'-oxy-di(ethanethiol) group, a 1,3-bis(iminomethyl)benzene group, a 1,3-bis(aminomethyl)benzene group, a 2,6-bis(iminomethyl)pyridine group, or a 2,6-bis(aminomethyl)pyridine group.

9. The rotaxane or catenane of claim 7, wherein the aromatic linking spacer is a p-xylenyl group or a 2,6-lutidinyl group.

10. The rotaxane or catenane of claim 7, wherein the host molecule is

61
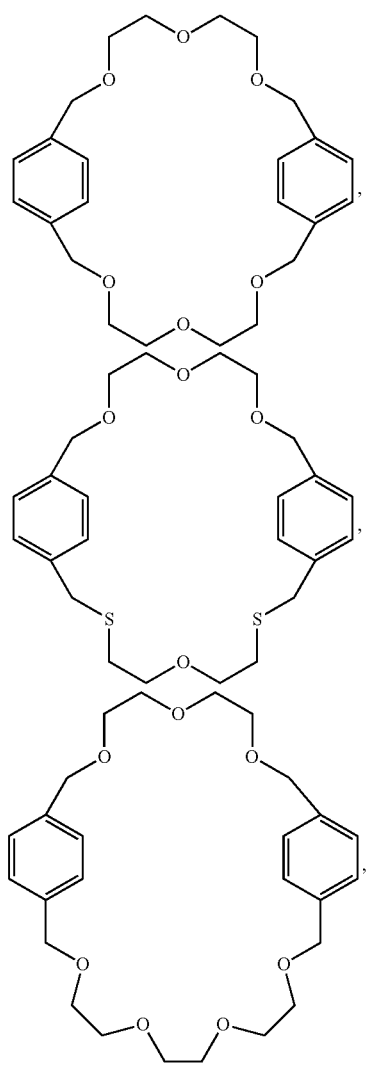
62
-continued
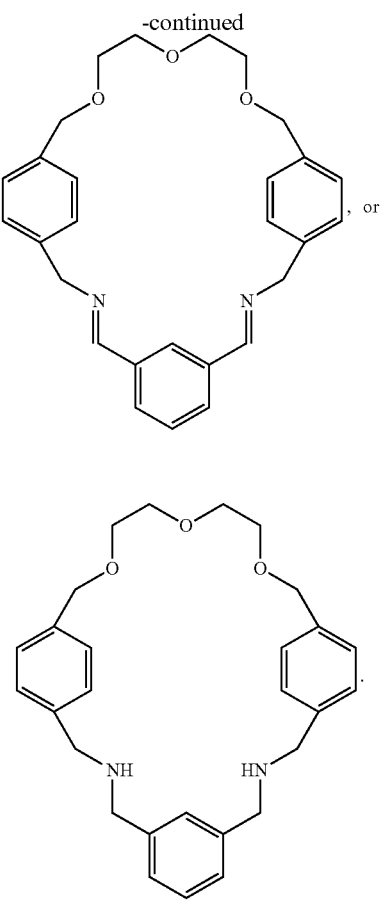
11. The rotaxane or catenane of claim 7, wherein the guest molecule contains at least a glycine, a repeating unit of kevlar, or a repeating unit of nylon-6,6.
* * * * *